(12) United States Patent
Valdez et al.

(10) Patent No.: US 11,402,395 B2
(45) Date of Patent: *Aug. 2, 2022

(54) COMPOUNDS AND METHODS FOR USE IN DETECTING GABAPENTIN

(71) Applicant: Ark Diagnostics, Inc., Fremont, CA (US)

(72) Inventors: Johnny Jose Valdez, Fremont, CA (US); Byung Sook Moon, Palo Alto, CA (US); Michael Kevin Helms, Foster City, CA (US); Alejandro A. Orozco, Gilroy, CA (US)

(73) Assignee: ARK Diagnostics, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/478,639

(22) Filed: Sep. 17, 2021

(65) Prior Publication Data

US 2022/0003793 A1    Jan. 6, 2022

Related U.S. Application Data

(60) Division of application No. 17/014,678, filed on Sep. 8, 2020, which is a division of application No. (Continued)

(51) Int. Cl.
*G01N 33/94* (2006.01)
*C07C 229/28* (2006.01)
(Continued)

(52) U.S. Cl.
CPC ....... *G01N 33/9473* (2013.01); *C07C 229/28* (2013.01); *C07C 233/36* (2013.01);
(Continued)

(58) Field of Classification Search
CPC ... C07C 229/28; C07C 233/36; C07C 233/47; C07C 321/04; C07C 323/25; C07K 16/44; G01N 33/53; G01N 33/5308
See application file for complete search history.

(56) References Cited

U.S. PATENT DOCUMENTS

| 3,817,837 A | 6/1974 | Rubenstein et al. |
| 3,875,011 A | 4/1975 | Rubenstein et al. |

(Continued)

FOREIGN PATENT DOCUMENTS

| EP | 0659751 | 6/1995 |
| EP | 1470825 | 10/2004 |

(Continued)

OTHER PUBLICATIONS

Chen et al., "Development of an Enzyme-Linked Immunosorbent Assay for a Broad Spectrum Triazole Fungicide: Hexaconazole" J. Agric. Food Chem 44 1352-1356 (1996).

(Continued)

*Primary Examiner* — Shafiqul Haq
(74) *Attorney, Agent, or Firm* — Rudy J. Ng; Bozicevic, Field & Francis LLP

(57) ABSTRACT

Compounds and methods for use in detecting gabapentin in a sample suspected of containing gabapentin are disclosed. Gabapentin derivatives are used to produce gabapentin conjugates. A gabapentin-immunogenic carrier conjugate may be used as an immunogen for the preparation of an anti-gabapentin antibody. A gabapentin-detectable label may be used in a signal producing system in gabapentin assays.

17 Claims, 12 Drawing Sheets

Related U.S. Application Data

16/247,255, filed on Jan. 14, 2019, now abandoned, which is a continuation of application No. 15/349,832, filed on Nov. 11, 2016, now Pat. No. 10,203,345, which is a division of application No. 14/447,179, filed on Jul. 30, 2014, now Pat. No. 9,522,880, which is a division of application No. 12/032,528, filed on Feb. 15, 2008, now Pat. No. 8,828,665.

(60) Provisional application No. 60/890,313, filed on Feb. 16, 2007.

(51) Int. Cl.
| | | |
|---|---|---|
| *C07C 233/36* | (2006.01) | |
| *C07C 233/47* | (2006.01) | |
| *C07C 323/25* | (2006.01) | |
| *C07K 16/44* | (2006.01) | |
| *G01N 33/53* | (2006.01) | |
| *C07C 321/04* | (2006.01) | |
| *A61K 39/00* | (2006.01) | |

(52) U.S. Cl.
CPC .......... *C07C 233/47* (2013.01); *C07C 321/04* (2013.01); *C07C 323/25* (2013.01); *C07K 16/44* (2013.01); *G01N 33/53* (2013.01); *G01N 33/5308* (2013.01); *A61K 2039/505* (2013.01); *A61K 2039/60* (2013.01); *C07C 2601/12* (2017.05); *C07C 2601/14* (2017.05)

(56) References Cited

U.S. PATENT DOCUMENTS

| | | | |
|---|---|---|---|
| 4,492,762 A | 1/1985 | Wang et al. | |
| 4,708,929 A | 11/1987 | Henderson | |
| 4,816,567 A | 3/1989 | Cabilly et al. | |
| 4,857,453 A | 9/1989 | Ullman et al. | |
| 4,868,131 A | 9/1989 | Hiratsuka | |
| 5,851,829 A | 12/1998 | Marasco et al. | |
| 5,965,371 A | 10/1999 | Marasco et al. | |
| 6,455,288 B1 | 9/2002 | Jakobovits et al. | |
| 6,514,770 B1 | 2/2003 | Sorin | |
| 6,784,197 B2 | 8/2004 | Differding et al. | |
| 7,037,939 B2 * | 5/2006 | Hwang | C07C 233/84 514/534 |
| 7,101,980 B2 | 9/2006 | Hui et al. | |
| 7,169,907 B2 | 1/2007 | Hui | |
| 7,183,259 B2 * | 2/2007 | Scheuerman | C07C 237/12 514/17.7 |
| 7,202,092 B2 | 4/2007 | Ghoshal et al. | |
| 7,205,116 B2 | 4/2007 | Salamone et al. | |
| 7,271,252 B2 | 9/2007 | Sigler | |
| 7,358,276 B2 | 4/2008 | Differding et al. | |
| 8,168,756 B2 | 5/2012 | Valdez et al. | |
| 8,828,665 B2 * | 9/2014 | Valdez | G01N 33/5308 435/7.1 |
| 9,522,880 B2 * | 12/2016 | Valdez | C07C 323/25 |
| 10,203,345 B2 * | 2/2019 | Valdez | C07C 233/47 |
| 2002/0058656 A1 | 5/2002 | Ockert | |
| 2002/0098999 A1 | 7/2002 | Gallop et al. | |
| 2002/0111338 A1 | 8/2002 | Cundy et al. | |
| 2002/0151529 A1 | 10/2002 | Cundy et al. | |
| 2003/0158254 A1 | 8/2003 | Zerangue et al. | |
| 2003/0181390 A1 * | 9/2003 | Gallop | A61P 25/28 514/17.6 |
| 2004/0248811 A1 * | 12/2004 | Hwang | C07C 237/20 514/18.2 |
| 2004/0254344 A1 | 12/2004 | Gallop et al. | |
| 2005/0148564 A1 | 7/2005 | Cundy et al. | |
| 2005/0228035 A1 | 10/2005 | Feuerstein et al. | |
| 2005/0244816 A1 | 11/2005 | Valdez | |
| 2005/0272710 A1 | 12/2005 | Cundy et al. | |
| 2005/0288228 A1 | 12/2005 | Cundy et al. | |
| 2006/0115865 A1 | 6/2006 | Ouyang et al. | |
| 2006/0141548 A1 | 6/2006 | Roberts et al. | |
| 2007/0135356 A1 | 6/2007 | Scheueman et al. | |
| 2008/0009018 A1 | 1/2008 | Ouyang et al. | |
| 2008/0199887 A1 | 8/2008 | Valdez et al. | |
| 2009/0093069 A1 | 4/2009 | Valdez et al. | |
| 2010/0173427 A1 | 7/2010 | Valdez et al. | |
| 2011/0105448 A1 | 5/2011 | Dhuppad et al. | |
| 2011/0212944 A1 | 9/2011 | Lui et al. | |
| 2012/0190047 A1 | 7/2012 | Valdez et al. | |
| 2014/0206020 A1 | 4/2014 | Valdez et al. | |
| 2020/0400696 A1 * | 12/2020 | Valdez | G01N 33/53 |

FOREIGN PATENT DOCUMENTS

| | | | |
|---|---|---|---|
| WO | WO 9700248 | 1/1997 | |
| WO | WO 9733858 | 9/1997 | |
| WO | WO-9733858 A1 * | 9/1997 | ............. A61P 25/28 |
| WO | WO 0050027 | 8/2000 | |
| WO | WO-0142191 A1 * | 6/2001 | ............. A61P 25/00 |
| WO | WO 2001062726 | 8/2001 | |
| WO | WO 200228883 | 4/2002 | |
| WO | WO 200242414 | 5/2002 | |
| WO | WO 200300642 | 1/2003 | |
| WO | WO 2007065036 | 6/2007 | |
| WO | WO 2008097640 | 8/2008 | |
| WO | WO 2011020605 | 2/2011 | |
| WO | WO 2012172015 | 12/2012 | |

OTHER PUBLICATIONS

Cendejas-Bueno et al., "HPLC/UV or bioassay: two valid methods for posaconazole quantification in human serum samples," Clin. Microbiol. Infect., 18(12) 1229-1235 (2012).

Coachman et al., "An automated method for the simultaneous measurement of azole antifungal drugs in human plasma or serum using turbulent flow liquid chromatography-tandem mass spectrometry" Anal Bioanal Chem. 404:513-523 (2012) XP035083685.

Contin et al., "Levetiracetam Therapeutic Monitoring in Patients with Epilepsy Effect of Concomitant Antiepileptic Drugs," *Ther Drug Monit.* 26(4): 375-379(2004).

Engiebienne "Immune and Receptor Assays in Theory and Practice," CRC Press 308—(2000).

Engvall "Enzyme immunoassay ELISA and EMIT," *Methods Enzymol* 70:419-439 (1980).

Extended European Search Report for European Application No. 09822719.2, dated Jan. 11, 2012.

Feng et al. "Structural characterization of the oxidative degradation products of an antifungal agent SCH 56592 by LC-NMR and LC-MS." J. of Pharm and Biom. Analysis 25 (3-4): 545-557 (2001).

Goodrow, et al., "Strategies for Immunoassay Hapten Design," In Immunoanalysis of Agrochemicals, 586(9): 119-139 (1995).

Gunther, et al., "QMS Levetiracetam Assay on the Hitachi 917 System," Clinical Chemistry, 55(6): Supplement, Abstract E-167 (2009).

Howard, et al., "Clinical application of voriconazole concentrations in the treatment of invasive aspergillosis," Ann. Pharmacother., 42(12): 1859-1864 (2008).

Hurwitz, et al., "Levetiracetam Induced Interstitial Nephritis and Renal Failure," Pediatr. Neurol, 41:57-58 (2009).

Kenda, et al.; "Discovery of 4-Substituted Pyrrolidone Butanamides as New Agents with Significant Antiepileptic Activity," *J. Med. Chem.*, 47(3):530-535 (2004).

Kohler and Milstein,"Continuous cultures of fused cells secreting antibody of predefined specificity," Nature, 256: 495-497 (1975).

Manclus et al., "Development of Monoclonal Immunoassays for the Determination of Triazole Fungicides in Fruit Juices," J. Agric. Food Chem. 56: 8793-8800 (2008) XP055291307.

Mayer, et al., "Luminescent Label-ore than just an alternative to radioisotopes?" *Angewandte Chemie*, 33(10), 1044-1072 (1994).

McCafferty, et al., "Phage antibodies: filmentous phage displaying antibody variable domains," *Nature* 348:552-554 (1990).

Na, "Synthesis and Activity of Novel 1-Halogenobenzylindole Linked Triazole Derivatives as Antifungal Agents" Bull. Korean Chem Soc. 32(1): 307-310 (2011).

(56) References Cited

OTHER PUBLICATIONS

Nagappan et al., "Posaconazole: A Broad-Spectrum Triazole Antifungal Agent" Clinical Infectious Diseases 45(12):1610-1617 (2007).
Nolli, et al., "Antibodies against the antibiotics: an overview," *Ann. 1st Super Sanita*, 27(1):149-154 (1991).
Noyer, et al. "The Novel Antiepileptic Drug Levetiracetam (ucb L059) Appears to Act via a Specific Binding Site in CNS Membranes" *Eur. J. Pharmolcol.* 286(2):137-146 (1995).
Oh, et al., "ARKTM Homogeneous Enzyme Immunoassays for Voriconazole and Posaconazole," posted on Internet on Sep. 19, 2013.
Roffey, et al., "The Disposition of Voriconazole in Mouse, Rat, Rabbit, Guinea Pig, Dog, and Human" *Drug Metabolism and Disposition*, 31(6):731-781 (2003).
Sargentini-Maier, et al., "Pharmacokinetics and Metabolism of 14C-Brivaracetam, a Novel SV2A Ligand, in Healthy Subjects" *Drug Metab. Dispos.* ,36(1):36-45 (2008).
Schiller et al., "Posaconazole: An extended-spectrum triazole antifungal agent," Clinical Therapeutics, Excerpta Medica Princeton 29(9) 1862-1886 (2007) XP022354377.

\* cited by examiner

14

41  42

16

43  44

COMPOUNDS AND METHODS FOR USE IN DETECTING GABAPENTIN

CROSS-REFERENCE TO RELATED APPLICATIONS

This application is a divisional of U.S. application Ser. No. 17/014,678, filed Sep. 20, 2020, which is a divisional of U.S. application Ser. No. 16/247,255, filed Jan. 14, 2019, which is a continuation of U.S. application Ser. No. 15/349,832, filed Nov. 11, 2016, now issued as U.S. Pat. No. 10,203,345, which is a divisional of U.S. application Ser. No. 14/447,179, filed Jul. 30, 2014, now issued as U.S. Pat. No. 9,522,880, which is a divisional of U.S. application Ser. No. 12/032,528, filed Feb. 15, 2008, now issued as U.S. Pat. No. 8,828,665, which claims the benefit of U.S. Provisional Application No. 60/890,313, filed Feb. 16, 2007, the disclosures of each of which applications are incorporated herein by reference.

FIELD OF THE INVENTION

The invention relates to therapeutic drug monitoring (TDM) of gabapentin.

BACKGROUND OF THE INVENTION

Gabapentin, (1-aminomethyl)cyclohexane-1-acetic acid) is an antiepileptic drug, which has been found to have pain-relieving properties. Gabapentin is indicated for the management of post-herpetic neuralgia in adults. It is reported as adjunctive therapy in the treatment of partial seizures with and without secondary generalization in patients over 12 years of age with epilepsy and in the treatment of partial seizures in pediatric patients age 3-12 years. Additionally, it is indicated to have anti-anxiety activity as also beneficial properties in treating neuro-degenerative diseases like Alzheimer's.

There can be a variable relationship between the dose of gabapentin and the resulting serum drug concentration that provides a therapeutic effect. This can be due to variability of intra- and inter-individual pharmacokinetics. As a result of this variability, equal doses of the same drug in different individuals can result in dramatically different clinical outcomes. For example, effectiveness of the same gabapentin dosage can vary significantly between patients based upon individual drug clearance and the ultimate serum drug concentration in the patient. In addition, therapeutic drug management of gabapentin can serve as an excellent tool to ensure compliance in administering chemotherapy with the actual prescribed dosage and achievement of the effective serum concentration levels.

Therapeutic drug management (TDM) can provide the clinician with insight on patient variation, and allow the clinical to individualize drug dosages to the patient's needs. For example, absorption of gabapentin can be saturated as the dose is titrated, so physicians may use TDM to confirm the plasma concentration increases with increasing doses. Thus, monitoring of levels of gabapentin in the body, and adjusting the dose as may be advised, can serve to better control therapy and limit undesirable side effects in patients.

The majority of data regarding gabapentin drug levels has been derived using either liquid chromatographic (Hengy & Kolle, 1985; Ratnaraj & Patsalos 1998, Chollet et al, 200, Wad & Kramer, 1998, Ifa et al. 2001) or gas chromatographic techniques (Hooper et al., 1990, Kushnir et al., 1999). While chromatographic techniques can be used to determine drug levels, such methods are impractical for commercial use due to, for example, long sample preparation time, long assay time, high cost, and labor-intensive procedures. Immunoassays provide simple and fast analytical methods for measurement of drug levels.

SUMMARY OF THE INVENTION

The present disclosure provides methods and compounds for use in detecting gabapentin in a sample.

FEATURES OF THE INVENTION

The present invention features a compound having the structure:

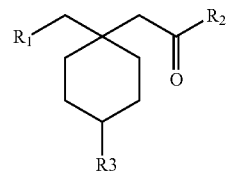

where $R_1$, $R_2$, or $R_3$ is -X-W-L-Z; where: when $R_1$ is -X-W-L-Z, X is NH, and $R_2$ is —OH, and $R_3$ is —H, when $R_2$ is -X-W-L-Z, X is NH, $R_1$ is —NH$_2$, and $R_3$ is —H, and when $R_3$ is -X-W-L-Z, X is a heteroatom or lower alkyl group, $R_1$ is —NH$_2$, and $R_2$ is —OH, and W is a lower alkyl group or a carbonyl group; L is a linker or at least one bond between W and Z; and Z is H, an alkyl group, a reactive functional group capable of reacting with a reactive partner to form a covalent bond, or a moiety of interest; or a salt thereof.

In some embodiments, the linker comprises 0 to 40 carbon atoms and 0-6 heteroatoms. In some embodiments, W is a lower alkyl and said linker is selected from the group consisting of —(CH$_2$)$_n$C(O)—, —C(O)(CH$_2$)$_n$—, —C(O)(CH$_2$)$_n$NH—C(O)—, —C(O)(CH$_2$)$_m$NH—C(O)(CH$_2$)$_n$—, —(CH$_2$)$_n$SCH$_2$C(O)—, —(CH$_2$)$_m$SCH$_2$C(O)(CH$_2$)$_n$—, —(CH$_2$)$_m$C(O)NH(CH$_2$)$_n$—, —(CH$_2$)$_n$NH—C(O)—, —(CH$_2$)$_m$NH—C(O)(CH$_2$)$_n$—, —C(O)—(CH$_2$)$_n$—, and —(CH$_2$)$_n$—; wherein m, n, o, and p are independently selected from an integer from 0 to 10.

In some embodiments, W is a carbonyl and said linker is selected from the group consisting of —(CH$_2$)$_n$C(O)—, —(CH$_2$)$_n$SCH$_2$C(O)—, —(CH$_2$)$_m$SCH$_2$C(O)(CH$_2$)$_n$—, —(CH$_2$)$_m$C(O)NH(CH$_2$)$_n$—, —(CH$_2$)$_n$NH—C(O)—, —(CH$_2$)$_m$NH—C(O)(CH$_2$)$_n$—, and —(CH$_2$)$_n$—; wherein m, n, o, and p are independently selected from an integer from 0 to 10. In some embodiments, W is a methyl group.

In some embodiments, the reactive functional group is selected from the group consisting of halogen, OH, SH, NH$_2$, O-lower alkyl, epoxy, S-acyl, carboxyl, maleimidyl, haloacetamide, hydroxysuccinimidyl, succinimidyl, carbonate, anhydride and imidate. In some embodiments, the halogen is Br or I.

In some embodiments, the compound has the following structure:

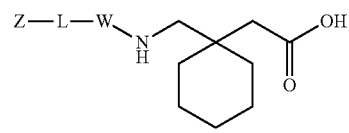

wherein Z, L, and W are as defined above.

In some embodiments, Z is SH or Br. In some embodiments, Z is a reactive functional group, and wherein -W-L-Z is a straight or branched alkyl chain. In some embodiments, Z is a reactive functional group, and wherein W is a lower alkyl group.

In some embodiments, the compound has the following structure:

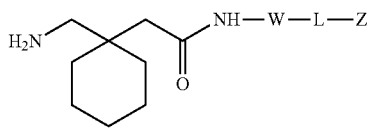

wherein W, L and Z are as defined above.

In some embodiments, Z is a reactive functional group, the reactive functional group is selected from the group consisting of halogen, SH, NH$_2$, O-lower alkyl, epoxy, S-acyl, maleimidyl, haloacetamide, hydroxysuccinimidyl, succinimidyl, carbonate, anhydride and imidate.

In some embodiments, the compound has the following structure:

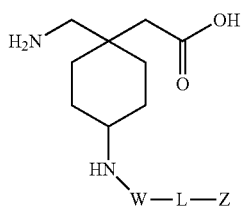

wherein W, L and Z are as defined above.

In some embodiments, Z is SH or Br. In some embodiments, -X-W-L-Z is selected from the group consisting of —NH—(CH$_2$)$_m$—SH, —NH—CO—(CH$_2$)$_n$—Br, and —NH—(CH$_2$)$_o$—S—CH$_2$—CO—CH$_2$—Br; and m, n, and o are independently selected from 2 or 3.

In some embodiments, Z is a moiety of interest. In some embodiments, the moiety of interest is an enzyme. In some embodiments, the enzyme is a glucose-6-phosphate dehydrogenase (G6PDH). In some embodiments, the G6PDH comprises at least one cysteine per subunit, and the cysteine is not native to a naturally-occurring G6PDH. In some embodiments, the enzyme is selected from alkaline phosphatase, β-galactosidase and horseradish peroxidase.

In some embodiments, the moiety of interest is a carrier protein. In some embodiments, the carrier protein is bovine serum albumin (BSA). In some embodiments, the carrier protein is keyhole limpet hemocyanin (KLH). In some embodiments, the carrier protein is selected from the group consisting of hemocyanins, globulins, albumins, and polysaccharides.

In some embodiments, the compound is immunogenic.

In some embodiments, the moiety of interest is a detectable label. In some embodiments, the detectable label is selected from a fluorophore, a fluorescence quencher, a radioisotope, and metal. In some embodiments, the detectable label is selected from a polypeptide, a nucleic acid, a polysaccharide, and a lipid.

In some embodiments, the compound is immobilized on a support.

In some embodiments, the moiety of interest is bound to the compound through CONH, NHCO, NHCONH, NH—(C=S)—NH, O—CO—NH, NH—O—CO, S, NH—(C=NH), N=N, or NH.

In some embodiments, the moiety of interest is selected from a fluorophore, a fluorescence quencher, a radioisotope, and metal. In some embodiments, the moiety of interest is selected from a polypeptide, a nucleic acid, a polysaccharide, and a lipid.

The present invention features a method for detecting the presence or absence of gabapentin in a sample. The method generally involves:

(a) adding, to a reaction mixture, (i) a sample suspected of containing gabapentin and (ii) an anti-gabapentin antibody capable of forming of a complex of gabapentin that may be present in the sample and the antibody; and (b) detecting the presence or absence of the complex;

wherein the presence or absence of the complex is indicative of the presence or absence of gabapentin in the sample.

In some embodiments, the method further comprises adding a gabapentin conjugate comprising a gabapentin moiety and a detectable label to said sample, where the gabapentin conjugate is capable of binding to the anti-gabapentin antibody; and where detecting is by detecting the detectable label.

In some embodiments, the moiety of interest is the detectable label. In some embodiments, the detectable label comprises an enzyme and the detecting is by assaying activity of the enzyme. In some embodiments, enzymatic activity is elevated when the complex is present.

In some embodiments, the enzyme is a dehydrogenase. In some embodiments, the dehydrogenase is G6PDH.

In some embodiments, the method further comprises measuring the amount of the conjugate bound to the anti-gabapentin antibody. In some embodiments, the detecting is quantitative.

In some embodiments, the detectable label is selected from a fluorophore, a fluorescence quencher, a radioisotope, and metal. In some embodiments, the detectable label is selected from a polypeptide, a nucleic acid, a polysaccharide, and a lipid.

In some embodiments, the method is a homogeneous immunoassay. In some embodiments, the method is a heterogeneous immunoassay.

In some embodiments, the sample is a biological sample obtained from a human. In some embodiments, the biological sample is blood or a blood-derived sample.

The present invention features an antibody that specifically binds gabapentin. In some embodiments, the antibody is selected from a Fab, Fab', F(ab')'2, Fv fragment, and a single-chain antibody. In some embodiments, the antibody is a monoclonal antibody.

The present invention features a kit comprising: an anti-gabapentin antibody capable of specifically binding to gabapentin; and a gabapentin calibration standard.

In some embodiments, the kit further comprises a conjugate comprising a gabapentin moiety and a detectable signal. In some embodiments, the detectable label is an enzyme, and the kit further comprises a substrate for the enzyme.

These and other objects, advantages, and features of the invention will become apparent to those persons skilled in the art upon reading the details of the details of the compounds and methods for use in detecting gabapentin as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF EXEMPLARY EMBODIMENTS

Figure 1:
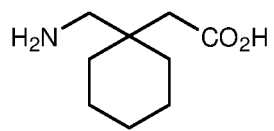
FIG. 1 is a schematic showing the structure of gabapentin.

Before exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some exemplary methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a conjugate" includes a plurality of such conjugates and reference to "the sample" includes reference to one or more samples and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Unless defined otherwise, all technical and scientific terms used herein have the same meaning as commonly understood by one of ordinary skill in the art to which this invention is related. The following terms are defined for purposes of the present disclosure.

A "gabapentin derivative" as used in this disclosure refers to a compound sharing a core structure with gabapentin and that can compete with gabapentin for binding to an anti-gabapentin binding partner, such as an anti-gabapentin antibody.

Certain compounds disclosed herein in connection with embodiments of the present invention can exist in unsolvated forms as well as solvated forms, including hydrated forms. In general, the solvated forms are equivalent to unsolvated forms and are encompassed within the reference to the compounds set out in the present disclosure. Certain compounds disclosed herein in connection with embodiments of the present invention may exist in multiple crystalline or amorphous forms.

As used herein, the term "isolated," when used in the context of an isolated compound, antibody, conjugate, etc., refers to a compound of interest (e.g., a compound as described herein, a conjugate as described herein, an antibody as described herein, etc.) that is in an environment different from that in which the compound naturally occurs. "Isolated" is meant to include compounds of interest (e.g., a compound as described herein, a conjugate as described herein, or an antibody as described herein) that are within samples that are substantially enriched for the compound of interest and/or in which the compound of interest is partially or substantially purified. As used herein, the term "substantially pure" refers to a compound of interest that is removed from its natural environment and is at least 60% free, at least about 75% free, at least about 90% free, at least about 95% free, at least about 98% free, or more than 98% free, from other components with which it is naturally associated, and/or with it may be associated during synthesis or production.

Certain compounds disclosed herein in connection with embodiments of the present invention possess asymmetric carbon atoms (optical centers) or double bonds; the racemates, diastereomers, geometric isomers and individual isomers are encompassed within the scope of the present invention.

The compounds may be prepared as a single isomer (e.g., enantiomer, cis-trans, positional, diastereomer) or as a mixture of isomers. In one embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), Vogel's Encyclopedia of Practical Organic Chemistry, 5th ed., Longman Scientific and Technical Ltd., Essex, 1991, pp. 809-816; and Heller, Acc. Chem. Res. 23: 128 (1990).

Where substituent groups are specified by their conventional chemical formulae, written from left to right, they equally encompass the chemically identical substituents, which would result from writing the structure from right to left, e.g., —CH$_2$O— is intended to also recite —OCH$_2$—. Use of a single dash ("—") or double dash ("—" or "═") refers to a single covalent bond, while use of "═" refers to a double bond. The symbol, )$_2$ or $_2$(, when displayed with —S, indicates that the compound inside the parenthesis may be present as a dimer forming a disulfide bond. The dimer may be reduced to a monomer.

The term "acyl" or "alkanoyl" by itself or in combination with another term, means, unless otherwise stated, a stable straight or branched chain, or cyclic hydrocarbon radical, or combinations thereof, having the stated number of carbon atoms and an acyl radical on at least one terminus of the alkane radical. The "acyl radical" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl", where "heteroalkyl" refers to carbon chains having one or more substitutions at one or more carbon atoms of the hydrocarbon chain fragment. Alkyl groups that are limited to hydrocarbon groups are termed "homoalkyl". Exemplary alkyl groups include those containing between about one and about twenty five carbon atoms (e.g. methyl, ethyl and the like).

The term "lower alkyl" generally refers to a straight, branched, or cyclic hydrocarbon chain containing 8 or fewer carbon atoms, and can contain from 1 to 8, from 1 to 6, or from 1 to 4 carbon atoms. Exemplary "lower alkyl" groups include methyl, ethyl, n-propyl, isopropyl, n-butyl, sec-butyl, tert-butyl, n-pentyl, n-hexyl, n-heptyl and the like. "Lower alkyls" can be optionally substituted at one or more carbon atoms of the hydrocarbon chain.

The terms "alkoxy," "alkylamino" and "alkylthio" (or thioalkoxy) are used to refer to those alkyl groups attached to the remainder of the molecule via an oxygen atom, an amino group, or a sulfur atom, respectively.

By "heteroatom" is meant atoms other than a carbon which may be present in a carbon backbone or a linear, branched or cyclic compound. Exemplary heteroatoms include oxygen (O), nitrogen (N), sulfur (S), phosphorus (P) and silicon (Si). Heteroatoms can be present in their reduced forms, e.g., —OH, —NH, and —SH.

The term "heteroalkyl," by itself or in combination with another term, means, unless otherwise stated, a straight or branched chain, or cyclic carbon-containing radical, or combinations thereof, having the stated number of carbon atoms and at least one hetero atom which can be a member selected from O, N, Si, P and S, wherein the nitrogen, phosphorous and sulfur atoms are optionally oxidized, and the nitrogen heteroatom is optionally be quaternized. Normally heteroalkyl groups contain no more than two heteroatoms linked in sequence. The heteroatom(s) O, N, P, S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH═N—OCH$_3$, and —CH═CH—N(CH$_3$)—CH$_3$. Generally, up to two heteroatoms may be consecutive, such as, for example, —CH$_2$—NH—OCH$_3$ and —CH$_2$—O—Si(CH$_3$)$_3$.

Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (usually from 1 to 3 rings), which are fused together or linked covalently. The term "heteroaryl" refers to aryl groups (or rings) that contain from one to four heteroatoms which are members selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" where each can be independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$) alkoxy, and fluoro(C$_1$-C$_4$)alkyl, in a number ranging from zero to the total number of open valences on the aromatic ring system; and where R', R", R'" and R"" can be independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present. In the schemes that follow, the symbol X represents "R" as described above.

The term "amino" or "amine group" refers to the group —NR'R" (or N$^+$RR'R") where R, R' and R" are independently selected from hydrogen, alkyl, substituted alkyl, aryl, substituted aryl, aryl alkyl, substituted aryl alkyl, heteroaryl, and substituted heteroaryl. A substituted amine is an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N$^+$RR'R" and its biologically compatible anionic counterions.

The term "conjugate" refers to a molecule comprised of two or more moieties bound together, optionally through a linking group, to form a single covalent structure. The binding can be made either by a direct chemical bond between the components or by use of a linking group. For example, a gabapentin conjugate generally refers to a chemical compound composed of a gabapentin derivative covalently bound to a moiety of interest, which may be optionally linked through a linking group. In another example, a "gabapentin-enzyme conjugate" refers a gabapentin conjugate having an enzyme as the moiety of interest.

A "hapten" generally refers to a small molecule that can be specifically bound by an antibody but cannot induce detectable or significant formation of antibodies unless bound to a carrier protein or other large antigenic molecule. In the context of the present disclosure, gabapentin and gabapentin derivative is an exemplary hapten. In contrast, an "antigen" refers to a compound that is capable of stimulating an immune response.

The term "linker" as used in the present disclosure refers to a chemical moiety that connects at least two substructures of a compound, e.g., to provide for covalent connection between a gabapentin hapten and a moiety of interest (e.g., a carrier or detectable label).

A "carrier" or "immunogenic carrier," as the terms are used herein, is an immunogenic substance, commonly a polypeptide, that can join with a hapten (such as a gabapentin moiety), thereby enabling the happen to induce an immune response and elicit the production of antibodies that can bind specifically with the antigen (hapten). Carrier substances include, but are not necessarily limited to, proteins, glycoproteins, complex polysaccharides, particles, and nucleic acids that are recognized as foreign and thereby elicit an immunologic response from the host.

"Polypeptide" as used herein is meant to encompass a polyaminoacid of any length, and encompasses proteins, protein fragments and peptides. Polypeptides may be genetically encoded or synthetically produced. Polypeptides may also be modified, e.g., by post-translational and/or chemical modification(s).

As used herein, a "detectable label" generally refers to an identifying tag that can provide for a detectable signal, e.g., luminescence (e.g., photoluminescence (e.g., fluorescence, phosphorescence), chemoluminescence (e.g., bioluminescence)), radioactivity, immunodetection, enzymatic activity, and the like).

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies include hybrid and recombinant antibodies produced by splicing a variable (including hypervariable) domain of an anti-inhibitor antibody with a constant domain, or a light chain with a heavy chain, or a chain from one species with a chain from another species, or fusions with heterologous proteins, regardless of species of origin or immunoglobulin class or subclass designation, as well as antibody fragments, e.g., Fab, F(ab)2, and Fv!, so long as they exhibit the desired biological activity. For example, the monoclonal antibodies may be made by the hybridoma method first described by Kohler & Milstein, Nature, 256:495 (1975), or may be made by recombinant DNA methods (U.S. Pat. No. 4,816,567). The "monoclonal antibodies" may also be isolated from phage libraries generated using the techniques described in, e.g., McCafferty et al., Nature, 348:552-554 (1990).

The term "anti-gabapentin antibody" refers to antibodies that are capable of specifically binding a gabapentin epitope of gabapentin, a gabapentin derivative, or a gabapentin conjugate. "Anti-gabapentin antibodies" include both polyclonal and monoclonal antibodies, as well as antigen-binding fragments thereof as defined above. A "gabapentin epitope" refers to an epitope that is present in gabapentin and in a gabapentin derivative (e.g., a gabapentin conjugate).

The term "binds specifically" or "specifically binds" in the context of antibody binding, refers to high avidity and/or high affinity binding of an antibody to a specific antigen, e.g., to gabapentin. In specific binding under appropriate conditions, antibody binding to gabapentin is stronger than binding of the same antibody to any other epitope, particularly those which may be present in molecules in association with, or in the same sample, as the gabapentin to be detected, e.g., binds more strongly (e.g., higher affinity, higher avidity, or both) to gabapentin than to a non-gabapentin epitope so that by adjusting binding conditions the antibody binds almost exclusively to gabapentin, and not to non-gabapentin moieties that may be present in the sample. Antibodies which bind specifically to gabapentin may be capable of binding other antigens at a weak, yet detectable, level (e.g., 10% or less of the binding shown to gabapentin). Such weak binding, or background binding, is readily discernible from the specific antibody binding to gabapentin, e.g., by use of appropriate controls. "Antibody activity" or "antibody binding activity" in the context of analyte binding assays generally refers to the ability of an antibody to bind a specific antigen in preference to other potential antigens via the antigen combining site located within a variable region of an immunoglobulin.

By "detectably labeled antibody" an antibody (which, as defined above, includes antigen-binding fragments, etc.) having an attached detectable label. The detectable label may be attached by chemical conjugation, but where the label is a polypeptide, it could alternatively be attached by genetic engineering techniques. Methods for production of detectably labeled proteins are well known in the art. Detectable labels may be selected from a variety of such labels known in the art, but normally are radioisotopes, fluorophores, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies to detect an antigen are well known in the art.

"Antibody complex", "antibody-antigen complex" generally refers to a complex that results following specific binding of an antibody and its antigen, e.g., between an anti-gabapentin antibody and gabapentin (or a gabapentin derivative, e.g., gabapentin conjugate).

The term "analyte" refers to a substance to be detected in a sample, e.g., gabapentin.

The term "assessing" includes any form of measurement, and includes determining the presence or absence if an element. The terms "assessing", "determining" (e.g., as in "determining the presence or absence of"), "measuring", "evaluating", and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

Gabapentin Derivatives

Gabapentin derivatives for the use in gabapentin therapeutic drug monitoring (TDM) are provided in the present disclosure. The term "gabapentin derivatives" is meant to encompass gabapentin-conjugates including immunogens and assay reagents (e.g., detectably labeled conjugates, such as enzyme conjugates, immobilized conjugates, and the like), as well as intermediates useful in production of such gabapentin conjugates. In general, a gabapentin derivative is able to compete with gabapentin for binding to an anti-gabapentin antibody, e.g., in a gabapentin TDM assay. A schematic representation of the structure of gabapentin is shown in FIG. 1

Structures of Gabapentin Derivatives

Gabapentin derivatives of the present disclosure can be described as having the general formula:

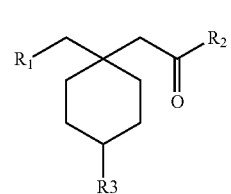

(A)

wherein R$_1$, R$_2$, or R$_3$ is -X-W-L-Z, wherein
when R$_1$ is -X-W-L-Z, X is NH, and R$_2$ is —OH, and R$_3$ is —H,
when R$_2$ is -X-W-L-Z, X is NH, R$_1$ is —NH$_2$, and R$_3$ is —H, and
when R$_3$ is -X-W-L-Z, X is a heteroatom or lower alkyl group, R$_1$ is —NH$_2$, and R$_2$ is —OH, and
W is a lower alkyl group or a carbonyl group;

L is a linker or at least one bond between W and Z; and

Z is H, an alkyl group, a reactive functional group capable of reacting with a reactive partner to form a covalent bond, or a moiety of interest;

or a salt thereof.

As noted above, the term "linker" as used in the present disclosure refers to a chemical moiety that connects at least two substructures of a compound, e.g., to provide for covalent connection between a gabapentin hapten and a moiety of interest (e.g., a carrier or detectable label). In the context of a gabapentin conjugate, the linker can be a chemical moiety that is the production of a reaction between a reactive functional group and a moiety of interest, e.g., a polypeptide. Exemplary linkers include linear or branched, saturated or unsaturated, hydrocarbon chains of from 1 to 40 carbon atoms, or from 1 to 20 carbon atoms, or from 1 to 10 carbon atoms, which hydrocarbon chains may contain ring structures (e.g., up to two ring structures) and one or more heteroatoms.

When W of Formula A is a lower alkyl group, W can be, for example, a straight, branched, or cyclic hydrocarbon chain containing 1 to 8 carbon atoms, from 1 to 6 carbon atoms, or from 1 to 4 carbon atoms.

In general, when W of Formula A is a carbonyl group, then L is a linker, which can be, for example, a hydrocarbon chain of from 1 to 40 carbon atoms, or from 1 to 20 carbon atoms, or from 1 to 10 carbon atoms, which hydrocarbon chains may optionally contain ring structures (e.g., up to two ring structures) and one or more heteroatoms.

Where W is a lower alkyl exemplary linkers include:
—$(CH_2)_nC(O)$—,
—$C(O)(CH_2)_n$—,
—$C(O)(CH_2)_nNH$—$C(O)$—,
—$C(O)(CH_2)_mNH$—$C(O)(CH_2)_n$—,
—$(CH_2)_nSCH_2C(O)$—,
—$(CH_2)_mSCH_2C(O)(CH_2)_n$—,
—$(CH_2)_mC(O)NH(CH_2)_n$—,
—$(CH_2)_nNH$—$C(O)$—,
—$(CH_2)_mNH$—$C(O)(CH_2)_n$—,
—$C(O)$—$(CH_2)_n$—, and
—$(CH_2)_n$—;
wherein m, n, o, and p are independently selected from an integer from 0 to 10, or from 1 to 10.

Where W is a carbonyl, exemplary linkers include:
—$(CH_2)_nC(O)$—,
—$(CH_2)_nSCH_2C(O)$—,
—$(CH_2)_mSCH_2C(O)(CH_2)_n$—,
—$(CH_2)_mC(O)NH(CH_2)_n$—,
—$(CH_2)_nNH$—$C(O)$—,
—$(CH_2)_mNH$—$C(O)(CH_2)_n$—, and
—$(CH_2)_n$—;
wherein m, n, o, and p are independently selected from an integer from 0 to 10, or from 1 to 10.

In some embodiments, such as when Z is a reactive functional group and R1 is -X-W-L-Z, W is a lower alkyl. In some embodiments, such as when Z is a reactive functional group and R2 is -X-W-L-Z, the reactive functional group is not OH or COOH.

In some embodiments, such as when Z is a reactive functional group and R1 is X-W-L-Z, and -X-W-L-Z does not include a ring.

In some embodiments, the moiety of interest is not a single amino acid residue, but may be a polyamino acid chain (i.e., polypeptide). In some embodiments, the moiety of interest is not a bile acid. In some embodiments where the moiety of interest is a polypeptide, the polypeptide is other than a transporter protein. In some embodiments, the gabapentin derivative is not a bile acid conjugate. In some embodiments, the moiety of interest is not a bile acid.

When Z of Formula A is a reactive functional group capable of reacting with a reactive partner to form a covalent bond, Z can be, for example a halogen (e.g., Br, Cl, I, and the like), OH, SH, $NH_2$, O-lower alkyl, epoxy, S-acyl, carboxyl, maleimidyl, haloacetamide, hydroxysuccinimidyl, succinimidyl, carbonate, anhydride, imidate, isocyanates, isothiocyanates, imidoesters, maleimides, thiolactones, diazonium groups, acrylamide, an acyl azide, an acyl nitrile, an alkyl halide, an aniline, an aryl halide, an azide, an aziridine, a boronate, a diazoalkane, a halotriazine, a hydrazine, a hydrazide, an imido ester, a phosphoramidite, a reactive platinum complex, a sulfonyl halide, and a photo-activatable group.

Moieties of interest for Z of Formula A include immunogenic carriers (e.g., carrier proteins) and detectable labels. Moieties of interest are described in more detail below.

Salts of gabapentin derivatives include, but are not necessarily limited to, alkali metal salts, such as (sodium salts, potassium salts, magnesium salts), halide salts (e.g., bromo, chloro, and the like); acetate salts (e.g., salts with trifluoroacetic acid, and the like).

Gabapentin derivatives can be further described as having a formula selected from

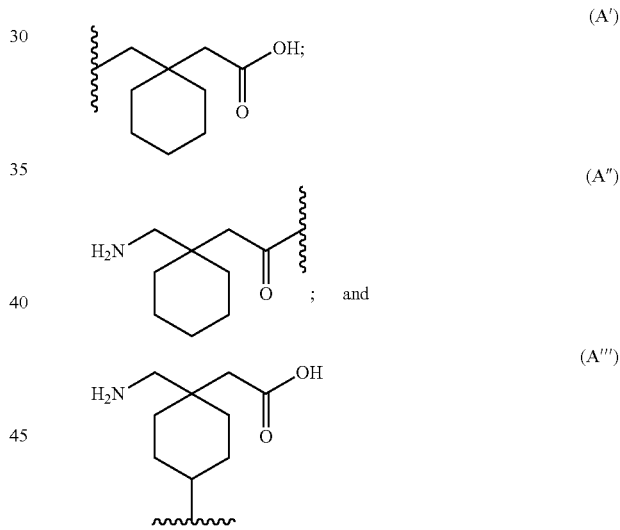

wherein the wavy line (" $\sim\sim\sim$ ") indicates the point at which the gabapentin moiety is attached to the remainder of the gabapentin derivative, e.g., attached through one or more chemical moieties to a moiety of interest, e.g., a gabapentin conjugate, e.g., a gabapentin conjugate having a immunogenic carrier or a detectable label. For example, the wavy line can represent a site of attachment to a polypeptide, detectable label, solid support, and the like, where attachment can be through a chemical structure as set out above.

Gabapentin derivatives may be provided as dimers. Such dimeric gabapentin derivatives can form from reaction of gabapentin derivatives having a sulfhydryl group or bromoacetyl group as a reactive functional group (Z). Thus, for example, dimerized gabapentin derivatives connected through a disulfide bond of a reactive group. Such dimers may be reduced to result in two monomeric gabapentin derivatives.

Further examples of gabapentin derivatives are described below.

Gabapetin Derivatives of Formula I

In one embodiment the gabapentin derivative has Formula I below, in which the gabapentin derivative includes an extension from the amine group of gabapentin or its salt:

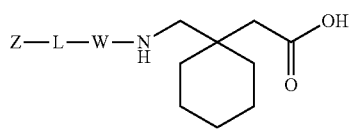

(I)

W, L, and Z can be as defined above in Formula A, and can be any combinations exemplified for Formula A as set out above. Accordingly, when W of Formula I is a lower alkyl group, W can be, for example, a straight, branched, or cyclic hydrocarbon chain containing 1 to 8 carbon atoms, from 1 to 6 carbon atoms, or from 1 to 4 carbon atoms. In general, when W of Formula I is a carbonyl group, then L is a linker, which can be, for example, a hydrocarbon chain of from 1 to 40 carbon atoms, or from 1 to 20 carbon atoms, or from 1 to 10 carbon atoms and one or more heteroatoms.

Where W is a lower alkyl exemplary linkers for gabapentin derivatives of Formula I include:
—$(CH_2)_nC(O)$—,
—$C(O)(CH_2)_n$—,
—$C(O)(CH_2)_nNH$—$C(O)$—,
—$C(O)(CH_2)_mNH$—$C(O)(CH_2)_n$—,
—$(CH_2)_nSCH_2C(O)$—,
—$(CH_2)_mSCH_2C(O)(CH_2)_n$—,
—$(CH_2)_mC(O)NH(CH_2)_n$—,
—$(CH_2)_nNH$—$C(O)$—,
—$(CH_2)_mNH$—$C(O)(CH_2)_n$—,
—$C(O)$—$(CH_2)_n$—, and
—$(CH_2)_n$—;
wherein m, n, o, and p are independently selected from an integer from 0 to 10, or from 1 to 10.

Where W is a carbonyl, exemplary linkers include:
—$(CH_2)_nC(O)$—,
—$(CH_2)_nSCH_2C(O)$—,
—$(CH_2)_mSCH_2C(O)(CH_2)_n$—,
—$(CH_2)_mC(O)NH(CH_2)_n$—,
—$(CH_2)_nNH$—$C(O)$—,
—$(CH_2)_mNH$—$C(O)(CH_2)_n$—, and
—$(CH_2)_n$—;
wherein m, n, o, and p are independently selected from an integer from 0 to 10, or from 1 to 10.

When Z of Formula A is a reactive functional group capable of reacting with a reactive partner to form a covalent bond, Z can be, for example a halogen (e.g., Br, Cl, I, and the like), OH, SH, $NH_2$, O-lower alkyl, epoxy, S-acyl, carboxyl, maleimidyl, haloacetamide, hydroxysuccinimidyl, succinimidyl, carbonate, anhydride, imidate, isocyanates, isothiocyanates, imidoesters, maleimides, thiolactones, diazonium groups, acrylamide, an acyl azide, an acyl nitrile, an alkyl halide, an aniline, an aryl halide, an azide, an aziridine, a boronate, a diazoalkane, a halotriazine, a hydrazine, a hydrazide, an imido ester, a phosphoramidite, a reactive platinum complex, a sulfonyl halide, and a photoactivatable group. Reactive functional groups for Z can be any of those as exemplified for Z of Formula A.

Moieties of interest for Z of Formula I include immunogenic carriers (e.g., carrier proteins) and detectable labels. Moieties of interest are described in more detail below.

In specific embodiments, -W-L-Z of Formula I may be —$(CH_2)_m$—SH, —CO—$(CH_2)_n$—Br, or —$(CH_2)_o$—S—$CH_2$—CO—$CH_2$—Br, wherein m, n, and o are independently selected from 2 or 3.

Figure 2:
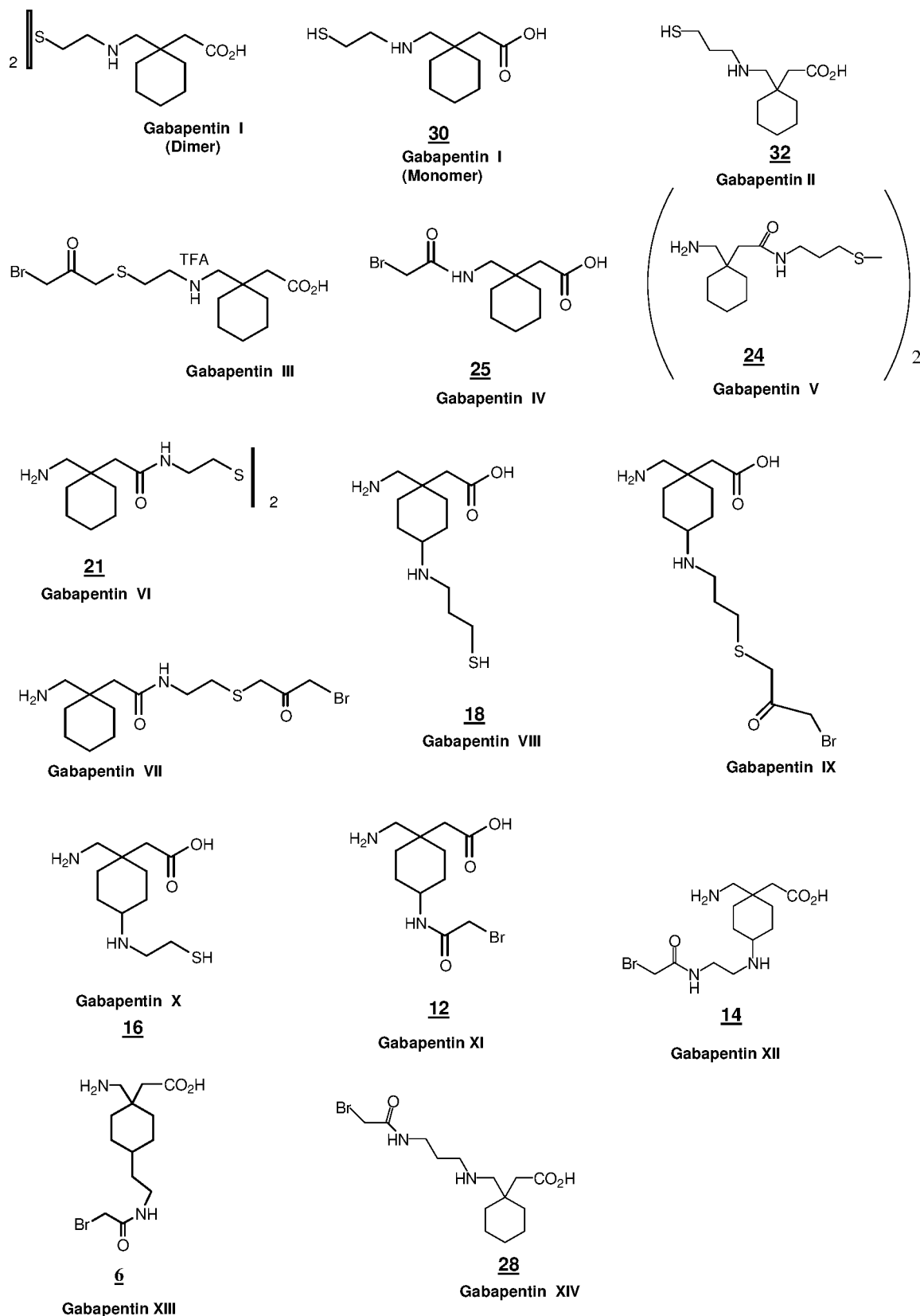
FIG. 2 is a schematic showing the structures of exemplary gabapentin derivatives.

Exemplary gabapentin derivatives of Formula I are provided in FIG. 2 as compounds Gabapentin I, II, III, IV, and XIV. In reduced gabapentin I, W and L are methyl and Z is SH (or may also be described per Formula I wherein L is a bond between W and Z, and W is ethyl). Gabapentin I may exist as a dimer forming a disulfide bond through the thiol groups as shown in FIG. 2. In gabapentin II, W is methyl, L is ethyl, and Z is SH. In gabapentin III, W is methyl, L is $(CH_2)SCH_2C(O)CH_2$, and Z is Br. In gabapentin IV, W is carbonyl, L is methyl, and Z is Br. In gabapentin XIV, W is methyl, L is —$(CH_2)_2NH$—$C(O)(CH_2)$—, and Z is Br.

Salts of gabapentin derivative of Formula I can be those as described above for Formula A.

Gabapetin Derivatives of Formula II

In another embodiment, gabapentin derivatives are characterized by an extension from the carbonyl group of gabapentin or its salt, which can be described by the formula:

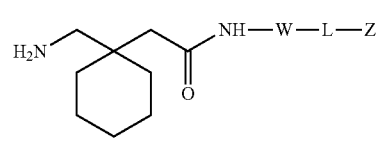

(II)

W, L, and Z can be as defined above in Formula A, and can be any combinations exemplified for Formula A as set out above. Accordingly, when W of Formula II is a lower alkyl group, W can be, for example, a straight, branched, or cyclic hydrocarbon chain containing 1 to 8 carbon atoms, from 1 to 6 carbon atoms, or from 1 to 4 carbon atoms. In general, when W of Formula A is a carbonyl group, then L is a linker, which can be, for example, a hydrocarbon chain of from 1 to 40 carbon atoms, or from 1 to 20 carbon atoms, or from 1 to 10 carbon atoms, which hydrocarbon chains may optionally contain ring structures (e.g., up to two ring structures) and one or more heteroatoms.

Where W is a lower alkyl exemplary linkers for gabapentin derivatives of Formula II include:
—$(CH_2)_nC(O)$—,
—$C(O)(CH_2)_n$—,
—$C(O)(CH_2)_nNH$—$C(O)$—,
—$C(O)(CH_2)_mNH$—$C(O)(CH_2)_n$—,
—$(CH_2)_nSCH_2C(O)$—,
—$(CH_2)_mSCH_2C(O)(CH_2)_n$—,
—$(CH_2)_mC(O)NH(CH_2)_n$—,
—$(CH_2)_nNH$—$C(O)$—,
—$(CH_2)_mNH$—$C(O)(CH_2)_n$—,
—$C(O)$—$(CH_2)_n$—, and
—$(CH_2)_n$—;
wherein m, n, o, and p are independently selected from an integer from 0 to 10, or from 1 to 10.

Where W is a carbonyl, exemplary linkers include:
—$(CH_2)_nC(O)$—,
—$(CH_2)_nSCH_2C(O)$—,
—$(CH_2)_mSCH_2C(O)(CH_2)_n$—,
—$(CH_2)_mC(O)NH(CH_2)_n$—,
—$(CH_2)_nNH$—$C(O)$—,
—$(CH_2)_mNH$—$C(O)(CH_2)_n$—, and
—$(CH_2)_n$—;

wherein m, n, o, and p are independently selected from an integer from 0 to 10, or from 1 to 10.

When Z of Formula A is a reactive functional group capable of reacting with a reactive partner to form a covalent bond, Z can be, for example a halogen (e.g., Br, Cl, I, and the like), OH, SH, $NH_2$, O-lower alkyl, epoxy, S-acyl, carboxyl, maleimidyl, haloacetamide, hydroxysuccinimidyl, succinimidyl, carbonate, anhydride, imidate, isocyanates, isothiocyanates, imidoesters, maleimides, thiolactones, diazonium groups, acrylamide, an acyl azide, an acyl nitrile, an alkyl halide, an aniline, an aryl halide, an azide, an aziridine, a boronate, a diazoalkane, a halotriazine, a hydrazine, a hydrazide, an imido ester, a phosphoramidite, a reactive platinum complex, a sulfonyl halide, and a photoactivatable group. Reactive functional groups for Z can be any of those as exemplified for Z of Formula A.

Moieties of interest for Z of Formula II include immunogenic carriers (e.g., carrier proteins) and detectable labels. Moieties of interest are described in more detail below.

In exemplary embodiments, -W-L-Z of Formula II may be —$(CH_2)_m$—SH, —CO—$(CH_2)_n$—Br, or —$(CH_2)_o$—S—$CH_2$—CO—$CH_2$—Br, wherein m, n, and o are independently selected from 2 or 3.

Exemplary gabapentin derivatives of Formula II are provided in FIG. 2. In reduced gabapentin V, W is methyl, L is ethyl and Z is SH. In reduced gabapentin VI, W and L are methyl and Z is SH. Gabapentin VI may be provided as a dimer forming a disulfide bond through the thiol groups. In gabapentin VII, W is methyl, L is $(CH_2)SCH_2C(O)CH_2$, and Z is Br.

Salts of gabapentin derivative of Formula II can be those as described above for Formula A.

Gabapetin Derivatives of Formula III

In a further embodiment the gabapentin derivatives are characterized as having an extension from carbon 4 of gabapentin. Such gabapentin derivatives can be described by the formula:

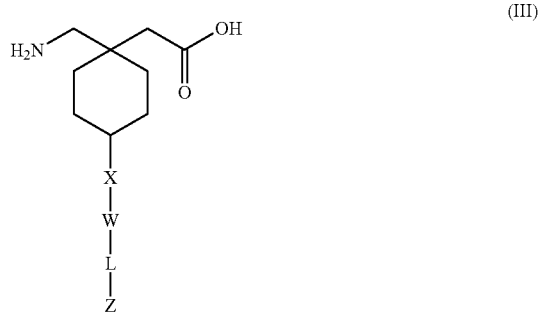

(III)

wherein X is a heteroatom or lower alkyl group. For example, X can be NH, S, SH, O, or OH. When X is a lower alkyl group, X can be, for example, a straight, branched, or cyclic hydrocarbon chain containing 1 to 8 carbon atoms, from 1 to 6 carbon atoms, or from 1 to 4 carbon atoms.

W, L, and Z of Formula III can be as defined above in Formula A, and can be any combinations exemplified for Formula A as set out above. Accordingly, when W of Formula III is a lower alkyl group, W can be, for example, a straight, branched, or cyclic hydrocarbon chain containing 1 to 8 carbon atoms, from 1 to 6 carbon atoms, or from 1 to 4 carbon atoms. In general, when W of Formula A is a carbonyl group, then L is a linker, which can be, for example, a hydrocarbon chain of from 1 to 40 carbon atoms, or from 1 to 20 carbon atoms, or from 1 to 10 carbon atoms, which hydrocarbon chains may optionally contain ring structures (e.g., up to two ring structures) and one or more heteroatoms.

Where W is a lower alkyl exemplary linkers for gabapentin derivatives of Formula III include:
—$(CH_2)_nC(O)$—,
—$C(O)(CH_2)_n$—,
—$C(O)(CH_2)_nNH$—C(O)—,
—$C(O)(CH_2)_mNH$—$C(O)(CH_2)_n$—,
—$(CH_2)_nSCH_2C(O)$—,
—$(CH_2)_mSCH_2C(O)(CH_2)_n$—,
—$(CH_2)_mC(O)NH(CH_2)_n$—,
—$(CH_2)_nNH$—C(O)—,
—$(CH_2)_mNH$—$C(O)(CH_2)_n$—,
—$C(O)$—$(CH_2)_n$—, and
—$(CH_2)_n$—;

wherein m, n, o, and p are independently selected from an integer from 0 to 10, or from 1 to 10.

Where W is a carbonyl, exemplary linkers include:
—$(CH_2)_nC(O)$—,
—$(CH_2)_nSCH_2C(O)$—,
—$(CH_2)_mSCH_2C(O)(CH_2)_n$—,
—$(CH_2)_mC(O)NH(CH_2)_n$—,
—$(CH_2)_nNH$—C(O)—,
—$(CH_2)_mNH$—$C(O)(CH_2)_n$—, and
—$(CH_2)_n$—;

wherein m, n, o, and p are independently selected from an integer from 0 to 10, or from 1 to 10.

When Z of Formula A is a reactive functional group capable of reacting with a reactive partner to form a covalent bond, Z can be, for example a halogen (e.g., Br, Cl, I, and the like), OH, SH, $NH_2$, O-lower alkyl, epoxy, S-acyl, carboxyl, maleimidyl, haloacetamide, hydroxysuccinimidyl, succinimidyl, carbonate, anhydride, imidate, isocyanates, isothiocyanates, imidoesters, maleimides, thiolactones, diazonium groups, acrylamide, an acyl azide, an acyl nitrile, an alkyl halide, an aniline, an aryl halide, an azide, an aziridine, a boronate, a diazoalkane, a halotriazine, a hydrazine, a hydrazide, an imido ester, a phosphoramidite, a reactive platinum complex, a sulfonyl halide, and a photoactivatable group. Reactive functional groups for Z can be any of those as exemplified for Z of Formula A. In specific embodiments, -W-L-Z of Formula III may be —$(CH_2)_m$—SH, —CO—$(CH_2)_n$—Br, or —$(CH_2)_o$—S—$CH_2$—CO—$CH_2$—Br, wherein m, n, and o are independently selected from 2 or 3.

Moieties of interest for Z of Formula III include immunogenic carriers (e.g., carrier proteins) and detectable labels. Moieties of interest are described in more detail below.

In exemplary gabapentin derivatives of Formula III, -X-W-L-Z may be —NH—$(CH_2)_m$—SH, —NH—CO—$(CH_2)_n$—Br, and —NH—$(CH_2)_o$—S—$CH_2$—CO—$CH_2$—Br, wherein m, n, and o are independently selected from 2 or 3.

Exemplary gabapentin derivatives of Formula III (gabapentin VIII, IX, X, XI, XII and XIII) are provided in FIG. 2. In reduced gabapentin VIII, X is NH, W is methyl, L is $(CH_2)_2$, and Z is SH. Gabapentin VIII may be provided as a dimer forming a disulfide bond through the thiol groups as shown in FIG. 2. In gabapentin IX, L is NH, W is methyl, L is $(CH_2)_2SCH_2C(O)CH_2$, and Z is Br. In gabapentin X, the moiety X is NH, W and L are methyl, and Z is SH. In gabapentin XI, X is NH, W is carbonyl, L is methyl, and Z is Br. In gabapentin XII, X is NH, W is methyl, L is —(CH$_2$)NH—C(O)(CH$_2$)—, and Z is Br. In gabapentin XIII, X and W are methyl, L is —NH—C(O)(CH$_2$)—, and Z is Br.

Salts of gabapentin derivative of Formula III can be those as described above for Formula A.

Methods of Making Gabapentin Derivatives

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention; it is not intended to define the scope of reactions or reaction sequences that are useful in preparing the compounds of the present invention.

In Schemes 1-5, preparatory schemes for 4-amino gabapentin derivatives (formula III) are presented.

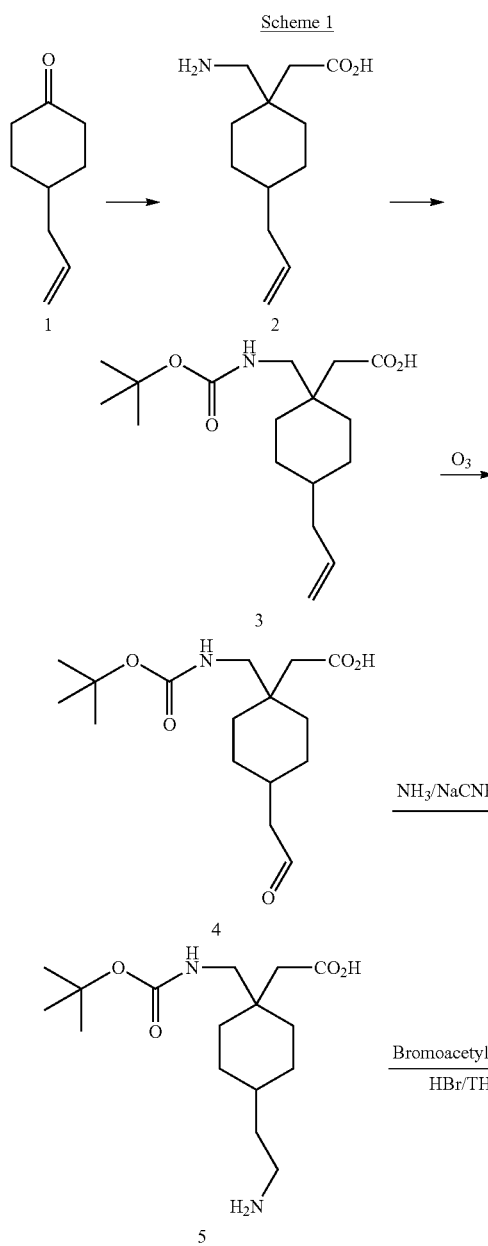

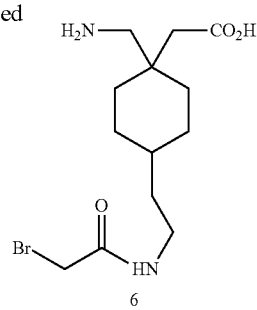

In scheme 1, compound 1 is reacted as described in the literature U.S. Pat. Publication No. 2007/0123591 and Chinese Pat. CN1740161, which are incorporated herein by reference, to form compound 2. In the next step of the reaction scheme, the amine of compound 2 is protected with an N-tert-butoxycarbonyl (t-BOC) protecting group to form compound 3. Compound 3 is then oxidized with ozone in an ozonolysis reaction to form the aldehyde compound 4. In the next step, compound 4 is reacted with ammonia (NH$_3$) and sodium cyanoborohydride (NaCNBH$_3$) to form amine compound 5. In the next step, compound 5 is bromoacetylated with bromo acetyl NHS ester, and then the t-BOC protecting group is removed with hydrogen bromide (HBr) to form compound 6, which is a 4-[2-(2-bromo-acetylamino)-ethyl] derivative of gabapentin.

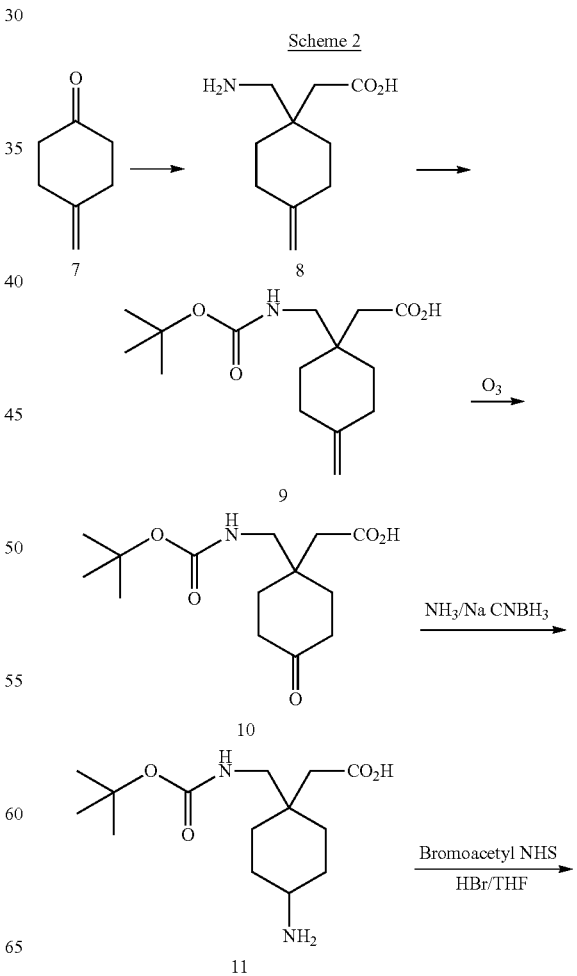

-continued

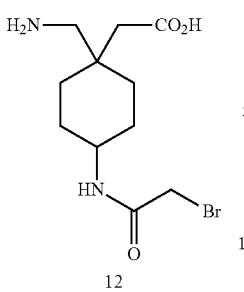
12

In Scheme 2, compound 7 is reacted as described in the literature U.S. Pat. Publication No. 2007/0123591 and Chinese Pat. CN1740161, which are incorporated herein by reference, to form compound 8. In the next step of the reaction scheme, the amine of compound 8 is protected with a t-BOC protecting group to form compound 9. Compound 9 is then oxidized with ozone in an ozonolysis reaction to form compound 10. In the next step, compound 10 is reacted with ammonia (NH₃) and sodium cyanoborohydride (NaCNBH₃) to form amine compound 11. In the next step, compound 11 is bromoacetylated with bromo acetyl NHS ester, and then the t-BOC protecting group is removed with hydrogen bromide (HBr) to form compound 12, which is a 4-(2-bromo-acetylamino) derivative of gabapentin.

Scheme 3

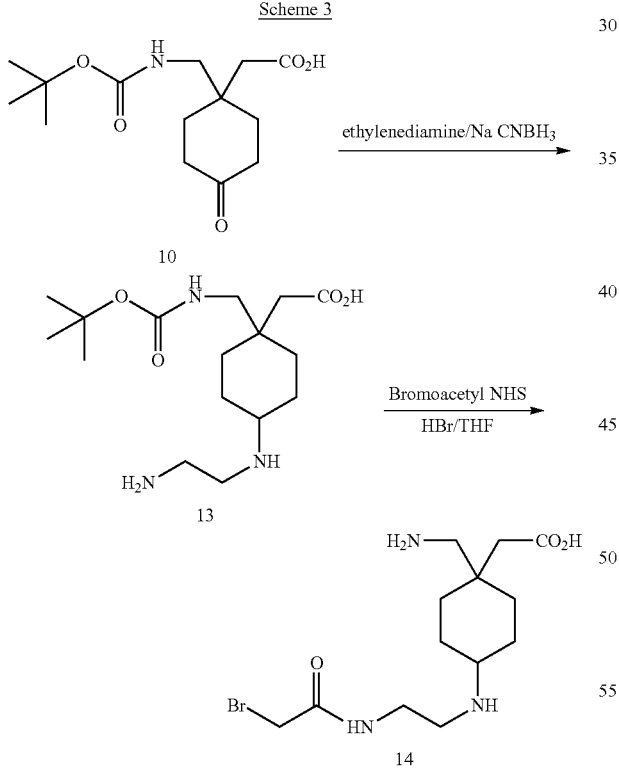

In Scheme 3, compound 10 is reacted with ethylenediamine and sodium cyanoborohydride (NaCNBH₃) to form amine compound 13. In the next step of the reaction scheme, compound 13 is bromoacetylated with bromo acetyl NHS ester, and then the t-BOC protecting group is removed with hydrogen bromide (HBr) to form compound 14, which is a 4-[2-(2-bromo-acetylamino)-ethylamino] derivative of gabapentin.

Scheme 4

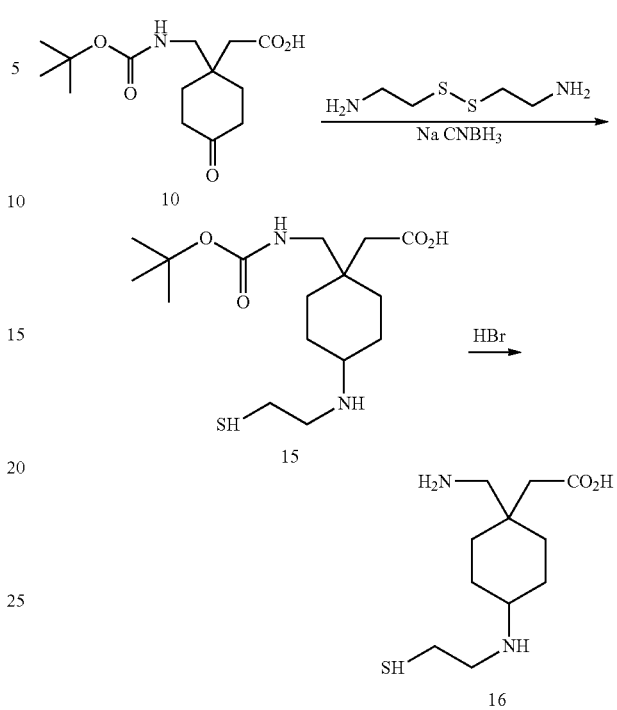

In Scheme 4, compound 10 is reacted with 2-(2-Aminoethyldisulfanyl)-ethylamine and sodium cyanoborohydride (NaCNBH₃) to form amine compound 15. In the next step of the reaction scheme, the t-BOC protecting group of compound 15 is removed with hydrogen bromide (HBr) to form compound 16, which is a 4-(2-mercapto-ethylamino) derivative of gabapentin.

Scheme 5

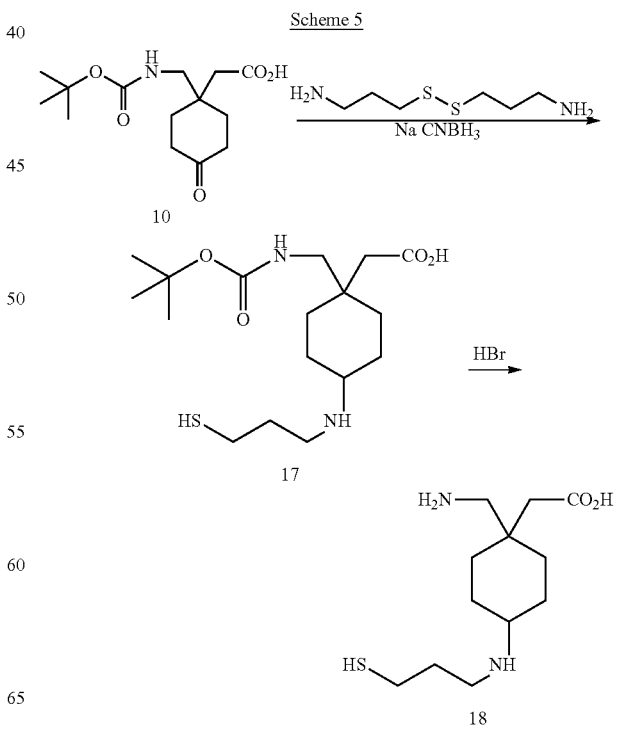

In Scheme 5, compound 10 is reacted with 3-(3-Aminopropyldisulfanyl)-propylamine and sodium cyanoborohydride (NaCNBH₃) to form amine compound 17. In the next step of the reaction scheme, the t-BOC protecting group of compound 17 is removed with hydrogen bromide (HBr) to form compound 18, which is a 4-(3-mercapto-propylamino) derivative of gabapentin.

In Schemes 6-7, preparatory schemes for carboxyl modified derivatives of gabapentin (formula II) are presented.

In Scheme 7, compound 19 is reacted with 3-(3-Aminopropyldisulfanyl)-propylamine to form compound 23. In the next step of the reaction scheme, compound 23 is deprotected with HCl to from compound 24, which is a carboxyl modified derivative of gabapentin.

In Schemes 8-11, preparatory schemes for amine modified derivatives of gabapentin are presented.

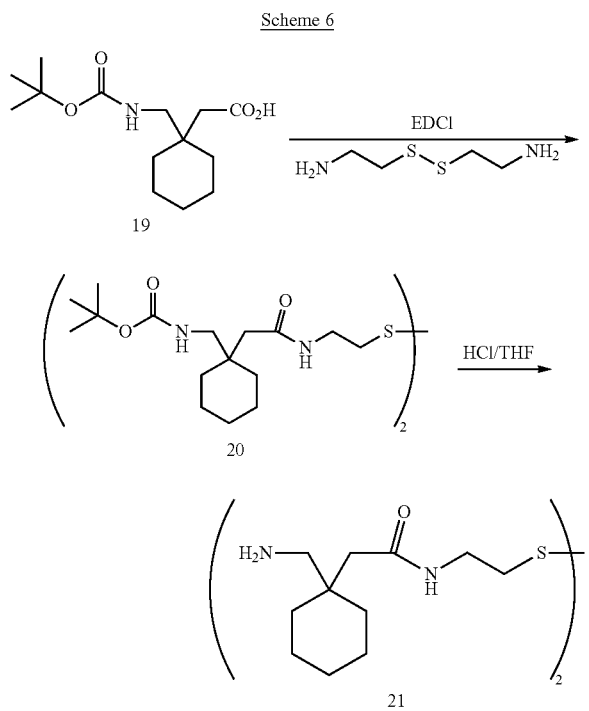

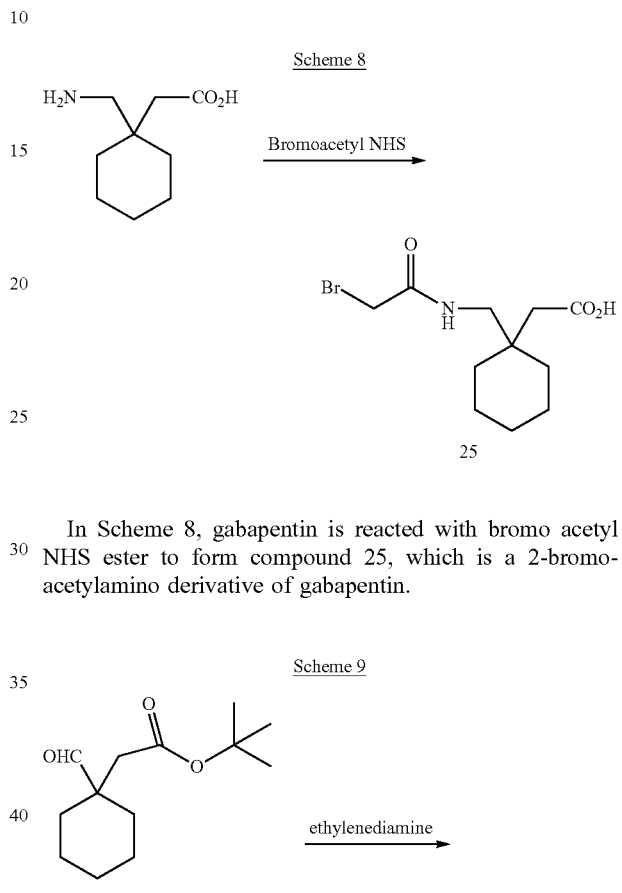

In Scheme 6, compound 19 is reacted with 2-(2-Aminoethyldisulfanyl)-ethylamine to form compound 20. In the next step of the reaction scheme, compound 20 is deprotected with HCl to from compound 21, which is a carboxyl modified derivative of gabapentin.

In Scheme 8, gabapentin is reacted with bromo acetyl NHS ester to form compound 25, which is a 2-bromoacetylamino derivative of gabapentin.

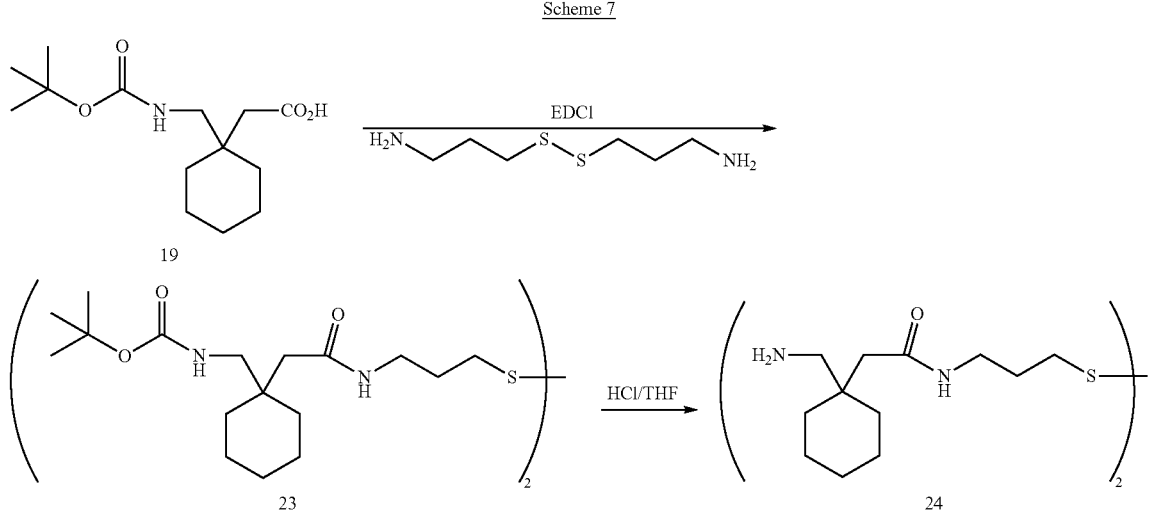

Scheme 9 (continued)

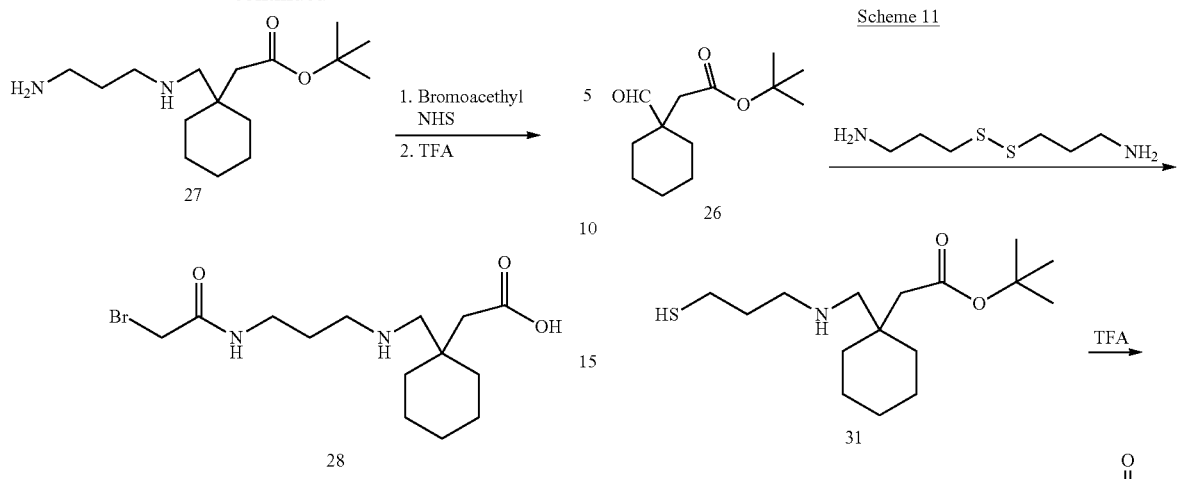

In Scheme 9, compound 26 is reacted with ethylenediamine to form amine compound 27. In the next step of the reaction scheme, compound 27 is reacted with bromoacetyl NHS ester to form a t-butyl ester intermediate (not shown), which is subsequently deprotected with trifluoroacetic acid (TFA) to form compound 28, which is a 3-(2-bromo-acetylamino)-propylamino derivative of gabapentin.

Scheme 10

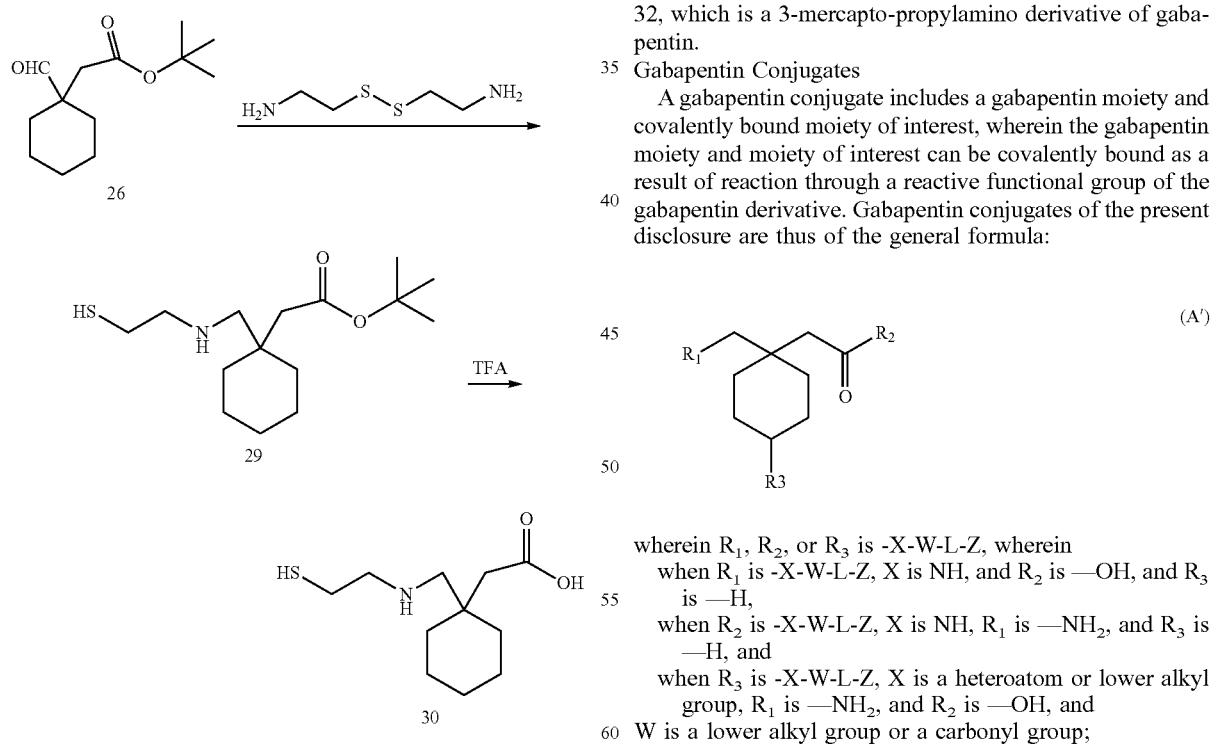

In Scheme 10, compound 26 is reacted with 2-(2-Aminoethyldisulfanyl)-ethylamine to form the t-butyl ester compound 29. In the next step of the reaction scheme, compound 29 is deprotected with TFA to form compound 30, which is a 2-mercapto-ethylamino derivative of gabapentin.

Scheme 11

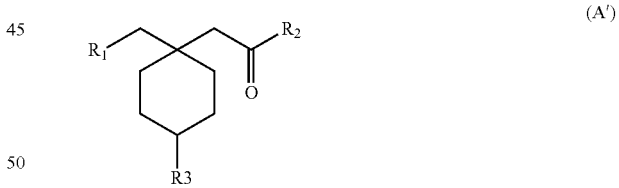

In Scheme 11, compound 26 is reacted with 3-(3-Aminopropyldisulfanyl)-propylamine to form the t-butyl ester compound 31. In the next step of the reaction scheme, compound 31 is deprotected with TFA to form compound 32, which is a 3-mercapto-propylamino derivative of gabapentin.

Gabapentin Conjugates

A gabapentin conjugate includes a gabapentin moiety and covalently bound moiety of interest, wherein the gabapentin moiety and moiety of interest can be covalently bound as a result of reaction through a reactive functional group of the gabapentin derivative. Gabapentin conjugates of the present disclosure are thus of the general formula:

(A')

wherein $R_1$, $R_2$, or $R_3$ is -X-W-L-Z, wherein
when $R_1$ is -X-W-L-Z, X is NH, and $R_2$ is —OH, and $R_3$ is —H,
when $R_2$ is -X-W-L-Z, X is NH, $R_1$ is —$NH_2$, and $R_3$ is —H, and
when $R_3$ is -X-W-L-Z, X is a heteroatom or lower alkyl group, $R_1$ is —$NH_2$, and $R_2$ is —OH, and
W is a lower alkyl group or a carbonyl group;
L is a linker or at least one bond between W and Z; and
Z is a moiety of interest (e.g., an immunogenic carrier or detectable label);
or a salt thereof.

Accordingly, when W of Formula A' is a lower alkyl group, W can be, for example, a straight, branched, or cyclic hydrocarbon chain containing 1 to 8 carbon atoms, from 1 to 6 carbon atoms, or from 1 to 4 carbon atoms. In general, when W of Formula A' is a carbonyl group, then L is a linker, which can be, for example, a hydrocarbon chain of from 1 to 40 carbon atoms, or from 1 to 20 carbon atoms, or from 1 to 10 carbon atoms, which hydrocarbon chains may optionally contain ring structures (e.g., up to two ring structures) and one or more heteroatoms.

Where W is a lower alkyl exemplary linkers for gabapentin derivatives of Formula A' include:

—(CH$_2$)$_n$C(O)—,
—C(O)(CH$_2$)$_n$—,
—C(O)(CH$_2$)$_n$NH—C(O)—,
—C(O)(CH$_2$)$_m$NH—C(O)(CH$_2$)$_n$—,
—(CH$_2$)$_n$SCH$_2$C(O)—,
—(CH$_2$)$_m$SCH$_2$C(O)(CH$_2$)$_n$—,
—(CH$_2$)$_m$C(O)NH(CH$_2$)$_n$—,
—(CH$_2$)$_n$NH—C(O)—,
—(CH$_2$)$_m$NH—C(O)(CH$_2$)$_n$—,
—C(O)—(CH$_2$)$_n$—, and
—(CH$_2$)$_n$—;

wherein m, n, o, and p are independently selected from an integer from 0 to 10, or from 1 to 10.

Where W is a carbonyl, exemplary linkers include:

—(CH$_2$)$_n$C(O)—,
—(CH$_2$)$_n$SCH$_2$C(O)—,
—(CH$_2$)$_m$SCH$_2$C(O)(CH$_2$)$_n$—,
—(CH$_2$)$_m$C(O)NH(CH$_2$)$_n$—,
—(CH$_2$)$_n$NH—C(O)—,
—(CH$_2$)$_m$NH—C(O)(CH$_2$)$_n$—, and
—(CH$_2$)$_n$—;

wherein m, n, o, and p are independently selected from an integer from 0 to 10, or from 1 to 10.

Salts of gabapentin derivatives include, but are not necessarily limited to, alkali metal salts, such as (sodium salts, potassium salts, magnesium salts), halide salts (e.g., bromo, chloro, and the like); acetate salts (e.g., salts with trifluoroacetic acid, and the like).

In one embodiment, the moiety of interest is bound to a gabapentin conjugate through a linker selected from CONH, NHCO, NHCONH, NH—(C=S)—NH, O—CO—NH, NH—O—CO, S, NH—(C=NH), N=N, or NH.

The present disclosure also provides gabapentin conjugates of the formula:

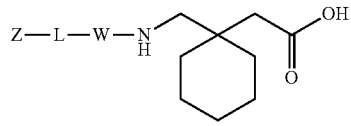

(I')

wherein W and L are as defined in Formula A', and Z is a moiety of interest.

Accordingly, exemplary linkers for gabapentin conjugates of Formula I' are as listed above in Formula A'. Salts of gabapentin conjugate of Formula A' can include those as described for Formula A'.

Figure 3:
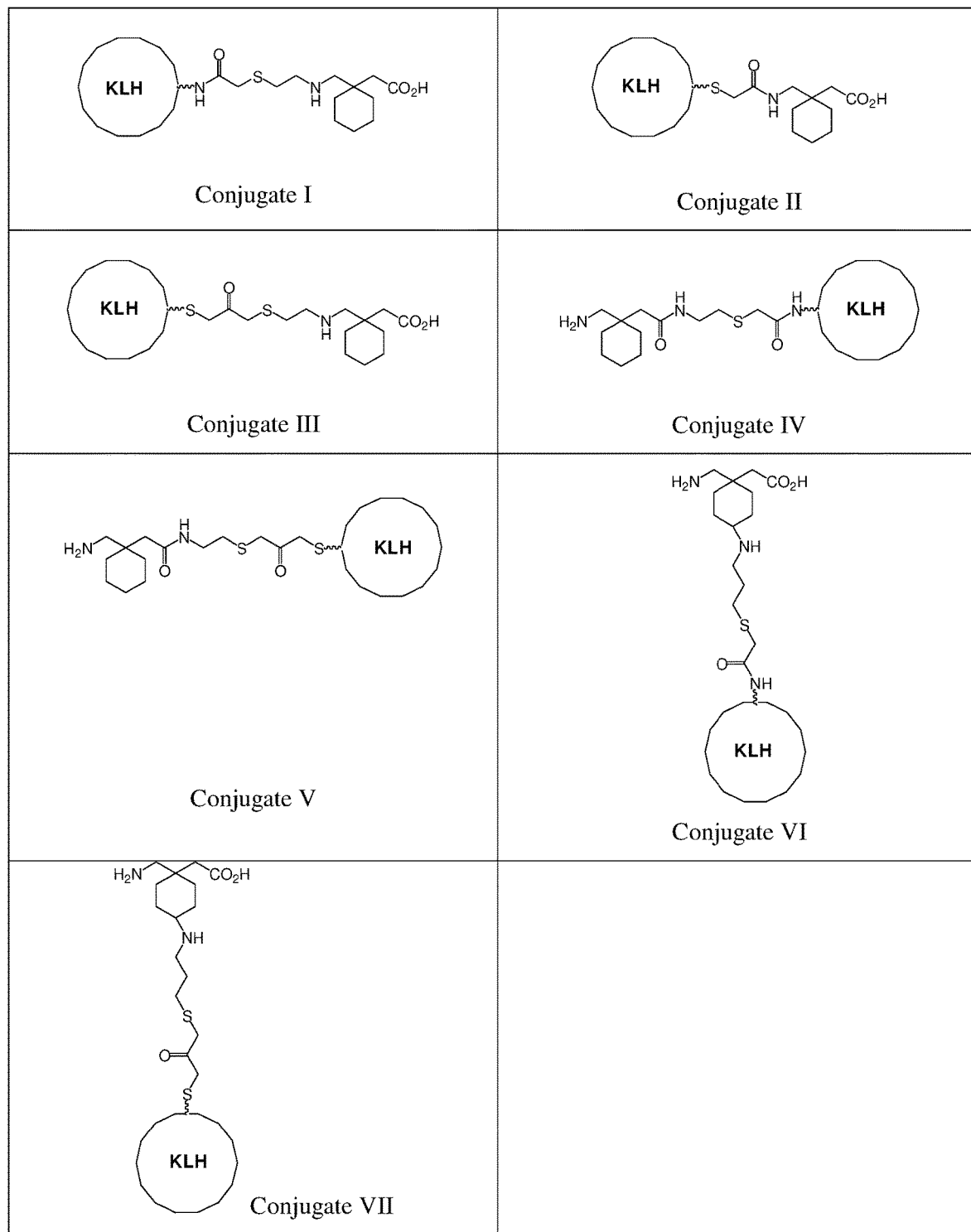
FIG. 3 is a schematic showing the structures of exemplary gabapentin conjugates comprising an exemplary protein carrier.

Exemplary gabapentin conjugates of Formula I' are provided in FIG. 3 as Conjugates I, II, and III. In Conjugate I W is a lower alkyl (e.g., (CH$_2$)$_2$), and L is —S—(CH$_2$)(C=O)— which is joined to a carrier protein (Z) through an amine of an amino acid residue of the protein (exemplified by keyhole limpet hemocyanin (KLH)). In Conjugate II, W is a carbonyl, L is a methyl group, and Z is a carrier protein (exemplified by KLH) which is attached to the gabapentin moiety through a sulfhydryl group of a cysteine residue of the protein. In Conjugate III, W is a lower alkyl (e.g., (CH$_2$)$_2$), and L is —S—(CH$_2$)(C=O)(CH$_2$)—, and Z is a carrier protein (e.g., KLH) which is attached to the gabapentin moiety through a sulfhydryl group of a cysteine residue of the protein.

In another embodiment, gabapentin conjugates are characterized by an extension from the carbonyl group of gabapentin, which can be described by the formula:

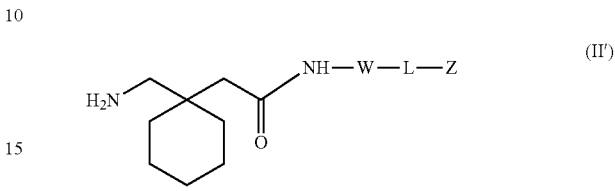

(II')

wherein W and L are as defined in Formula A', and Z is a moiety of interest.

Accordingly, exemplary linkers for gabapentin conjugates of Formula II' are as listed above in Formula A'. Salts of gabapentin conjugates of Formula II' can be those as described above for Formula A'.

Exemplary gabapentin conjugates of Formula II' are provided in FIG. 3 as Conjugates IV and V. In Conjugate IV, W is a lower alkyl (e.g., (CH$_2$)$_2$), L is —S—(CH$_2$) (C=O)—, and Z is exemplified by a carrier protein (e.g., KLH) which is linked to the gabapentin moiety through an amine of an amino acid residue of the protein. In Conjugate V, W is a lower alkyl (e.g., (CH$_2$)$_2$), L is —S—(CH$_2$)(C=O)(CH$_2$)—, and Z is exemplified by a carrier protein (e.g., KLH) which is linked to the gabapentin moiety through a sulfhydryl of a cysteine residue of the protein.

In a further embodiment the gabapentin conjugates are characterized as having an extension from carbon 4 of gabapentin. Such gabapentin conjugates can be described by the formula:

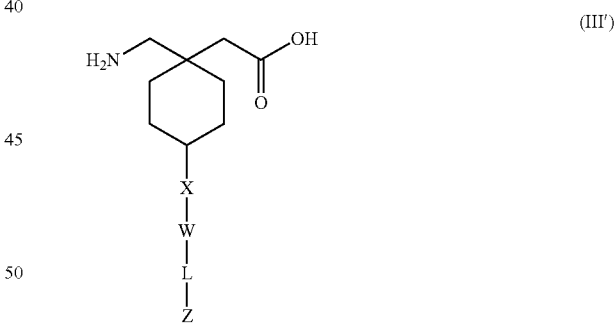

(III')

wherein X is a heteroatom or lower alkyl group, W and L are as defined in Formula A'.

Accordingly, exemplary linkers for gabapentin conjugates of Formula III' are as listed above in Formula A'. Salts of gabapentin conjugates of Formula III' can be those as described above for Formula A'.

Exemplary gabapentin conjugates of Formula III' are provided in FIG. 3 as Conjugates Vi and VII. In Conjugate VI, W is a lower alkyl (e.g., —(CH$_2$)$_3$—), L is —S—(CH$_2$) (C=O)—, and Z is exemplified by a carrier protein (e.g., KLH) which is linked to the gabapentin moiety through an amine of an amino acid residue of the protein. In Conjugate VII, W is a lower alkyl (e.g., —(CH$_2$)$_3$—), L is —S—(CH$_2$) (C=O)(CH$_2$)—, and Z is exemplified by a carrier protein (e.g., KLH) which is linked to the gabapentin moiety through a sulfhydryl of a cysteine residue of the protein.

Where the moiety of interest has multiple available covalent attachment sites for a gabapentin moiety (e.g., a reactive partner having multiple reaction sites for reaction with a gabapentin derivative), the gabapentin conjugate can include more than one gabapentin moiety. Accordingly, gabapentin conjugates of the present disclosure include those in which two or more, gabapentin moieties are bound to the same moiety of interest (e.g., polypeptide (e.g., carrier protein), solid support (e.g., Sepharose® bead, particle (e.g., gold particle, magnetic particle). Such gabapentin conjugates can thus be represented by a formula as follows:

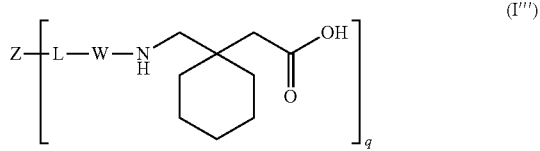

wherein W and L are as defined in Formula A', and Z is a moiety of interest having two or more attachment sites for a gabapentin moiety;

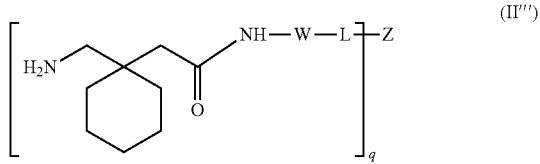

wherein W and L are as defined in Formula A', and Z is a moiety of interest having two or more attachment sites for a gabapentin moiety; or

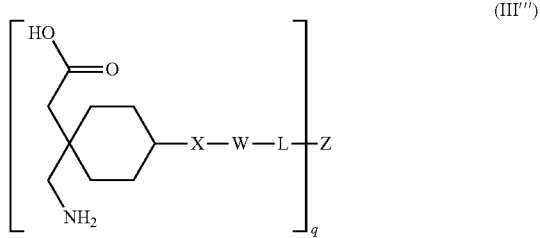

wherein X is a heteroatom or lower alkyl group, W and L are as defined in Formula A', and wherein q is at least 1, and may be 2 or more, 5 or more, or 10 or more, 15 or more, up to a number of reaction sites available on Z. For example, where Z is a polypeptide, q can be up to the number of accessible amino acid residues reactive with a gabapentin derivative having an appropriate reactive functional group.

Moieties of Interest of Gabapentin Conjugates

In general, the moiety of interest of gabapentin conjugates of the present disclosure can be any suitable chemical entity or support, especially one adapted for use in an assay, or for generating reagents useful in such assays (e.g., anti-gabapentin antibody production), described herein.

Accordingly, the moiety of interest can be, for example, an immunogenic carrier, a detectable label, or a support.

Exemplary immunogenic carriers include polypeptides (which term is used to encompass amino acid chains of any length, including peptides and proteins), modified polypeptides (e.g., post-translationally and/or chemically modified, e.g., lipoproteins, glycoproteins, and the like), and polysaccharides, with polypeptide immunogenic carriers being of particular interest.

Further exemplary moieties of interest, which may serve as detectable labels, include polypeptides having an immunodetectable epitope (i.e., detectable by binding of a binding partner that specifically binds the epitope (e.g., an HA tag)), nucleic acids (which can be detectable by use of a hybridization probe or by PCR-based methods), radioactive isotopes, enzymes (including enzyme fragments, enzyme donor fragments, enzyme acceptor fragments, coenzymes), enzyme ligands (e.g., enzyme substrates, enzyme inhibitors), fluorescent moieties (including fluorophores and quenchers), phosphorescent moieties, anti-stokes up-regulating moieties, chemiluminescent moieties, luminescent moieties, chromophores, radioactive isotopes, and combinations thereof.

Further exemplary moieties of interest which may serve as a support include, but are not necessarily limited to, solid supports (e.g., arrays), particles (including gold particles, microparticles, magnetic particles, beads, and the like), and liposomes.

As noted above, a "detectable label" generally refers to an identifying tag that can provide for a detectable signal, e.g., luminescence (e.g., photoluminescence (e.g., fluorescence, phosphorescence), chemoluminescence (e.g., bioluminescence)), radioactivity, immunodetection, enzymatic activity, and the like). Examples of a label include a polypeptide such as an antigen, enzyme, an antibody, a nucleic acid, a fluorophor, a quencher (e.g., of a FRET pair), a phosphorescent group, a chemiluminescent group, a chromophoric group, an electrochemically active group, an electrochemiluminescent group, a group that undergoes a change in fluorescence, phosphorescence, chemiluminescence or electrochemical property upon binding (U.S. Pat. Nos. 6,203,974 and 6,159,750), a solid particle, a gold particle, a radioactive isotope, an enzyme ligand (e.g., an enzyme inhibitor, an enzyme substrate), an enzyme cofactor, a member of an enzyme donor-acceptor pair.

The detectable label can be a non-isotopic signal-generating moiety." "Non-isotopic signal-generating moiety", as used herein, refers to a moiety that does not emit radioactivity as a detectable signal. By way of example, a non-isotopic signal-generating moiety is an enzyme, fluorescent compound, or a luminescent compound.

Exemplary moieties of interest are further described below.

Gabapentin-Carrier Protein Conjugates

In one embodiment, the moiety of interest is an immunogenic carrier, particularly an immunogenic carrier protein. Such gabapentin conjugates find use in production of anti-gabapentin antibodies, which in turn find use in the gabapentin detection assays described herein. Exemplary carriers include, but are not necessarily limited to, proteins, glycoproteins, complex polysaccharides, particles, and nucleic acids that are recognized as foreign and thereby elicit an immunologic response from the host.

Various protein types may be employed as a poly(amino acid) immunogenic carrier. These types include albumins, serum proteins, e.g., globulins, ocular lens proteins, lipoproteins, etc. Illustrative proteins include bovine serum albumin (BSA), keyhole limpet hemocyanin (KLH), egg ovalbumin, bovine gamma-globulin (BGG), etc. Immunogenic polypeptides include genetically-encodable and synthetic polypeptides.

The immunogenic carrier can also be a polysaccharide, which is a high molecular weight polymer built up by repeated condensations of monosaccharides. Examples of polysaccharides are starches, glycogen, cellulose, carbohydrate gums such as gum arabic, agar, and so forth. The polysaccharide can also contain polyamino acid residues and/or lipid residues.

The immunogenic carrier can also be a poly(nucleic acid) either alone or conjugated to one of the above mentioned poly(amino acids) or polysaccharides. The immunogenic carrier can also be a particle. The particles are generally at least about 0.02 microns and not more than about 100 micron, and usually about 0.05 micron to 10 micron in diameter. The particle can be organic or inorganic, swellable or non-swellable, porous or non-porous, optionally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli*, and viruses. The particles can also be comprised of organic and inorganic polymers, liposomes, latex, phospholipid vesicles, or lipoproteins.

Immunogenic carriers exemplified herein include keyhole limpet hemocyanin (KLH) and bovine serum albumin (BSA). FIG. 3 shows schematic representation of exemplary gabapentin conjugates having a gabapentin moiety linked to KLH. Dimerized gabapentin conjugates can be linked through a disulfide bond, which may be reduced to generate monomeric gabapentin conjugates, e.g., by reaction with DTT or TCEP. Gabapentin carrier protein conjugates may comprise a plurality of gabapentin derivatives covalently bonded to the protein carrier, as discussed in Formulae I''', II''', and III''' above.

Gabapentin-Enzyme Conjugates

In another embodiment, the moiety of interest of the gabapentin conjugate is an enzyme. In general, the enzyme can serve as a non-isotopic signal generating moiety, and may be any enzyme that provides for a detectable signal useful in, for example, an immunoassay described herein. Exemplary enzymes include alkaline phosphatase, ß-galactosidase, horse radish peroxidase, glucose-6-phosphate dehydrogenase (G6PDH), and the like. The G6PDH refers to both a naturally occurring G6PDH and G6PDH variants that contain one or more cysteine residues non-native to naturally-occurring G6PDH.

In one embodiment of interest, gabapentin enzyme conjugates provide an immunoassay reagent that compete with gabapentin that may be present in a sample for binding to an anti-gabapentin antibody, wherein the presence of absence of a detectable signal provided by the enzyme is indicative of the presence or absence of a gabapentin-anti-gabapentin antibody complex. Gabapentin enzyme conjugates containing G6PDH (including naturally occurring G6PDH and G6PDH variants, particularly G6PDH cysteine variants) find particular use in such assays.

Figure 4:
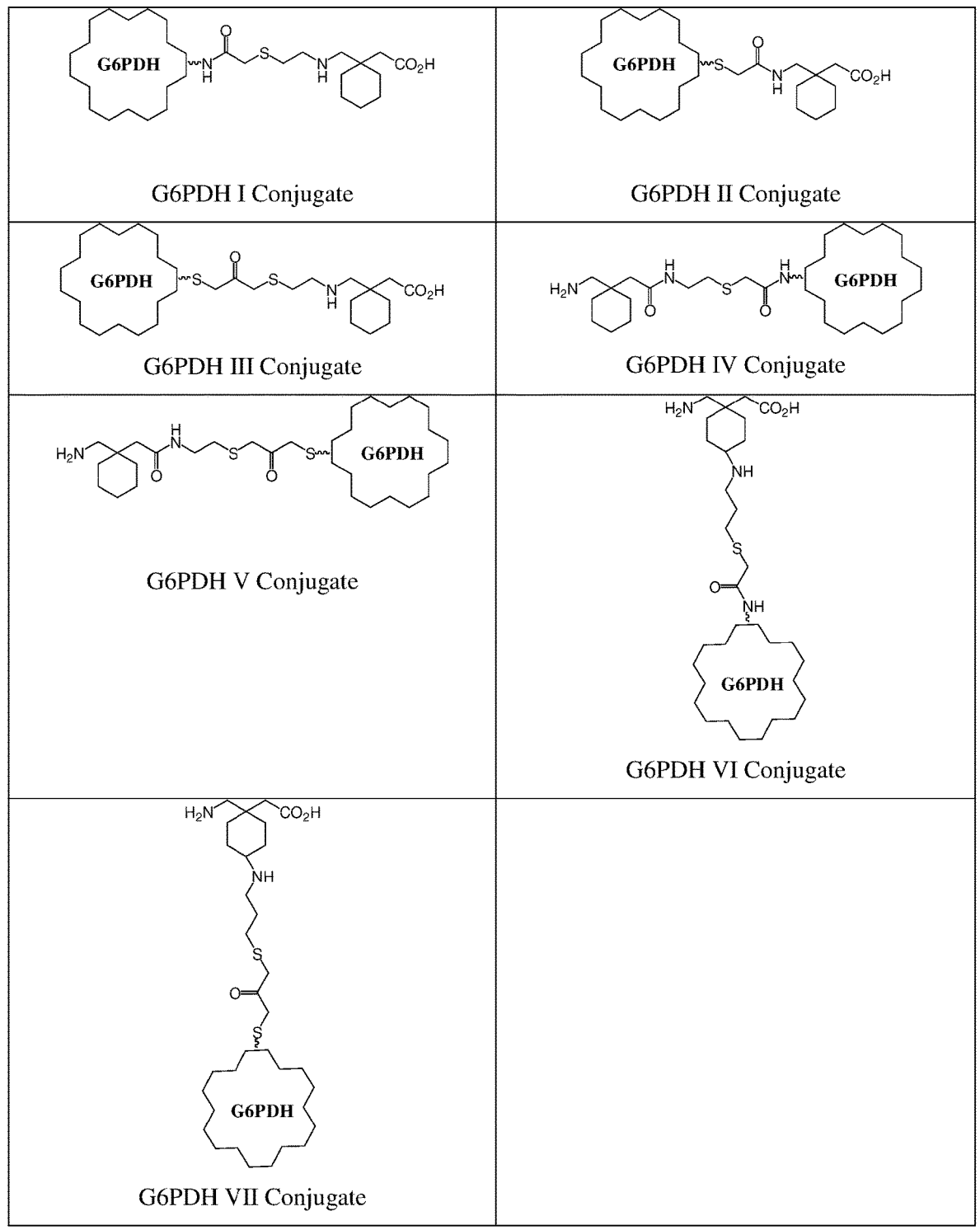
FIG. 4 is a schematic showing the structures of seven exemplary gabapentin conjugates comprising an exemplary enzyme.

FIG. 4 shows schematic representation of exemplary gabapentin enzyme conjugates, exemplified by gabapentin G6PDH conjugates. Dimerized gabapentin enzyme conjugates can be linked through a disulfide bond, which may be reduced to generate monomeric gabapentin enzyme conjugates, e.g., by reaction with DTT or TCEP. Gabapentin enzyme conjugates may comprise a plurality of gabapentin derivatives covalently bonded to the protein carrier, as discussed in Formulae I''', II''', and III''' above.

Other Gabapentin Conjugates

The moiety of interest may be a support, thus immobilizing the gabapentin conjugate. The moiety of interest may provide a detectable signal, such as a fluorophore, a fluorescence quencher, a radioisotope, and metal particle (e.g., in SERS-based assays). Gabapentin conjugates can include, for example, a first member of a FRET pair (e.g., a member of a fluorophore/quencher pair), where the gabapentin conjugate is used in connection with an anti-gabapentin antibody having the second member of the FRET pair, such that binding of the labeled anti-gabapentin antibody to the labeled gabapentin conjugate in a complex provides for a detectable signal different from that when the labeled anti-gabapentin antibody and labeled gabapentin conjugate are not in a complex with one another (e.g., as when binding of gabapentin blocks binding of the antibody to the gabapentin conjugate).

Methods of Making Gabapentin Conjugates

Gabapentin conjugates are typically prepared by synthesizing a gabapentin derivative having a reactive functional group (e.g., as described above), and incubating the gabapentin derivative with a reactive partner (e.g., a protein) under conditions that permit a conjugation reaction to occur, and then separating the conjugate from the reaction mixture.

For example, a protein conjugate can be prepared by combining an excess of a bromoacetyl adduct with a protein having free thiol groups as described in U.S. Pat. No. 6,455,288. Free sulfhydryls may be provided in the form of free cysteine residues or by reducing protein disulfide bonds by a reagent such as dithiothreitol. Alternatively, thiol groups can be added to a protein having free primary amino groups by reacting with 2-iminothiolane (IT) in aqueous buffer, followed by removal of unreacted IT. A detailed protocol for the thiolation of the protein KLH is provided in U.S. Pat. No. 5,439,798.

Figure 7A:
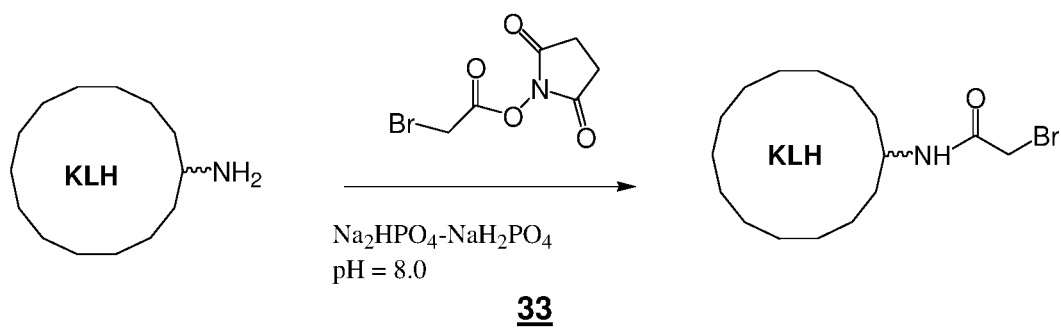
FIGS. 7A and 7B are schematic representations of preparation of reactive forms of KLH and an enzyme.
Figure 7A:
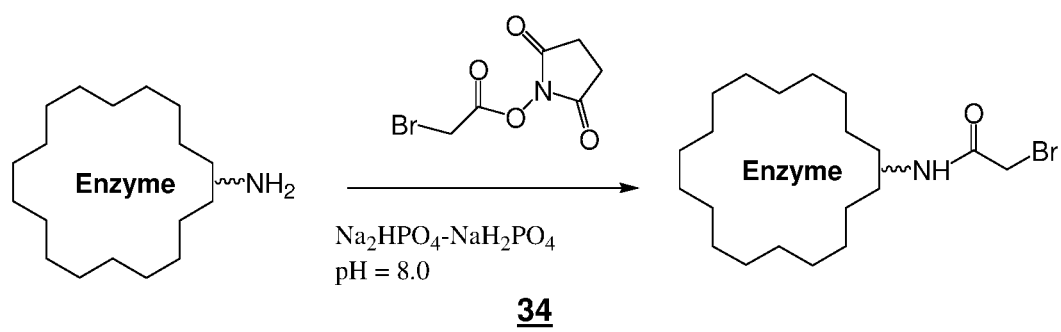
Figure 7B:
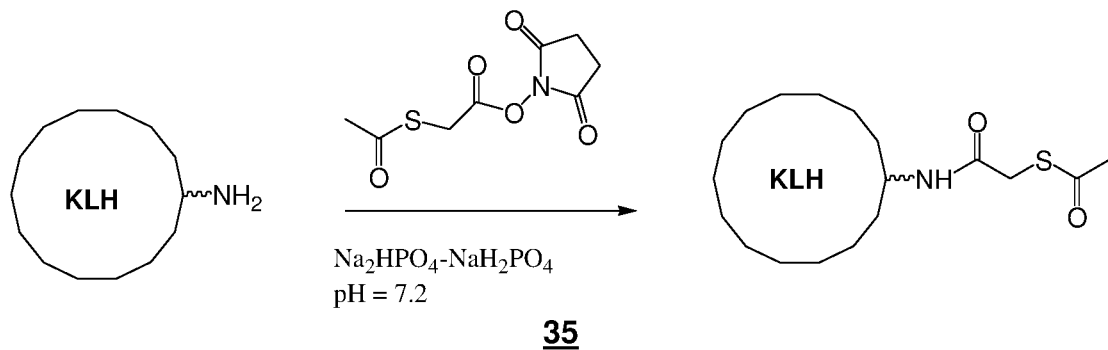
Figure 7B:
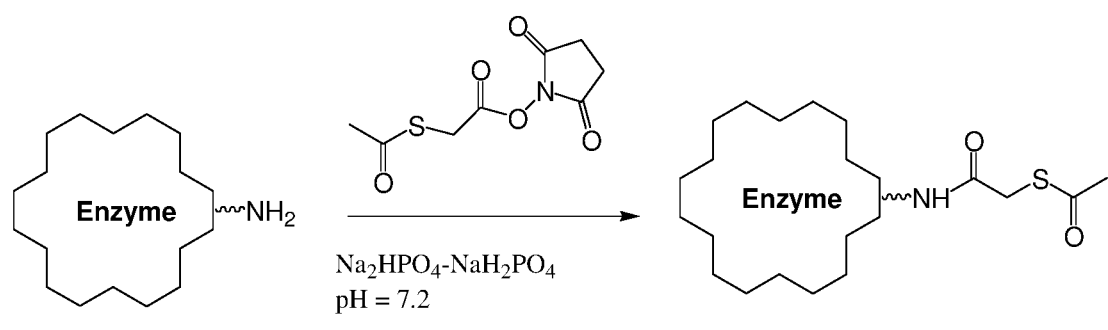
Figure 8A:
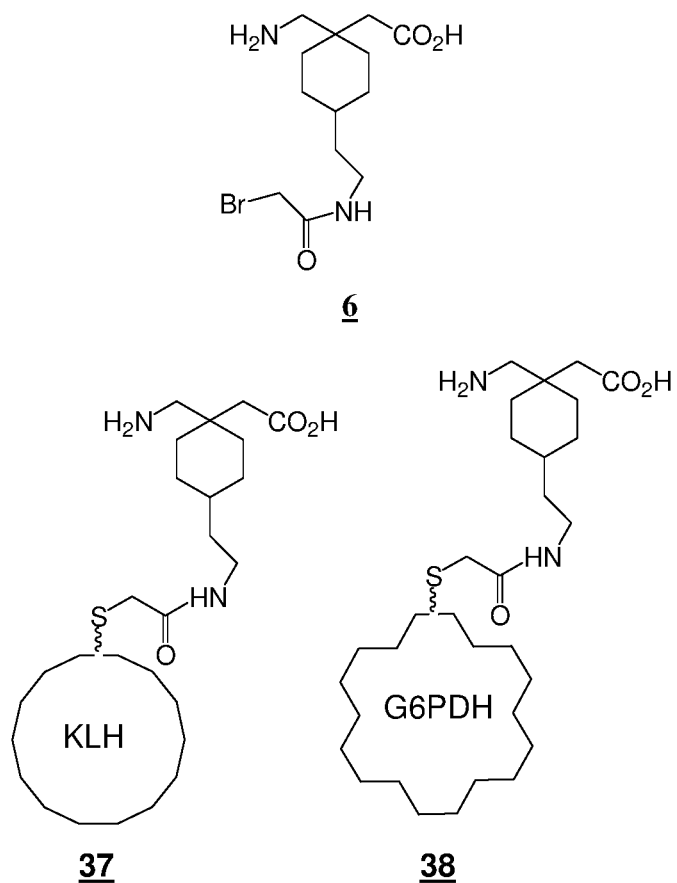
FIGS. 8A-K are schematic representations of synthetic schemes of exemplary gabapentin conjugates.
Figure 8B:
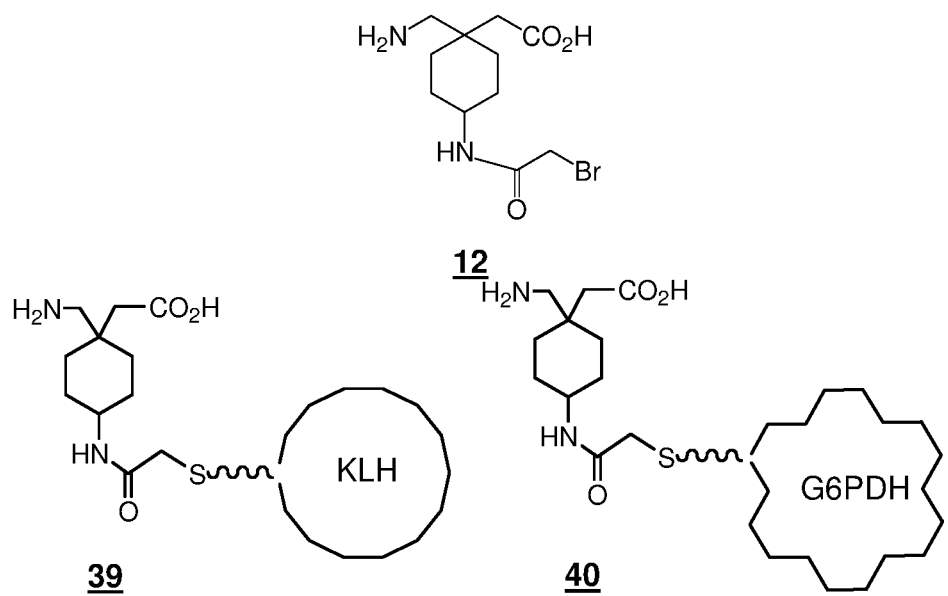
Figure 8C:
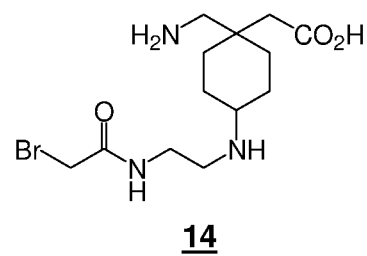
Figure 8C:
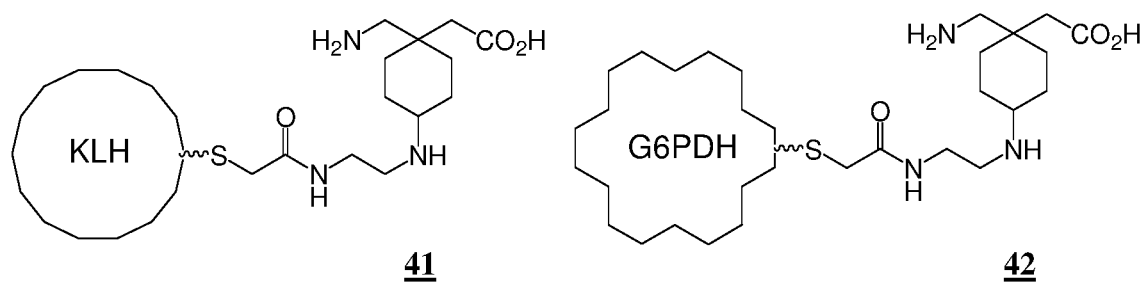
Figure 8D:
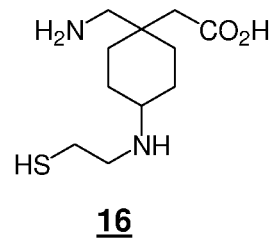
Figure 8D:
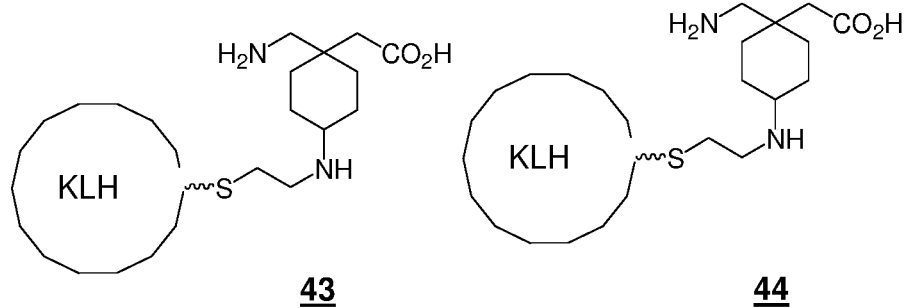
Figure 8E:
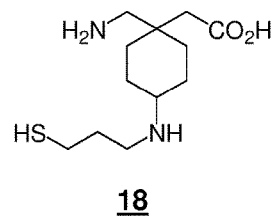
Figure 8E:
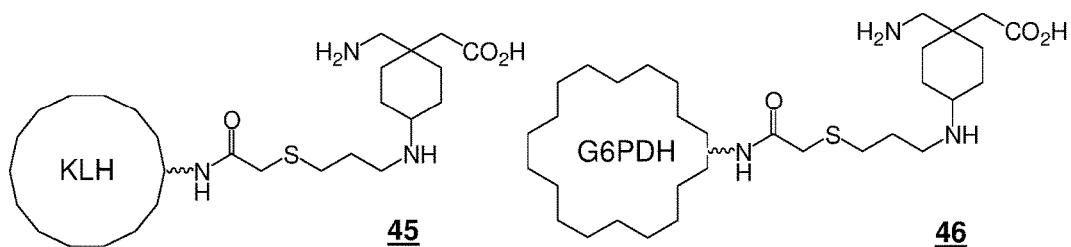
Figure 8F:
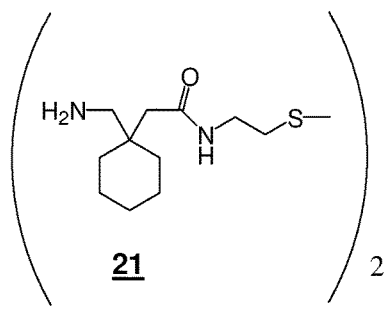
Figure 8F:
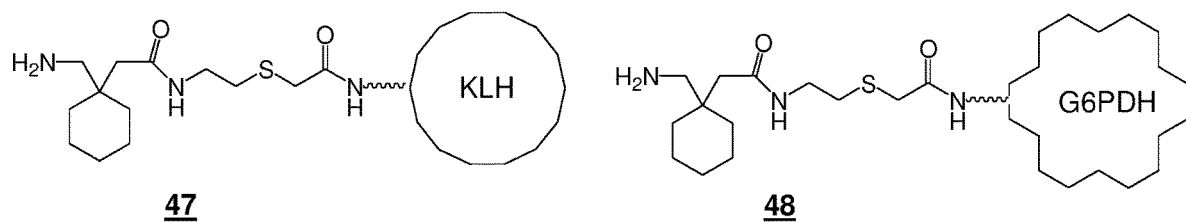
Figure 8G:
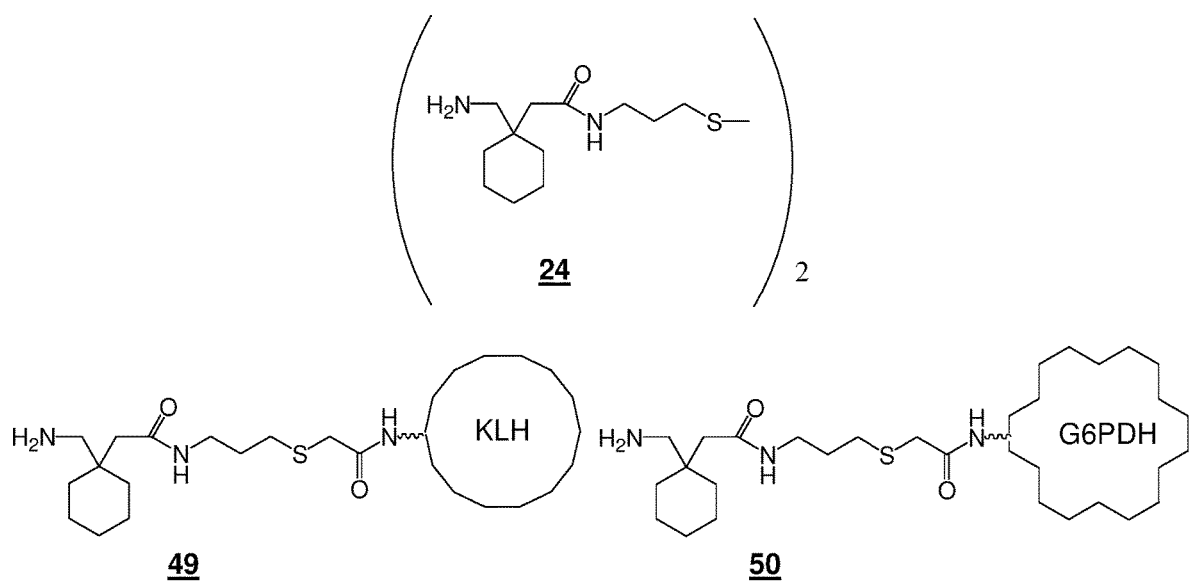
Figure 8H:
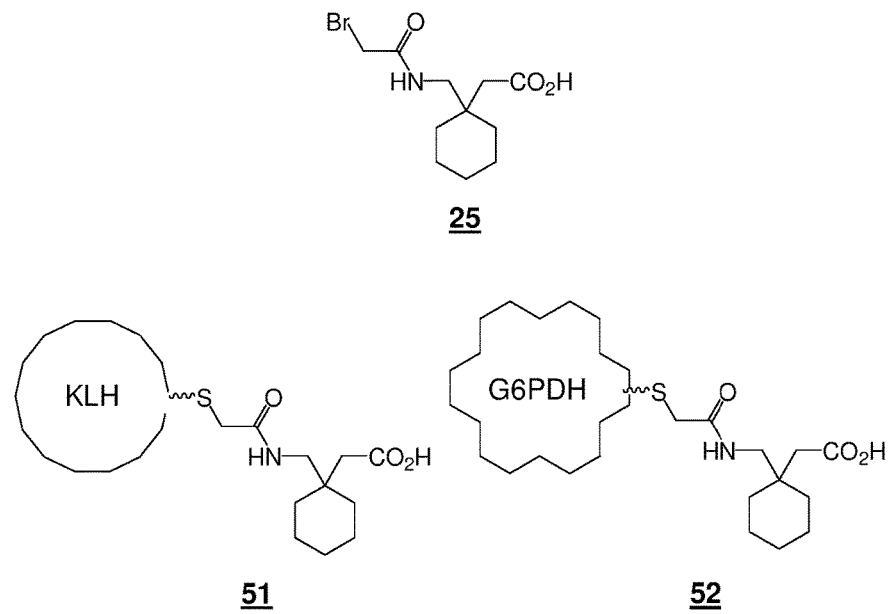
Figure 8I:
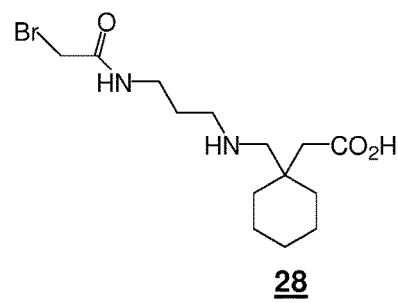
Figure 8I:
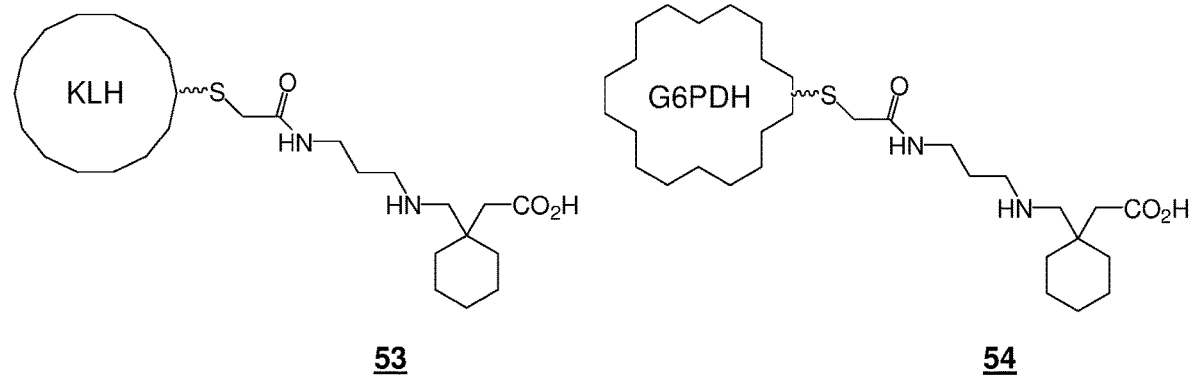
Figure 8J:
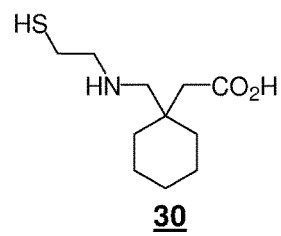
Figure 8J:
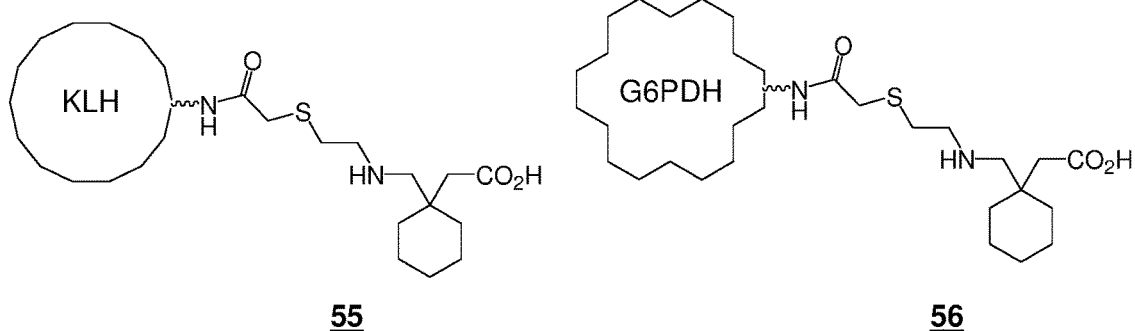
Figure 8K:
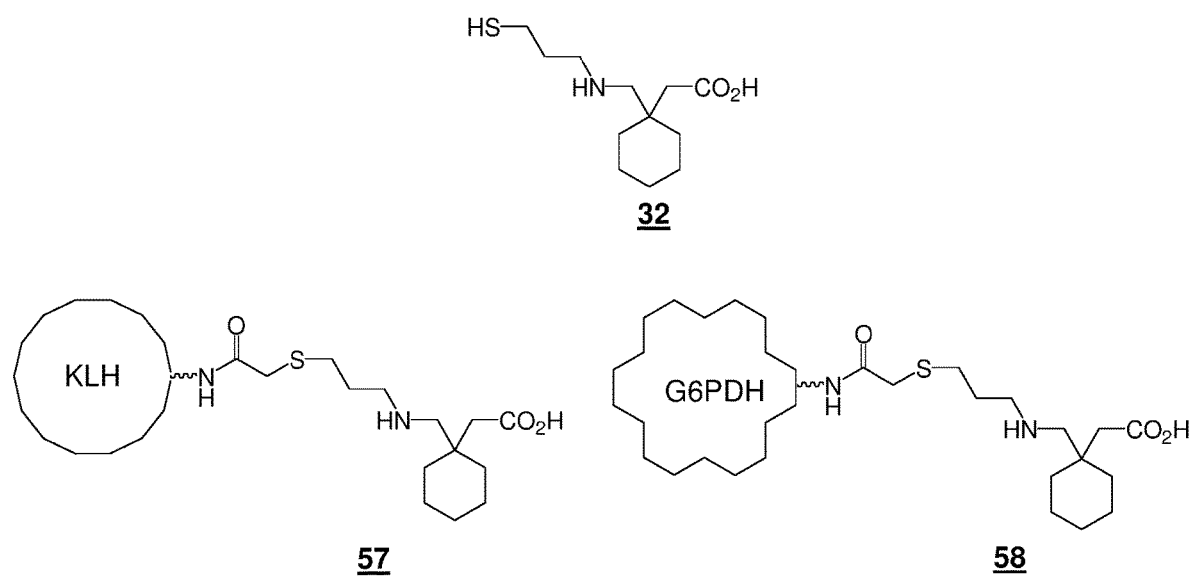

FIGS. 7A and 7B are schematic representation of preparation of reactive forms of KLH and an enzyme according to an embodiment. FIG. 7A represents an exemplary bromoacetylation of KLH and an enzyme. FIG. 8A represents an exemplary thiolation of KLH and G6PDH. FIGS. 8A-K are schematic representations of synthetic schemes of exemplary gabapentin conjugates—enzyme (e.g., G6PDH) conjugates and KLH conjugates using KLH or enzyme (e.g., G6PDH) prepared in FIGS. 7A and 7B.

Anti-Gabapentin Antibodies

As noted above, the term "antibody" as used in the context of the present disclosure, refers to a specific binding partner of an analyte (e.g., gabapentin), and is meant to encompass whole antibodies as well as antigen-binding fragments thereof (such as, for example, F(ab')2, Fab', Fab and Fv), naturally occurring antibodies, hybrid antibodies, chimeric antibodies, single-chain antibodies, and antibody fragments that retain antigen binding specificity, and the like. Antibodies can be of any class (e.g., IgM, IgG, IgA, IgE; frequently IgG) and generated from any source (although usually non-human, usually a non-human mammal such as a rabbit, mouse, rat, goat, etc.). Thus, "antibody" is meant to encompass not only intact immunoglobulin molecules, but also such fragments and derivatives of immunoglobulin molecules as may be prepared by techniques known in the art, and retaining the antibody activity of an intact immunoglobulin.

Antibodies may be derived from polyclonal compositions monoclonal compositions. As noted above, "antibodies" is also meant to encompass single chain antibodies or scFvs, where such recombinantly produced antibody fragments retain the binding characteristics of the above antibodies. Recombinantly produced antibody fragments within the meaning of "antibody" generally include at least the VH and VL domains of the subject antibodies, so as to retain the binding characteristics of the subject antibodies. These recombinantly produced antibody fragments may be readily prepared using any convenient methodology, such as the methodology disclosed in U.S. Pat. Nos. 5,851,829 and 5,965,371; the disclosures of which are herein incorporated by reference.

Anti-gabapentin antibodies include those that bind one or more gabapentin epitopes. Anti-gabapentin antibodies thus include antibodies that bind, particularly that specifically bind, one or more of an amine epitope of a gabapentin moiety, a carboxylic acid epitope of a gabapentin moiety, a cyclohexane epitope of a gabapentin moiety, or any combination thereof (e.g., both an amine epitope and a carboxylic acid epitope, both an amine epitope and a cyclohexane epitope, both a carboxylic acid epitope and a cyclohexane epitope, or all three epitopes). Anti-gabapentin antibodies may bind one or more of unconjugated gabapentin, a gabapentin derivative, a gabapentin conjugate, or any combination thereof.

Producing Anti-Gabapentin Antibodies

Anti-gabapentin antibodies can be prepared by using an immunogenic gabapentin conjugate described herein and applying methods for antibody production that are well known in the art. For examples of general techniques used in raising, purifying and modifying antibodies, and the design and execution of immunoassays, the reader is referred to Handbook of Experimental Immunology (D. M. Weir & C. C. Blackwell, eds.); Current Protocols in Immunology (J. E. Coligan et al., eds., 1991); David Wild, ed., The Immunoassay Handbook (Stockton Press N.Y., 1994); and R. Masseyeff, W. H. Albert, and N. A. Staines, eds., Methods of Immunological Analysis (Weinheim: VCH Verlags gesellschaft mbH, 1993).

Antibodies obtained using any of the disclosed techniques are screened or purified not only for their ability to react with gabapentin, but for a low cross-reactivity with potential interfering substances. "Cross-reactivity" may be determined in a quantitative immunoassay by establishing a standard curve using known dilutions of the target analyte, gabapentin. The standard curve is then used to calculate the apparent concentration of the interfering substance present in various known amounts in samples assayed under similar condition. The cross-reactivity is the apparent concentration divided by the actual concentration multiplied by 100. An exemplary immunoassay for determining cross-reactivity is a homogeneous enzyme immunoassay using a wild type G6PDH as described in U.S. Pat. No. 3,817,837 or mutant G6PDH engineered to contain a cysteine per subunit as described in U.S. Pat. Nos. 6,033,890, 6,090,567 and 6,455,288. Furthermore, the cross-reactivity can be determined in the same type of immunoassay in which the antibody will ultimately be used.

Producing Polyclonal Antibodies

Polyclonal antibodies that bind gabapentin may be raised by administration of an immunogenic gabapentin conjugate to an animal host, usually mixed with an adjuvant. Any animal host which produces antibodies can be used. The immunogen is conveniently prepared for injection by rehydrating lyophilized immunogen to form a solution or suspension. Exemplary adjuvants are water-in-oil immersions, particularly Freund's complete adjuvant for the first administration, and Freund's incomplete adjuvant for booster doses. The preparation is typically administered in a variety of sites, and typically in two or more doses over a course of at least 4 weeks. Serum is harvested and tested for the presence of anti-gabapentin antibody using a gabapentin-protein conjugate or other gabapentin conjugates in a standard immunoassay or precipitation reaction.

Polyclonal antisera typically contain antibodies not reactive with gabapentin and cross-reactive with other substances. Methods for purifying specific antibodies from a polyclonal antiserum are known in the art. A particularly effective method is affinity purification using a column of gabapentin conjugated to a solid phase. One manner of preparing a gabapentin column is to conjugate gabapentin or a gabapentin derivative to a protein other than the protein used in the immunogen, and then attach the conjugate to a commercially available activated resin, such as CNBr-activated SEPHAROSE™. The anti-gabapentin antibody is passed over the column, the column is washed, and the antibody is eluted with a mild denaturing buffer such as 0.1 M glycine, 0.2 M NaCl, pH 2.5.

Producing Monoclonal Antibodies

Anti-gabapentin monoclonal antibodies are prepared by a number of different techniques known in the art. For example, for hybridoma technology, the reader is referred generally to Harrow & Lane (1988), U.S. Pat. Nos. 4,491,632, 4,472,500, and 4,444,887, and Methods in Enzymology, 73B:3 (1981). One common way to produce monoclonal antibodies is to immortalize and clone a splenocyte or other antibody-producing cell recovered from an animal that has been immunized against gabapentin as described earlier. The clone is immortalized by a procedure such as fusion with a non-producing myeloma, by transfecting with Epstein Barr Virus, or transforming with oncogenic DNA. The treated cells are cloned and cultured, and clones are selected that produce antibody of the desired specificity. Specificity testing may be performed on culture supernatants by a number of techniques, such as using the immunizing antigen as the detecting reagent in an immunoassay. A supply of monoclonal antibody from the selected clone can then be purified from a large volume of culture supernatant, or from the ascites fluid of suitably prepared host animals injected with the clone. The antibody may be tested for activity as raw supernatant or ascites, and is optionally purified using standard biochemical preparation techniques such as ammonium sulfate precipitation, ion exchange chromatography, and gel filtration chromatography.

Producing Fragments and Other Derivatives of Immunoglobulins

Fragments and other derivatives of immunoglobulins can be prepared by methods of standard protein chemistry, for example, subjecting the antibody to cleavage with a proteolytic enzyme such as pepsin, papain, or trypsin; and reducing disulfide bonds with such reagents as dithiothreitol. Genetically, engineered variants of intact immunoglobulin can be produced by obtaining a polynucleotide encoding the antibody, and applying the general methods of molecular biology to splice encoding sequences or introduce mutations and translate the variant. Antibodies that are engineered variants of particular interest include chimeric and humanized antibodies, Fab-like fragments, single-chain variable region fragments (scFv), and diabodies.

Detectably Labeled Anti-Gabapentin Antibodies

The anti-gabapentin antibodies may also be labeled in order to facilitate detection. A variety of protein labeling schemes are known in the art and may be employed, the particular scheme and label chosen being the one most convenient for the intended use of the antibody, e.g. immunoassay.

Examples of labels include labels that permit both the direct and indirect measurement of the presence of the antibody. Examples of labels that permit direct measurement of the antibody include radiolabels, such as $^3$H or $^{125}$I, fluorescers, dyes, beads, chemiluminescers, colloidal particles, and the like. Examples of labels which permit indirect measurement of the presence of the antibody include enzymes where a substrate may provide for a colored or fluorescent product. For example, the antibodies may be labeled with a covalently bound enzyme capable of providing a detectable product signal after addition of suitable substrate. Instead of covalently binding the enzyme to the antibody, the antibody may be modified to comprise a first member of specific binding pair which specifically binds with a second member of the specific binding pair that is conjugated to the enzyme, e.g. the antibody may be covalently bound to biotin and the enzyme conjugate to streptavidin. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

Immunoassays

The present disclosure provides immunoassay methods for assessing the presence or absence of gabapentin in a sample of interest. Due to various factors, including the pronounced inter-individual variability in gabapentin pharmacokinetics, immunoassays to assess gabapentin status are of interest. Since gabapentin is excreted renally unchanged and is not metabolized or at least does not produce detectable metabolites. Therefore, there are no pharmacogenomic issues that affect gabapentin concentration and it is not subject to significant pharmacokinetic drug interactions with other drugs Immunoassays of the present disclosure can be of a variety of formats. The immunoassays may be separation immunoassays (also known as heterogeneous immunoassays) or homogeneous immunoassays. Furthermore, the immunoassays may be qualitative or quantitative. Assays of this disclosure include both sandwich and competition assays. The immunoassays may embody assays that are neither sandwich nor competition assays, as in certain assays involving immunoprecipitation.

In general, the immunoassays of the present disclosure for detecting the presence of absence of gabapentin in a sample can be conducted by adding, to a reaction mixture, (i) a sample suspected of containing gabapentin and (ii) an anti-gabapentin antibody capable of forming of a complex of gabapentin that may be present in the sample and the antibody; and detecting the presence or absence of the complex. The presence or absence of said complex is indicative of the presence or absence of gabapentin in said sample. Moreover, the amount of complex formed can be assessed to determine the concentration of gabapentin present in the sample (e.g., to provide an assessment of serum or tissue concentration of gabapentin in a subject from whom the sample was obtained). The presence and/or amount of complex can be assessed directly (e.g., by detecting bound antibody in the complex) or indirectly (e.g., by assessing activity of an enzyme in a gabapentin enzyme conjugate, where when the gabapentin enzyme conjugate is not bound to antibody, a detectable signal is generated, indicating that the anti-gabapentin antibody in the reaction mixture has been bound by gabapentin from the sample).

In general, the immunoassays of the disclosure entail combining the sample with an anti-gabapentin antibody under conditions that permit the formation of a stable complex between the analyte to be tested and the antibody.

Assays may be performed in solution or may use a solid (insoluble) support (e.g. polystyrene, nitrocellulose, or beads), using any standard methods (e.g., as described in Current Protocols in Immunology, Coligan et al., ed.; John Wiley & Sons, New York, 1992). Typical methods include ELISAs (enzyme-linked immunosorbent assays), IRMAs (immunoradiometric assays), and RIAs (radioimmunoassays).

Where the assay is performed in solution, the test samples (and, optionally a control sample) is incubated with an anti-gabapentin antibody for a time period sufficient to allow formation of analyte and affinity reagent complexes, for example, between about 0.1 hrs up to 24 hrs, or more. As previously noted, the anti-gabapentin antibody may include a detectable label (e.g. radionuclide, fluorescer, or enzyme). The sample is then treated to separate the gabapentin-antigabapentin antibody complexes from excess, unreacted anti-gabapentin antibody (e.g. by addition of an anti-anti-gabapentin antibody (e.g., anti-immunoglobulin antiserum) followed by centrifugation to precipitate the complexes, or by binding to an affinity surface such as a second, unlabelled anti-gabapentin antibody fixed to a solid substrate such as Sepharose® or a plastic well). Detection of anti-gabapentin antibody bound to a gabapentin may be achieved in a variety of ways well known in the art. If necessary, a substrate for the detectable label may be added to the sample.

Where the assay uses a solid support, the support can have an anti-gabapentin antibody (or gabapentin conjugate) bound to a support surface. Binding of the assay reagent facilitates the stable, wash-resistant binding of gabapentin which may be present in the sample (or anti-gabapentin antibody that is not bound to gabapentin from the sample, and is present in the reaction mixture, as in a competitive binding assay) to the solid support via specific binding to the anti-gabapentin antibody. The insoluble supports may be any compositions to which antibodies or suitable gabapentin conjugates can be bound, which is readily separated from soluble material, and which is otherwise compatible with the overall method of detection of anti-gabapentin antibody a sample.

The surface of such supports may be solid or porous and of any convenient shape. Examples of suitable insoluble supports to which the anti-gabapentin antibody is bound include beads, e.g. magnetic beads, membranes and microtiter plates. These can be composed of glass, plastic (e.g. polystyrene), polysaccharides, nylon or nitrocellulose.

Assay reagents can include the anti-gabapentin antibodies as disclosed herein, as well as anti-anti-gabapentin antibodies, which may be optionally detectably labeled. Methods for binding antibodies or other proteins to solid supports are well known in the art. After binding of an assay reagent to the support, the support may be treated with a blocking agent, which binds to the support in areas not occupied by the assay reagent Suitable blocking agents include non-interfering proteins such as bovine serum albumin, casein, gelatin, and the like. Alternatively, several detergents at non-interfering concentrations, such as Tween, NP40, TX100, and the like may be used. Such blocking treatment reduces nonspecific binding.

Qualitative and Quantitative Methods

Assays of this disclosure include both qualitative and quantitative assays. Typical quantitative methods involve mixing an analyte with a pre-determined amount of the reagent antibody, and correlating the amount of complex formed with the amount of analyte in the original sample using a relationship determined using standard samples containing known amounts of analyte in the range expected for the sample to be tested. In a qualitative assay, sufficient complex above or below a threshold level established by samples known to contain or be free of analyte establish the assay result. Unless otherwise stated, the act of "measuring" or "determining" in this disclosure refers alternately to qualitative and quantitative determination.

Samples

Samples may be biological samples taken from subjects suspected of being administered gabapentin.

As used herein, a "biological sample" refers to a sample of tissue or fluid isolated from a subject, which in the context of the invention generally refers to samples suspected of containing gabapentin, which samples, after optional processing, can be analyzed in an in vitro assay.

Exemplary samples of interest include, but are not necessarily limited to, a "blood sample" (which as used herein is meant to include whole blood, plasma, serum, and the like), fecal matter, urine, tears, sweat saliva, milk, organs, biopsies, secretions of the intestinal and respiratory tracts, vitreous humor, and fluids obtainable during autopsy (such as cerebrospinal fluid). It should be noted that a "blood-derived sample" refers to a sample that is prepared from blood or a fraction thereof, e.g., plasma or serum. Respiratory secretions (e.g., samples obtained from fluids or tissue of nasal passages, lung, and the like), "Human serum", as used herein, refers to the aqueous portion of human blood remaining after the fibrin and suspended material (such as cells) have been depleted.

Blood samples, such as serum samples, can be obtained by any suitable method. In one embodiment, a trough serum/plasma is used and the concentration range is 12-20 mg. Sweat samples can be obtained using, for example, a PharmChek® sweat patch from Sudormed. The PharmChek® sweat patch includes a semi-occlusive dressing containing a medical grade cellulose blotter paper collection pad, covered by a thin layer of polyurethane and acrylate adhesives. At the end of the wear period, the pad is eluted with a suitable buffer, such as 2.5 mL of 0.2 M acetate buffer with methanol at pH 5.0 (25:75) or with acetonitrile. Furthermore, the biological samples may also be tissue samples, which are extracted into liquid medium for immunoassay. For example, hair samples can be tested by extracting into a liquid medium. The samples may be diluted or modified to facilitate the assay.

The samples may be experimental samples generated by any chemical or biological method. For example, the samples may be standards containing known concentrations of gabapentin or other substances used for assay calibration.

In some embodiments, the biological sample will be diluted in a suitable solution prior to assaying. In general, a solution suitable for diluting a biological sample will include a buffer, such as phosphate buffered saline (PBS), and may include additional items, such as for example, a non-specific blocking agent, such as bovine serum albumin (BSA), a detergent, such as Triton-X-100, and the like.

Where desired, appropriate control samples for the assay include blood, serum, or urine collected from human subjects who have not received gabapentin (i.e., a negative control), or samples which contain a known, predetermined amount of a gabapentin analyte (i.e., a positive control). Alternatively, test results can be compared to detectable signal levels known to be associated with the presence or absence of gabapentin and/or correlated with an amount of gabapentin, e.g., a serum level of gabapentin.

The assays may optionally include use of a calibration standard. "Calibration standard", as used herein, refers to an aqueous medium containing gabapentin at a predetermined concentration. In an exemplary embodiment, a series of these calibration standards are available at a series of predetermined concentrations. In another exemplary embodiment, the calibration standard is stable at ambient temperature. In yet another exemplary embodiment, the calibration standards are in a synthetic matrix. In yet another exemplary embodiment, the calibration standards are in a non-synthetic matrix such as human serum.

In many embodiments, a suitable initial source for the human sample is a blood sample. As such, the sample employed in the subject assays is generally a blood-derived sample. The blood derived sample may be derived form whole blood or a fraction thereof, e.g., serum, plasma, etc., where in some embodiments the sample is derived from blood allowed to clot and the serum separated and collected to be used to assay.

In embodiments in which the sample is a serum or serum derived sample, the sample is generally a fluid sample. Any convenient methodology for producing a fluid serum sample may be employed. In many embodiments, the method employs drawing venous blood by skin puncture (e.g., finger stick, venipuncture) into a clotting or serum separator tube, allowing the blood to clot, and centrifuging the serum away from the clotted blood. The serum is then collected and stored until assayed. Once the patient derived sample is obtained, the sample is assayed to determine the level of gabapentin analyte.

Immunoassay Reagents

Immunoassay reagents that find use alone or in combination in the assays described herein include anti-gabapentin antibodies, gabapentin conjugates, and gabapentin (e.g., as a control or in competitive binding assays). Immunoassay reagents can be provided in a buffered aqueous solution. Such solutions may include additional components such as surface active additives, organic solvents, defoamers, buffers, surfactants, and anti-microbial agents. Surface active additives are introduced to maintain hydrophobic or low-solubility compounds in solution, and stabilize components in the solution. Examples include bulking agents such as betalactoglobulin (BLG) or polyethyleneglycol (PEG); defoamers and surfactants such as Tween-20, Plurafac A38, Triton X-100, Pluronic 25R2, rabbit serum albumin (RSA), bovine serum albumin (BSA), and carbohydrates. Examples of organic solvents can include methanol and other alcohols. Various buffers may be used to maintain the pH of the solution during storage. Illustrative buffers include HEPES, borate, phosphate, carbonate, tris, barbital and the like. Anti-microbial agents also extend the storage life of the immunoassay reagent.

Anti-Gabapentin Antibodies

Immunoassays generally involve at least one anti-gabapentin antibody, which may be produced by the methods disclosed herein. In an embodiment, the assays involve using an antibody raised against a gabapentin derivative-protein conjugate, particularly a low cross-reactivity with non-gabapentin molecules that may be present in a reaction mixture. Anti-gabapentin antibodies can be polyclonal or monoclonal, more commonly monoclonal, antibodies, capable of specifically binding gabapentin.

Depending upon the assay format, the anti-gabapentin antibody can be optionally detectably labeled, may be used in conjunction with a secondary antibody (i.e., an antibody that specifically binds an anti-gabapentin antibody) that may be detectably labeled. Exemplary detectable labels for antibodies are described infra.

Gabapentin Conjugates

Gabapentin conjugates variously find use as immunoassay reagents depending on the assay format. For example, gabapentin conjugate can act as based on competitive binding reagent in competitive binding assays, or can provide for a detectable signal when not bound by an anti-gabapentin antibody (e.g., where the gabapentin conjugate is a gabapentin G6PDH conjugate). Exemplary gabapentin conjugates useful as immunoassay reagents are described below.

Detectable Labels

A variety of detectably labels can be used in connection with the gabapentin conjugate assay reagents for use in the methods disclosed herein. Such detectable labels can be isotopic labels. In other embodiments, the detectable labels are non-isotopic signal-generating moieties, such as fluorophores and enzymes. Exemplary detectable labels are described below. It will be apparent that while the detectable labels are described below in the context of their use in gabapentin conjugates, many can also be adapted for use with anti-gabapentin antibodies.

Fluorophores

"Fluorophore" as used herein refers to moiety that itself fluoresces, can be made to fluoresce, or can provide for quenching of fluorescence of a flurophor of a FRET pair (e.g., as in a FRET pair). In principle, any fluorophore can be used in the assays of this invention. In general, the fluorophore is selected so as to be compatible for use in the assay format desired, and selected so as to be relatively insensitive to the assay conditions, e.g., pH, polarity, temperature and ionic strength.

Exemplary fluorophores can be characterized as having the following characteristics: a. A fluorescence lifetime of greater than about 15 nsec; b. An excitation wavelength of greater than about 350 nm; c. A Stokes shift (a shift to lower wave-length of the emission relative to absorption) of greater than about 20 nm; d. For homogeneous assays described below, fluorescence lifetime should vary with binding status; and e. The absorptivity and quantum yield of the fluorophore should be high. The longer lifetime is advantageous because it is easier to measure and more easily distinguishable from the Raleigh scattering (background). Excitation wavelengths greater than 350 nm reduce background interference because most fluorescent substances responsible for background fluorescence in biological samples are excited below 350 nm. A greater Stokes shift also allows for less background interference.

The fluorophores generally have a functional group available for conjugation either directly or indirectly to a gabapentin intermediate to generate a gabapentin conjugate having the attached fluorophore.

Fluorophores for use in heterogeneous assays can be relatively insensitive to binding status. In contrast, fluorophores for use in homogeneous assay can be sensitive to binding status, i.e., the fluorescence lifetime must be alterable by binding so that bound and free forms can be distinguished.

Examples of fluorophores useful in the invention are naphthalene derivatives (e.g. dansyl chloride), anthracene derivatives (e.g. N-hydroxysuccinimide ester of anthracene propionate), pyrene derivatives (e.g. N-hydroxysuccinimide ester of pyrene butyrate), fluorescein derivatives (e.g. fluorescein isothiocyanate), rhodamine derivatives (e.g. rhodamine isothiocyanate), phycoerythin, and Texas Red.

Enzymes

In an exemplary embodiment, the signal-generating moiety is an enzyme. From the standpoint of operability, a very wide variety of enzymes can be used. But, as a practical matter, some enzymes have characteristics which make them more readily adaptable to the methods disclosed herein.

The enzyme can be selected so as to be stable to provide for desirable shelf-life, e.g., stable when stored for a period of at least three months or at least six months at temperatures which are convenient to store in the laboratory, normally −20° C. or above. The enzyme can be selected so as to have a satisfactory turnover rate at or near the pH optimum for binding to the antibody, this is normally at about pH 6-10, usually 6.0 to 8.0. A product of the enzymatic reaction facilitated by the enzyme can be either formed or destroyed as a result of the enzyme reaction, and can provide a enzyme reaction product which absorbs light in the ultraviolet region or the visible region, that is the range of about 250-750 nm., usually 300-600 nm. The enzyme may also have a substrate (including cofactors) which has a molecular weight in excess of 300, or in excess of 500. The enzyme which is employed or other enzymes, with like activity, will not be present in the sample to be measured, or can be easily removed or deactivated prior to the addition of the assay reagents. Also, the enzyme can be selected so as to avoid the impact of any naturally occurring inhibitors for the enzyme that may be present in samples to be assayed or as some other component of the reaction mixture.

Although enzymes of up to 600,000 molecular weight can be employed, usually relatively low molecular weight enzymes will be employed of from 10,000 to 300,000 molecular weight, more usually from about 10,000 to 150,000 molecular weight, and frequently from 10,000 to 100,000 molecular weight. Where an enzyme has a plurality of subunits the molecular weight limitations refer to the enzyme and not to the subunits.

It may be desirable to select an enzyme that is susceptible to detectable labeling. In this instance, the enzyme can be detectable labeled using appropriate detectable labels exemplified herein.

Exemplary enzymes include, but are not limited to: alkaline phosphatase, horseradish peroxidase, lysozyme, glucose-6-phosphate dehydrogenase, lactate dehydrogenase, β-galactosidase, and urease. Also, a genetically engineered fragment of an enzyme may be used, such as the donor and acceptor fragment of β-galactosidase utilized in CEDIA immunoassays (see, e.g., Henderson D R et al. Clin Chem. 32(9):1637-1641 (1986)); U.S. Pat. No. 4,708,929. These and other enzymes which can be used have been discussed in detail by Eva Engvall in Enzyme Immunoassay ELISA and EMIT in Methods in Enzymology, 70:419-439 (1980) and in U.S. Pat. No. 4,857,453.

In an exemplary embodiment, the enzyme is glucose-6-phosphate dehydrogenase (G6PDH) and it is attached to a gabapentin derivative, thus forming a gabapentin-reactive partner conjugate. An anti-gabapentin antibody used in conjunction with such gabapentin conjugates can be selected so as to specifically bind the gabapentin epitope presented by the gabapentin enzyme conjugate, and thus affect activity of the gabapentin enzyme conjugate.

For assays employing gabapentin-enzyme conjugates, as an exemplary protein conjugate, in which a gabapentin derivative is labeled with an enzyme, the gabapentin derivative can be attached to the enzyme by any suitable method. In certain embodiments, the chemistry described herein for formation of immunogenic protein conjugates of gabapentin derivatives is also used to prepare the enzyme conjugate. In this way, the gabapentin moiety presented to the antibody can more mirror the gabapentin epitope to which the antibody specifically binds.

The selection procedure is exemplified using a gabapentin-reactive partner conjugate comprising G6PDH as the reactive partner and a gabapentin derivative as the hapten. The first step in selecting a antibody involves testing the magnitude of antibody inhibition of a gabapentin-reactive partner conjugate. In this step, the goal is to determine and select for those antibodies which significantly inhibit the enzyme activity of G6PDH. Antibodies which perform well in the first test are then subjected to a second test. Here, the antibody is first incubated with gabapentin. Next the gabapentin-reactive partner conjugate is added. An exemplary antibody preferentially binds to gabapentin instead of the gabapentin-reactive partner conjugate. The reduction in binding to the gabapentin-reactive partner conjugate would be visible as an increase G6PDH activity.

Detection
Via Fluorescence

When a fluorescently labeled analyte (i.e., gabapentin antigen or antibody) is employed, the fluorescence emitted is proportional (either directly or inversely) to the amount of analyte. The amount of fluorescence is determined by the amplitude of the fluorescence decay curve for the fluorescent species. This amplitude parameter is directly proportional to the amount of fluorescent species and accordingly to the analyte.

In general spectroscopic measurement of fluorescence is accomplished by: a. exciting the fluorophore with a pulse of light; b. detecting and storing an image of the excitation pulse and an image of all the fluorescence (the fluorescent transient) induced by the excitation pulse; c. digitizing the image; d. calculating the true fluorescent transient from the digitized data; e. determining the amplitude of the fluorescent transient as an indication of the amount of fluorescent species.

According to the method, substantially all of the fluorescence emitted by the fluorescent species reaching the detector as a function of time from the instant of excitation is measured. As a consequence, the signal being detected is a superimposition of several component signals (for example, background and one analyte specific signal). As mentioned, the individual contributions to the overall fluorescence reaching the detector are distinguished based on the different fluorescence decay rates (lifetimes) of signal components. In order to quantitate the magnitude of each contribution, the detected signal data is processed to obtain the amplitude of each component. The amplitude of each component signal is proportional to the concentration of the fluorescent species.

Via Enzyme

Detection of the amount of product produced by the gabapentin-reactive partner conjugate of the invention can be accomplished by several methods which are known to those of skill in the art. Among these methods are colorimetry, fluorescence, and spectrophotometry. These methods of detection are discussed in "Analytical Biochemistry" by David Holme, Addison-Wesley, 1998, which is incorporated herein by reference.

Solid Supports

The gabapentin conjugates and/or the anti-gabapentin antibodies to be used as reagents in an assay can be insolubilized by attachment to a solid phase. This can be, for example, a wall of a vessel containing the reagent, to a particulate, or to a large molecular weight carrier that can be kept in suspension but is removable by physicochemical means, such as centrifugation or microfiltration. The attachment need not be covalent, but is at least of sufficient permanence to withstand any separation techniques (including washes) that are part of the assay procedure. Exemplary particulate materials include agarose, polystyrene, cellulose, polyacrylamide, latex particles, magnetic particles, and fixed red cells. Examples of commercially available matrices include Sepharose® (Pharmacia), Poros® resins (Roche Molecular Biochemicals), Actigel Superflow™ resins (Sterogene Bioseparations Inc.), and Dynabeads™ (Dynal Inc.). The choice is not critical, and will generally depend on such features as stability, capacity, accessibility of the coupled antibody, flow rate (or the ability to disperse the resin in the reaction mixture), and ease of separation.

Assay Formats

As noted above, immunoassays for detection of gabapentin can be of a variety of formats, In general, the immunoassays involve combining one or more immunoassay reagents (e.g., at least a anti-gabapentin antibody) with a test sample (i.e., a sample suspected of containing gabapentin) in a reaction mixture. "Reaction mixture" generally refers to the combination of a sample suspected of containing gabapentin and one or more immunoassay reagents as exemplified in the present disclosure to facilitate detection of the presence or absence of gabapentin in the sample, where the detection may be qualitative or quantitative. The reaction mixture is usually an aqueous solution, although the immunoassay reagent(s) may be in solution or immobilized on a support (e.g., a substrate such as a bead). The reaction mixture can include other components compatible with the immunoassay, e.g., buffers, and the like.

Immunoassays usually are classified in one of several ways. For example, immunoassays can be classified according to the mode of detection used, i.e., enzyme immunoassays, radio immunoassays, fluorescence polarization immunoassays, chemiluminescence immunoassays, turbidimetric assays, etc. Another grouping method is according to the assay procedure used, i.e., competitive assay formats, sandwich-type assay formats as well as assays based on precipitation or agglutination principles. In the instant application, a further distinction is made depending on whether washing steps are included in the procedure (so-called heterogeneous assays) or whether reaction and detection are performed without a washing step (so-called homogeneous assays). Exemplary assays are described in more detail below.

Homogeneous and Heterogeneous Immunoassays

Immunoassays may be described as heterogeneous or homogeneous. "Homogeneous immunoassay", as used herein, refers to an assay method where the complex is typically not separated from unreacted reaction components, but instead the presence of the complex is detected by a property which at least one of the reactants acquires or loses as a result of being incorporated into the complex. Homogeneous assays known in the art include systems involving fluorochrome and fluorochrome quenching pairs on different reagents; enzyme and enzyme inhibitor pairs on different reagents; chromophore and chromophore modifier pairs on different reagents; and latex agglutination assays.

An exemplary homogeneous assay is the quantitative homogeneous enzyme immunoassay in which a gabapentin moiety is conjugated to an active enzyme. The conjugation is arranged so that the binding of an anti-gabapentin antibody to the derivative affects enzymatic activity in a qualitative or quantitative fashion. If a sample containing gabapentin is premixed with the antibody, the antibody will complex with the gabapentin and be prevented from binding to the enzyme conjugate. In this way, the activity of the enzyme can be correlated with the amount of gabapentin present in the sample.

G6PDH is an exemplary enzyme useful in such assays. In one embodiment, the G6PDH is a variant of a naturally-occurring G6PDH in which one or more lysine residues are deleted or substituted, or one or more cysteine residues are introduced. For example, *Leuconostoc mesenteroides* G6PDH are dimeric enzymes that have the ability to catalyze the oxidation of D-glucose-6-phosphate to D-glucono-delta-lactone-6-phosphate by utilizing either $NAD^+$ or $NADP^+$. This property of using NAD differentiates these enzymes from human G6PDH, which utilizes only NADP effectively, and allows *L. mesenteroides*-specific G6PDH activity to be measured in the presence of human G6PDH, as for example in human samples. G6PDHs from *L. mesenteroides* are used in current EMIT™ homogeneous immunoassays (Syva Company, Palo Alto, Calif., U.S.A.). Two exemplary genera of bacteria from which to select G6PDH are *Leuconostoc* and *Zymomonas*. Within these genera *L. mesenteroides, L. citreum, L. lactis, L. dextranicum*, and *Z. mobilis* are of most interest, *L. mesenteroides, L. citreum, L. lactis* are specific examples.

Figure 5:
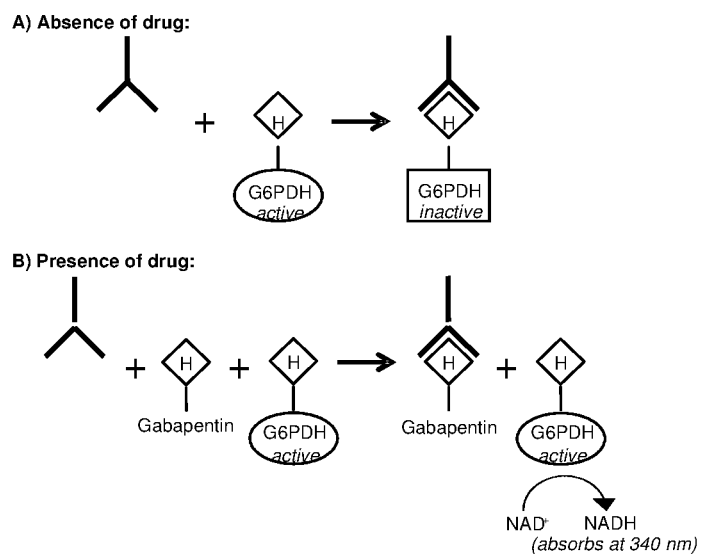
FIG. 5 is a schematic representation of a homogeneous, competitive immunoassay for gabapentin using an anti-gabapentin antibody and a gabapentin-G6PDH enzyme conjugate.

FIG. 5 shows an exemplary scheme of a homogeneous, competitive immunoassay for gabapentin using an anti-gabapentin antibody and a gabapentin-G6PDH enzyme conjugate in a plasma sample. In the absence of plasma drug (A), an anti-gabapentin antibody binds to the gabapentin (H)-enzyme(G6PDH) conjugate and inactivates the enzyme. In the presence of plasma drug (B), gabapentin from plasma, if present, competes with the gabapentin-G6PDH conjugate for binding to the antibody, thus allowing some fraction of the gabapentin-G6PDH conjugate to become active and convert $NAD^+$ to NADH. The active G6PDH produces an absorbance signal change over time at 340 nm. It is critical for the drug of interest to be exposed to the antibody before the gabapentin-G6PDH conjugate; otherwise the antibody would become saturated with gabapentin-G6PDH conjugate and would be unable to detect the drug. Therefore, the assay involves incubation of the sample and antibody before addition of the gabapentin-G6PDH conjugate.

Another example of a homogeneous assay system is the cloned enzyme donor immunoassay, described in more detail below.

In a separation-based or "heterogeneous" assay, the detecting of a complex of an anti-gabapentin antibody and an analyte involves a process wherein the complex formed is physically separated from either unreacted analyte, unreacted antibody, or both.

In a heterogeneous immunoassay, a complex of an anti-gabapentin antibody and an analyte may be first formed in the fluid phase, and then subsequently captured by a solid phase reagent or separated on the basis of an altered physical or chemical property, such as by gel filtration or precipitation. Alternatively, one of the reagents may be attached to a solid phase before contacting with other reagents, and then the complex may be recovered by washing the solid phase free of unreacted reagents. Separation-based assays typically involve use of a labeled derivative or antibody to facilitate detection or quantitation of the complex. Suitable labels include radioisotopes such as $^{125}I$, enzymes such as peroxidase and β-galactosidase, and fluorescent labels such as fluorescein isothiocyanate. The separation step involves removing labeled reagent present in complex form from unreacted labeled reagent. The amount of label in the complex can be measured directly or inferred from the amount left unreacted.

Sandwich and Competition Assays

Assays of this disclosure include both sandwich and competition assays. Sandwich assays typically involve forming a complex in which the analyte to be measured is sandwiched between one reagent, such as a first antibody used ultimately for separation of the complex, and another reagent, such as a second antibody used as a marker for the separated complex. Competition assays involve a system in which the analyte to be measured competes with a derivative of the analyte for binding to another reagent, such as an antibody. An example of a competition assay using EMIT® is described in U.S. Pat. No. 3,817,837.

In one embodiment, the immunoassay further comprises adding a gabapentin conjugate comprising a gabapentin moiety and a detectable label to the sample. The presence or absence of gabapentin in the sample can be detected by detecting the datable label. The detectable label may comprise an enzyme and the detecting is by assaying activity of the enzyme. In an embodiment, the enzyme is a dehydrogenase, more particularly, G6PDH.

Lateral Flow Chromatography

The compounds and methods of the invention also encompass the use of these materials in lateral flow chromatography technologies. The essence of lateral flow chromatography involves a membrane strip which comprises a detection device, such as a non-isotopic signal generating moiety, for gabapentin. A sample from a patient is then applied to the membrane strip. The sample interacts with the detection device, producing a result. The results can signify several things, including the absence of the gabapentin in the sample, the presence of the gabapentin in the sample, and even the concentration of the gabapentin in the sample.

In one embodiment, the invention provides a method of qualitatively determining the presence or absence of a gabapentin in a sample, through the use of lateral flow chromatography. The basic design of the qualitative lateral flow device is as follows: 1) The sample pad is where the sample is applied. The sample pad is treated with chemicals such as buffers or salts, which, when redissolved, optimize the chemistry of the sample for reaction with the conjugate, test, and control reagents. 2) Conjugate release pad is typically a polyester or glass fiber material that is treated with a conjugate reagent such as an antibody colloidal gold conjugate. A typical process for treating a conjugate pad is to use impregnation followed by drying. In use, the liquid sample added to the test will redissolve the conjugate so that it will flow into the membrane. 3) The membrane substrate is usually made of nitrocellulose or a similar material whereby antibody capture components are immobilized. 4) A wicking pad is used in tests where blood plasma must be separated from whole blood. An impregnation process is usually used to treat this pad with reagents intended to condition the sample and promote cell separation. 5) The absorbent pad acts as a reservoir for collecting fluids that have flowed through the device. 6) The above layers and membrane system are laminated onto a plastic backing with adhesive material which serves as a structural member.

In another embodiment, the invention provides a method of qualitatively determining the presence of a gabapentin in a sample, through the use of lateral flow chromatography. In this embodiment, the membrane strip comprises a sample pad, which is a conjugate release pad (CRP) which comprises a antibody that is specific for the gabapentin. This antibody is conjugated to a non-isotopic signal-generating moiety, such as a colloidal gold particle. Other detection moieties useful in a lateral flow chromatography environment include dyes, colored latex particles, fluorescently labeled latex particles, non-isotopic signal generating moieties, etc. The membrane strip further comprises a capture line, in which the gabapentin derivative antigen is immobilized on the strip. In some embodiments, this immobilization is through covalent attachment to the membrane strip, optionally through a linker. In other embodiments, the immobilization is through non-covalent attachment to the membrane strip. In still other embodiments, the immobile gabapentin derivative in the capture line is attached to a reactive partner, such as an immunogenic carrier like BSA.

Sample from a patient is applied to the sample pad, where it can combine with the antibody in the CRP, thus forming a solution. This solution is then allowed to migrate chromatographically by capillary action across the membrane. When the gabapentin is present in the sample, a gabapentin-antibody complex is formed, which migrates across the membrane by capillary action. When the solution reaches the capture line, the gabapentin-antibody complex will compete with the immobile gabapentin for the limited binding sites of the antibody. When a sufficient concentration of gabapentin is present in the sample, it will fill the limited antibody binding sites. This will prevent the formation of a colored antibody-immobile gabapentin complex in the capture line. Therefore, absence of color in the capture line indicates the presence of gabapentin in the sample.

In the absence of gabapentin in the sample, a colored antibody-immobile gabapentin complex will form once the solution reaches the capture line of the membrane strip. The formation of this complex in the capture line is evidence of the absence of gabapentin therapeutic in the sample.

In another embodiment, the invention provides a method of quantitatively determining the amount of a gabapentin in a sample, through the use of lateral flow chromatography. This technology is further described in U.S. Pat. Nos. 4,391,904; 4,435,504; 4,959,324; 5,264,180; 5,340,539; and 5,416,000, among others, which are herein incorporated by reference. In one embodiment, the antibody is immobilized along the entire length of the membrane strip. In general, if the membrane strip is made from paper, the antibody is covalently bound to the membrane strip. If the membrane strip is made from nitrocellulose, then the antibody can be non-covalently attached to the membrane strip through, for example, hydrophobic and electrostatic interactions.

The membrane strip comprises a CRP which comprises the gabapentin attached to a detector moiety. In an exemplary embodiment, the detector moiety is an enzyme, such as horseradish peroxidase (HRP).

Sample from a patient is applied to the membrane strip, where it can combine with the gabapentin/detector molecule in the CRP, thus forming a solution. This solution is then allowed to migrate chromatographically by capillary action across the membrane. When the gabapentin is present in the sample, both the sample gabapentin and the gabapentin/detector molecule compete for the limited binding sites of the antibody. When a sufficient concentration of gabapentin is present in the sample, it will fill the limited antibody binding sites. This will force the gabapentin/detector molecule to continue to migrate in the membrane strip. The shorter the distance of migration of the gabapentin/detector molecule in the membrane strip, the lower the concentration of gabapentin in the sample, and vice versa. When the gabapentin/detector molecule comprises an enzyme, the length of migration of the gabapentin/detector molecule can be detected by applying an enzyme substrate to the membrane strip. Detection of the product of the enzyme reaction is then utilized to determine the concentration of the gabapentin in the sample. In another exemplary embodiment, the enzyme's color producing substrate such as a modified N,N-dimethylaniline is immobilized to the membrane strip and 3-methyl-2-benzothiazolinone hydrazone is passively applied to the membrane, thus alleviating the need for a separate reagent to visualize the color producing reaction.

Fluorescence Polarization Immunoassay for Gabapentin

Fluorescence polarization immunoassay (FPIA) technology is based upon competitive binding between an antigen/drug in a sample and a known concentration of labeled antigen/drug. FPIA technology is described in, for example, U.S. Pat. Nos. 4,593,089, 4,492,762, 4,668,640, and 4,751,190, which are incorporated herein by reference. Accordingly, the FPIA reagents, systems, and equipment described in the incorporated references can be used with anti-gabapentin antibodies which are also anti-gabapentin analog antibodies.

The FPIA technology can be used to identify the presence of gabapentin and can be used in assays that quantify the amount of gabapentin in a sample. In part, the rotational properties of molecules in solution allow for the degree of polarization to be directly proportional to the size of the molecule. Accordingly, polarization increases as molecular size increases. That is, when linearly polarized light is used to excite a fluorescent-labeled or other luminescent-labeled gabapentin or derivative thereof, which is small and rotates rapidly in solution, the emitted light is significantly depolarized. When the fluorescent-labeled gabapentin or derivative interacts with or is bound to an antibody, the rotation is slowed and the emitted light is highly polarized. This is because the antibody significantly and measurably increases the size of the complex. Also, increasing the amount of unlabeled gabapentin in the sample can result in decreased binding of the fluorescent-labeled gabapentin or derivative by the anti-gabapentin antibody, and thereby decrease the polarization of light emitted from sample. The quantitative relationship between polarization and concentration of the unlabeled gabapentin in the sample can be established by measuring the polarization values of calibrations with known concentrations of gabapentin. Thus, FPIA can be used to identify the presence and concentration of gabapentin in a sample.

In one embodiment, the assay involves an FPIA assay system. An example of components of the FPIA system can include the following: i) monoclonal or polyclonal anti-gabapentin antibodies capable of specifically binding to gabapentin and a gabapentin derivative; ii) a sample suspected of containing the gabapentin; and iii) gabapentin derivative labeled with a fluorescent moiety, such as fluorescein. Alternatively, the system can be provided as a kit exclusive of the sample. Additionally, the system can include various buffer compositions, gabapentin concentration gradient compositions or a stock composition of gabapentin, and the like.

Homogeneous Microparticle Immunoassay for Gabapentin

Homogeneous microparticles immunoassay ("HMI") technology, which can be referred to as immunoturbidimetric assays, is based on the agglutination of particles and compounds in solution. When particles and/or chemical compounds agglutinate, particle sizes can increase and increase the turbidity of a solution. Accordingly, anti-gabapentin antibodies can be used with microparticles and gabapentin derivatives in order to assess the presence, and optionally the amount, of gabapentin in a sample. HMI technologies can be advantageous because the immunoassays can be performed on blood, blood hemolysate, serum, plasma, tissue, and/or other samples. HMI assays can be configured to be performed with gabapentin and/or a gabapentin derivative loaded onto a microparticle, or with an anti-gabapentin antibody loaded onto a microparticle. HMI or immunoturbidimetric assays are well known in the art for measuring agglutination of substances in a sample.

Immunoturbidimetric assay technologies are described in, e.g., U.S. Pat. Nos. 5,571,728, 4,847,209, 6,514,770, and 6,248,597, which are included herein by reference. Such assays involve light attenuation, nephelometric, or turbidimetric methods. The formation of an agglutinated compound AB from gabapentin (A) and anti-gabapentin antibody microparticle binding partner (B) can be measured by the change which occurs in the scattering or absorption of the incident light directed into the sample. Alternatively, the anti-gabapentin antibody (A) can bind with a gabapentin or derivative loaded microparticle. When suspendable particles having an immobilized binding partner are used, there is an enhancement of the effects, which makes it possible to determine considerably lower gabapentin concentrations. These homogeneous methods can be carried out quickly and simply, and permit, in particular, the automation of sample analyses as described in more detail below.

Cloned Enzyme Donor Immunoassays for Gabapentin

Cloned enzyme donor Immunoassays ("CEDIA®", Roche Diagnostics), as are based upon the competition of gabapentin in the biological sample with a gabapentin conjugate containing an inactive genetically engineered enzyme-donor ("ED") fragment such as from β-D-galactoside galactohydrolase or β-galactosidase ("β-gal") from $E.$ $coli$, for binding to an antibody capable of binding gabapentin. If gabapentin is present in the sample it binds to the antibody, leaving the ED portion of the ED-derivative conjugate free to restore enzyme activity of β-D-galactoside galactohydrolase or B gal in the reaction mixture so as to be capable of association with enzyme acceptor ("EA") fragments. The active enzyme comprised of the ED and EA is then capable of producing a quantifiable reaction product when exposed to an appropriate substrate. A preferred substrate is chlorophenol red-β-D-galactopyranoside ("CPRG"), which can be cleaved by the active enzyme into galactose and CPR, wherein CPR is measured by absorbency at about wavelength 570 nm. In the instance gabapentin is not present in the sample, the antibody binds to the ED-derivative conjugate, thereby inhibiting association of the ED fragments with the EA fragments and inhibiting restoration of enzyme activity. The amount of reaction product and resultant absorbance change are proportional to the amount of gabapentin in the sample.

Chemiluminescent Heterogeneous Immunoassays for Gabapentin

A competitive assay using chemiluminescent microparticle immunoassay ("CMIA") technology can also be used to assess whether or not gabapentin is present in a sample. Various types of CMIA technologies are well known in the art of heterogeneous immunoassays for determining the presence and/or amount of a chemical entity in a sample. CMIA assays can include the use of anti-gabapentin antibodies, which are capable of binding to gabapentin and its derivatives, which are coupled to particles, such as magnetic particles or particles suitable for separation by filtration, sedimentation, and/or other means. Additionally, a tracer, which can include a gabapentin derivative linked to a suitable chemiluminescent moiety, can be used to compete with free gabapentin in the patient's sample for the limited amount of anti-gabapentin antibody on the particle. After the sample, tracer, and antibody particles interact and a routine wash step has removed unbound tracer, the amount of tracer bound to antibody particles can be measured by chemiluminescence, wherein chemiluminescence is expressed in Relative Light Units (RULE). The amount of chemiluminescence is inversely related to the amount of free drug in the patient's sample and concentration is determined by constructing a standard curve using known values of the drug.

Other Immunoassays for Gabapentin

The gabapentin derivatives, conjugates, antibodies, immunogens, and/or other conjugates described herein are also suitable for any of a number of other heterogeneous immunoassays with a range of detection systems including but not limited to enzymatic or fluorescent, and/or homogeneous immunoassays including but not limited to rapid lateral flow assays, and antibody arrays, as well as formats yet to be developed.

While various immunodiagnostic assays have been described herein that utilize the gabapentin derivatives, conjugates, antibodies, immunogens and/or tracers, such assays can also be modified as is well known in the art. As such, various modifications of steps or acts for performing such immunoassays can be made within the scope of the present invention.

Kits

The present disclosure also provides kits that find use in practicing the subject methods, as described above. The kits of the present invention can comprise an anti-gabapentin antibody in a container, and may comprise a gabapentin conjugate (e.g., for use in a competitive binding assay, for use in an enzyme-based assay, and the like). The kits may also include a calibration standard and/or control standard useful in performing the assay; and, optionally, instructions on the use of the kit. Kit components can be in a liquid reagent form, a lyophilized form, or attached to a solid support. The reagents may each be in separate containers, or various reagents can be combined in one or more containers depending on cross-reactivity and stability of the reagents.

The sample, suspected of containing a gabapentin, and a calibration material, containing a known concentration of the gabapentin, are assayed under similar conditions. Gabapentin concentration is then calculated by comparing the results obtained for the unknown specimen with results obtained for the standard. This is commonly done by constructing a calibration or dose response curve.

Various ancillary materials may be employed in an assay in accordance with the present invention. In an exemplary embodiment, buffers and/or stabilizers are present in the kit components. In another exemplary embodiment, the kits comprise indicator solutions or indicator "dipsticks", blotters, culture media, cuvettes, and the like. In yet another exemplary embodiment, the kits comprise indicator cartridges (where a kit component is bound to a solid support) for use in an automated detector. In still another exemplary embodiment, additional proteins, such as albumin, or surfactants, particularly non-ionic surfactants, may be included. In another exemplary embodiment, the kits comprise an instruction manual that teaches a method of the invention and/or describes the use of the components of the kit.

Reagents and buffers used in the assays can be packaged separately or in combination into kit form to facilitate distribution. The reagents are provided in suitable containers, and typically provided in a package along with written instructions relating to assay procedures.

An embodiment of the present disclosure relates to a kit for conveniently determining the presence or the absence of gabapentin in a sample. The kit may comprise an anti-gabapentin antibody and a gabapentin calibration standard. The gabapentin calibration standard may comprise calibration and control standards useful in performing the assay. The kits can also optionally comprise a conjugate comprising a gabapentin moiety and a detectable signal. In an exemplary embodiment, a detectable signal of the conjugate is an enzyme. In yet another embodiment, the enzyme is glucose-6-phosphate dehydrogenase (G6PDH). In one embodiment, the G6PDH is a variant of a naturally-occurring G6PDH in which one or more lysine residues are deleted or substituted, or one or more cysteine residues are introduced.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Some of the examples have been performed via experiment and some are prophetic based on techniques, standards, and results well known in the art. Also, it should be apparent that the invention can include additional embodiments not illustrated by example. Additionally, many of the examples have been performed with experimental protocols well known in the art using the gabapentin derivatives, antigens, immunogens, and anti-gabapentin antibodies prepared in accordance with the present invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Preparation of 4-Amino Gabapentin Derivative (Formula III)

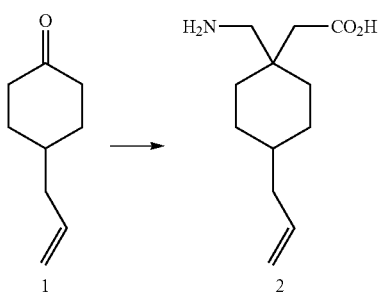

Compound 1 (13.8 gram, 0.1 mole) described in R. Funk, et al., JOC, (1983), 2632 and J. Stewart, et al., JACS, (1998), 354, which are incorporated herein by reference was converted to compound 2 as described in the literature U.S. Pat. Publication No. 2007/0123591 and Chinese Pat. CN1740161, which are incorporated herein by reference, in overall yield of 40% as a white powder.

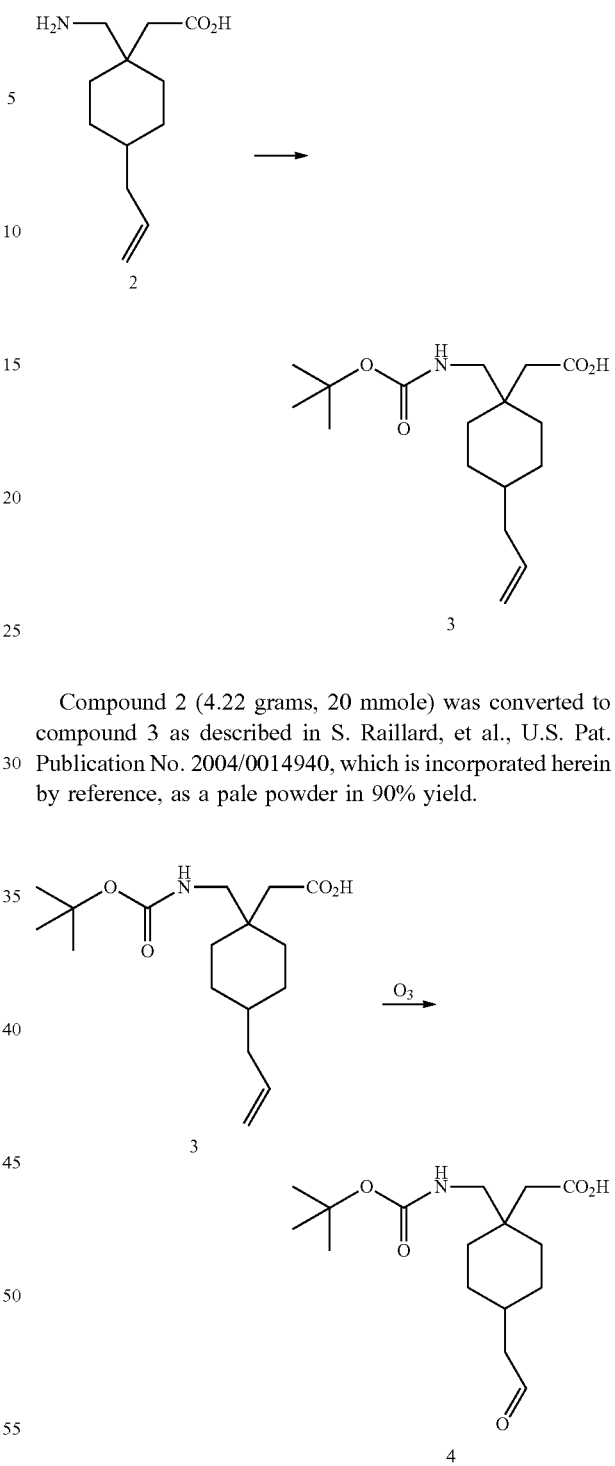

Compound 2 (4.22 grams, 20 mmole) was converted to compound 3 as described in S. Raillard, et al., U.S. Pat. Publication No. 2004/0014940, which is incorporated herein by reference, as a pale powder in 90% yield.

To a stirred solution of compound 3 (3.11 gram, 10 mmole) in methanol (100 ml) at −78° C. was bubbled ozone gas (1 ml/min) from an ozone generator for 1 hour. Nitrogen gas was then bubbled for 1 minute and mercaptomethanol (1 ml) was added to the reaction mixture and allowed to come to room temperature by removing the cooling bath. The solvent was than removed under reduced pressure to give aldehyde 4 (2.95 grams, 95%).

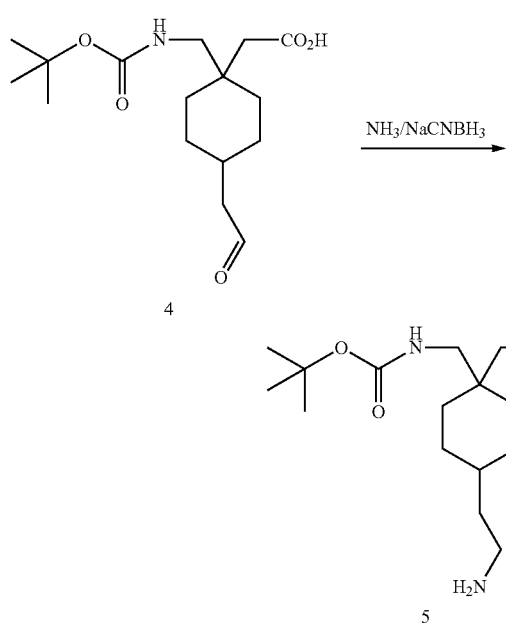

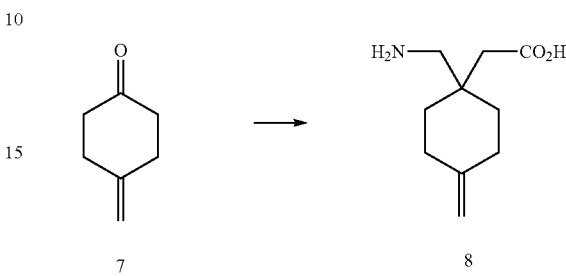

To a stirred saturated solution of anhydrous ammonia in methanol (10 ml) at 0° C. was added compound 4 (626 mg, 2 mmole). After 30 min., sodium cyanoborohydride (60 mg) was added in portions of 20 mg over 1 hour. After the addition was completed the reaction was allowed to stir for an additional 2 hours. To the reaction was added 1N HCl until the reaction was acidic (pH 3-5). The reaction was then evaporated to dryness and extracted with THF, and evaporated to dryness to give compound 5 as a semi glass solid (450 mg, 71%).

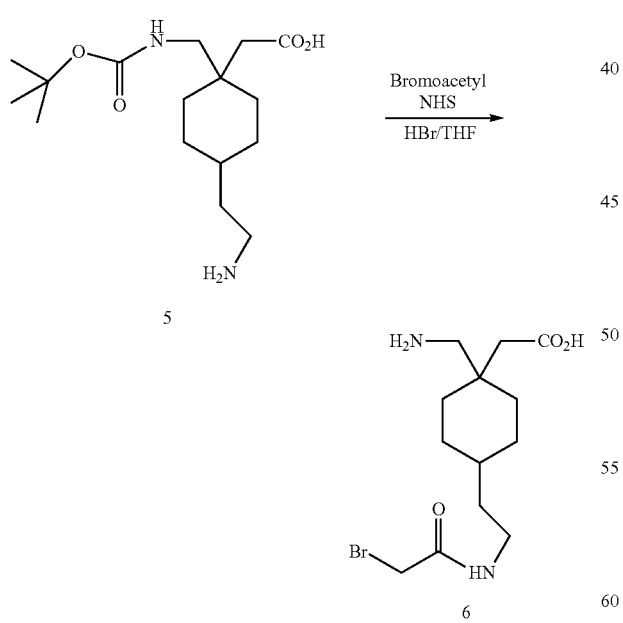

To a stirred solution of the amine 5 (314 mg, 1 mmol) in THF (6 ml) was added bromo acetyl NHS ester (260 mg, 1.2 mmol). The mixture was stirred overnight and then diluted with water (10 ml). The mixture was then extracted with DCM (3×30 ml). The combined DCM layers were washed with brine (30 ml), dried over MgSO₄ and evaporated to dryness under vacuum. The crude product was then purified on a silica gel column (DCM:MeOH, 95:5) to give the bromoacetyl 6 (410 mg, 94%) as a white foam. The foam was dissolved in anhydrous DCM (10 ml) and HBr (1N in DCM, 0.5 ml) was added at 0° C. The reaction was stirred for 30 min and then evaporated to dryness to give compound 6 HCl salt as a white powder (350 mg, 98%).

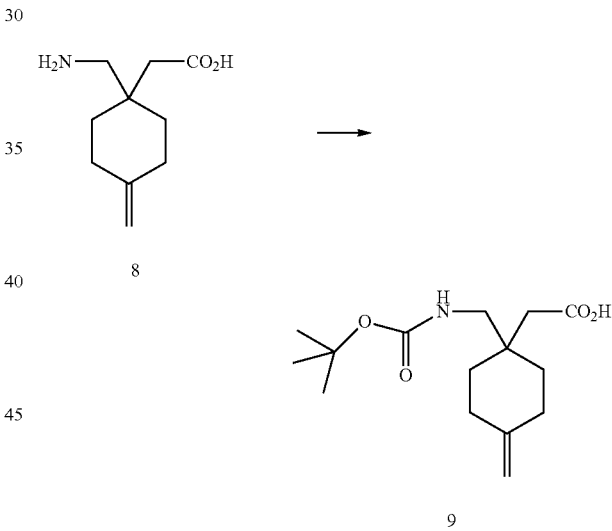

Compound 7 described in S. Danishefsky, et al., Tetrahedron (1998), 12721 and J. Varghese, et al., WO 2006/010094 and WO 2005/087752, which are incorporated herein by reference, (11.0 gram, 0.1 mol) was converted to compound 8 as described in the literature U.S. Pat. Publication No. 2007/0123591 and Chinese Pat. CN1740161, which are incorporated herein by reference, in overall yield of 68% as an off white powder.

Compound 8 (8.44 grams, 40 mmol) was converted to compound 9 as described in S. Raillard, et al., U.S. Pat. Publication No. 2004/0014940, which is incorporated herein by reference, as a white solid in 85% yield.

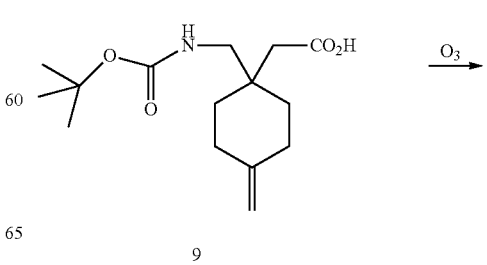

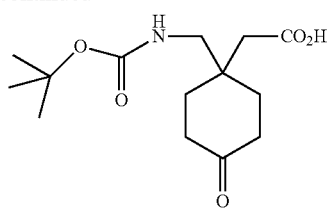

10

To a stirred solution of compound 9 (4.75 gram, 20 mmol) in methanol (150 ml) at −78° C. was bubbled ozone gas (1 ml/min) from an ozone generator for 1 hour. Nitrogen gas was then bubbled for 1 minute and mercaptomethanol (1.5 ml) was added to the reaction mixture and allowed to come to room temperature by removing the cooling bath. The solvent was than removed under reduced pressure to give compound 10 (4.84 grams, 84%).

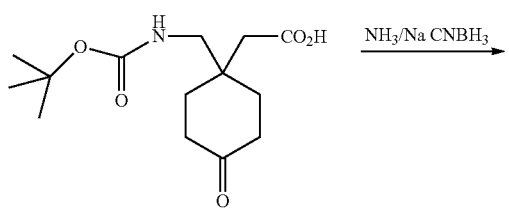

10

To a stirred saturated solution of anhydrous ammonia in methanol (10 ml) at 0° C. was added compound 10 (855 mg, 3 mmol). After 30 min., sodium cyanoborohydride (90 mg) was added in portions of 30 mg over 1 hour. After the addition was completed the reaction was allowed to stir for an additional 2 hours. To the reaction was added 1N HCl until the reaction was acidic (pH 3-5). The reaction was then evaporated to dryness and extracted with THF, and evaporated to dryness to give compound 11 as an off white solid (429 mg, 50%).

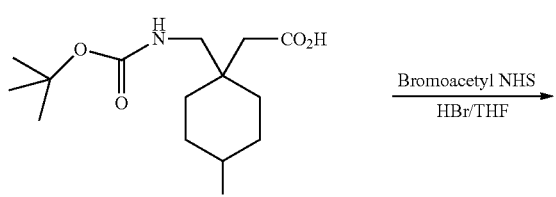

11

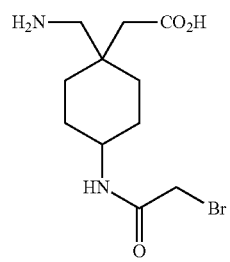

12

To a stirred solution of the amine 11 (286 mg, 1 mmol) in anhydrous THF (8 ml) was added bromo acetyl NHS ester (260 mg, 1.2 mmol). The mixture was stirred overnight and then diluted with water (15 ml). The mixture was then extracted with DCM (3×30 ml). The combined DCM layers were washed with brine (40 ml), dried (MgSO4) and evaporated to dryness under vacuum. The crude product was then purified on a silica gel column (DCM:MeOH, 90:10) to give the bromoacetyl 12 (345 mg, 85%) as a white solid. The solid was dissolved in anhydrous DCM (10 ml) and HBr (1N in DCM, 0.5 ml) was added at 0° C. The reaction was stirred for 30 min and then evaporated to dryness to give compound 12 HCl salt as a white powder (325 mg, 95%).

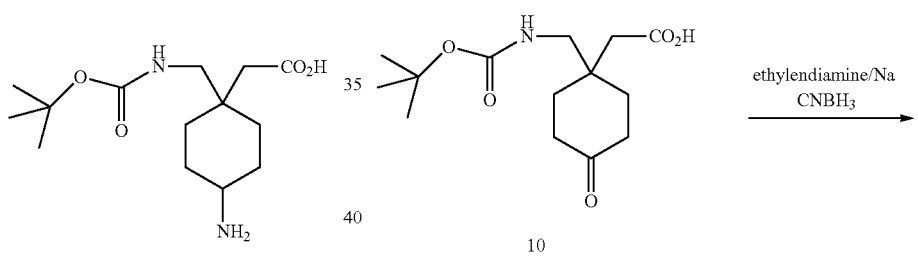

10

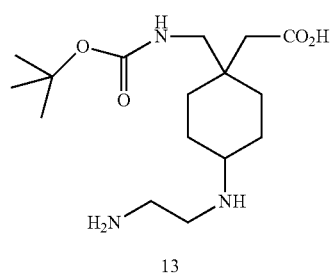

13

To a cold stirred saturated solution of ethylenediamine (900 mg, 15 mmol) in methanol (20 ml) at 0° C. was added compound 10 (855 mg, 3 mmol). After 30 min., sodium cyanoborohydride (90 mg) was added in portions of 30 mg over 1 hour. After the addition was completed the reaction was allowed to stir overnight. To the reaction was added 1N HCl until the reaction was acidic (pH 3-5). The reaction was then evaporated to dryness and extracted with THF, and evaporated to dryness to give compound 13 as white solid (395 mg, 40%).

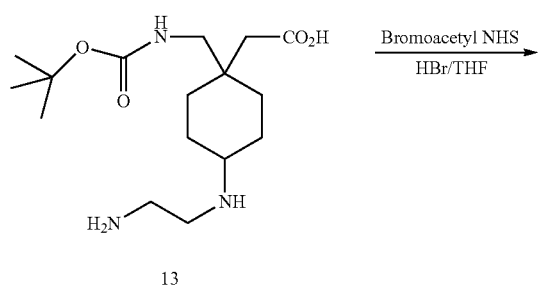

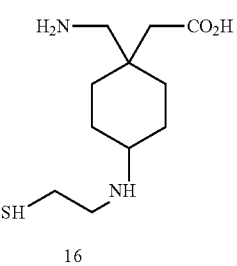

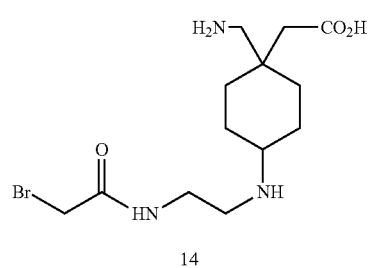

The same reaction conditions were used as for the preparation of compound 12 to prepare compound 14 in 95% yield as a pale yellow solid.

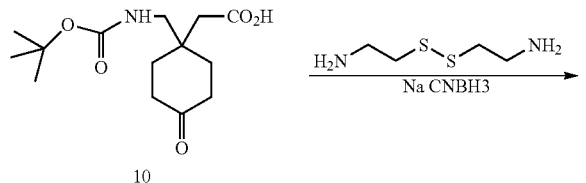

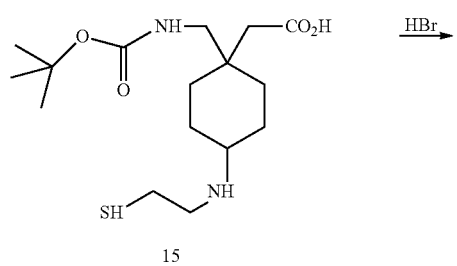

The same reaction conditions were used as for the preparation of compound 13 to prepare compound 15 as a pale yellow solid in 35% yield.

Compound 15 (345 mg, 1 mmol) was dissolved in anhydrous DCM (10 ml) and HBr (1N in DCM, 0.5 ml) was added at 0° C. The reaction was stirred for 30 min and then evaporated to dryness to give compound 16 HCl salt as a pale yellow solid (233 mg, 95%.

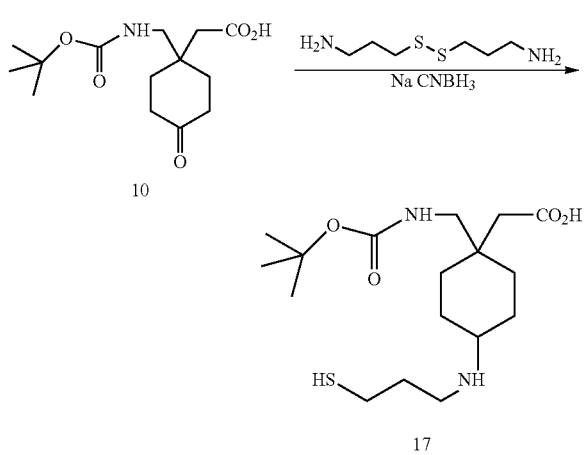

The same reaction conditions were used as for the preparation of compound 15 to prepare compound 17 in 35% yield as a pale yellow solid.

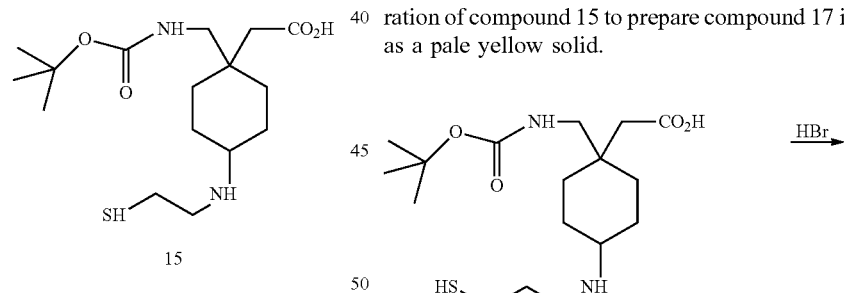

The same reaction conditions were used as for the preparation of compound 16 to prepare compound 18 as a pale yellow solid in 95% yield.

Example 2

Preparation of Carboxyl Modified Gabapentin Derivative (Formula II)

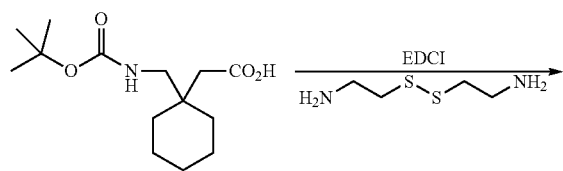

19

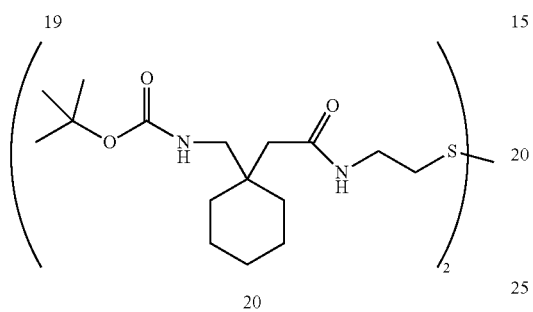

20

To a stirred solution of compound 19 as described in Chinese Pat. CN1740161 and S. Raillard, et al., U.S. Pat. Publication No. 2004/0014940, which are incorporated herein by reference, (2.71 gram, 10 mmol) in THF (100 ml) was added DCC (2.27 gram, 11 mmol) and NHS (1.61 gram, 14 mmol). The mixture was stirred for 6 hours. The diamine (7.60 g, 50 mmol) and DIEA (4.0 ml, 22 mmol) were added at room temperature and the reaction was stirred overnight. The solvent was then evaporated to dryness under vacuum. To the residue was added water (60 ml) and extracted with ethyl acetate (2×50 ml). The combined organic layers were then washed with HCl (1N, 20 ml), and saturated sodium bicarbonate (20 ml) and dried ($Na_2SO_4$). The ethyl acetate was removed under reduced pressure to give the crude product. The crude product was purified on a silica gel column (EtOAc:hexane, 1:3) to give compound 20 (2.79 g, 85%) as a white solid.

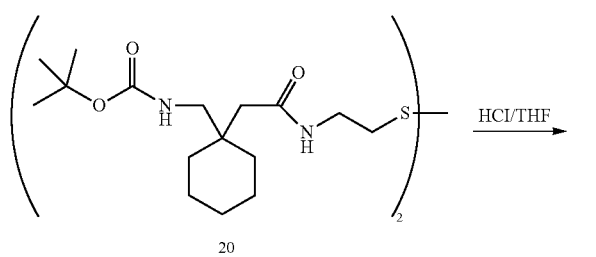

20

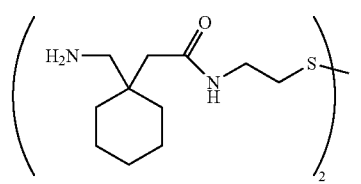

21

To a stirred solution of compound 20 (329 mg, 1 mmol) in THF (5 ml) was added HCl (gas to saturate) at 0° C. The reaction was stirred for 1 hour and then was evaporated to dryness to give compound 21 as a pale yellow solid (225 mg, 99%).

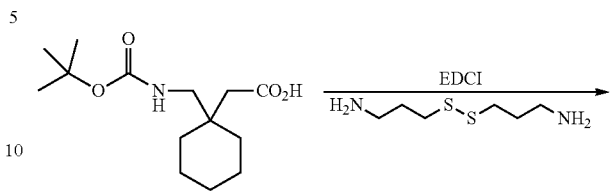

19

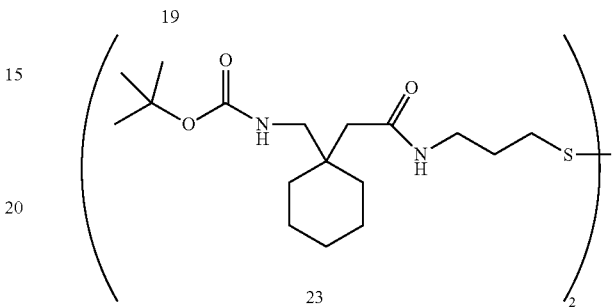

23

The same reaction conditions were used as for the preparation of compound 20 to prepare compound 23 in 80% yield as pale yellow foam.

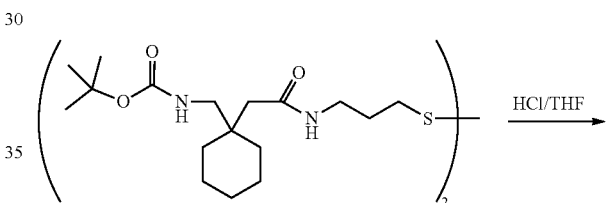

23

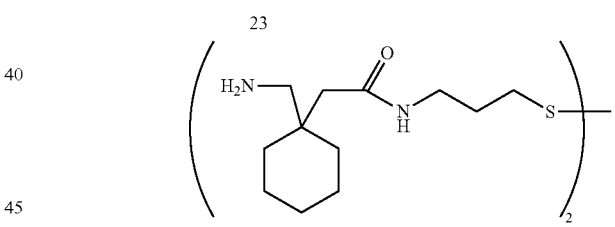

24

The same reaction conditions were used as for the preparation of compound 21 to prepare compound 24 in 98% yield as a pale yellow solid.

Example 3

Preparation of Amine Modified Gabapentin Derivative (Formula I)

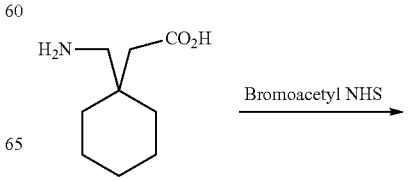

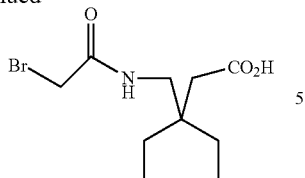

25

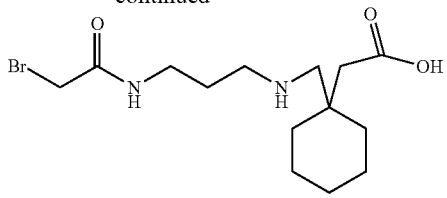

28

To a stirred solution of gabapentin (1.71 gram, 10 mmol) in DMF (50 ml) and triethyl amine (2 ml) was added bromo acetyl NHS ester (2.60 gram, 12 mmol). The mixture was stirred overnight and then diluted with water (100 ml). The mixture was acidified with 1N HCl and was then extracted with ethyl acetate (3×60 ml). The combined ethyl acetate layers were washed with brine (30 ml), dried (MgSO$_4$) and evaporated to dryness under vacuum. The crude product was then purified on a silica gel column (DCM:MeOH, 95:5) to give the bromoacetyl 25 (2.48 gram, 85%) as a white foam.

To a stirred solution of the amine 27 (284 mg, 1 mmol) in anhydrous THF (8 ml) was added bromoacetyl NHS ester (260 mg, 1.2 mmol). The mixture was stirred overnight and then diluted with water (20 ml). The mixture was then extracted with DCM (3×30 ml). The combined DCM layers were washed with brine (30 ml), dried (MgSO$_4$) and evaporated to dryness under vacuum. The residue was purified on a silica gel column (DCM:MeOH, 95:5) to give the t-butyl ester intermediate. The ester was dissolved in DCM (10 ml) and TFA (0.2 ml) was added at room temperature. The reaction was stirred for 45 min and then evaporated to dryness to give compound 28 as the TFA salt (279 mg, 80%).

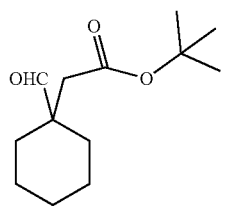

26

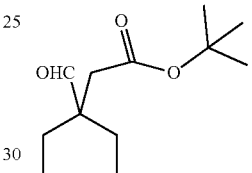

26

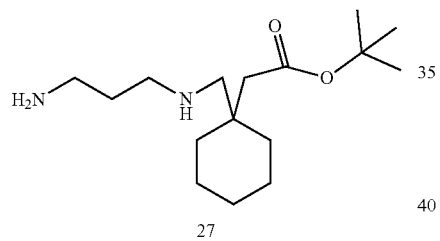

27

To a solution of compound 26 as described in D. Gopal, U.S. Pat. Publication No. 2005/0148792 and P. Rossi, WO 2002/074727, which are incorporated herein by reference, (2.26 grams, 10 mmol) and ethylenediamine (3.0 grams, 50 mmol) in ethanol (100 ml) was added activated Pd (100 mg). The reaction mixture was then purged with N$_2$ gas twice and then the mixture container was filled with H$_2$ gas to 60 PSI. The mixture was stirred at room temperature overnight. The mixture was then passed through a pad of Celite and the pad was washed with ethanol (2×50 ml). The combined ethanol fractions were evaporated to dryness. The residue was purified on a silica gel column (DCM:MeOH, 90:10) to give compound 27 as a white powder (1.7 g, 60%).

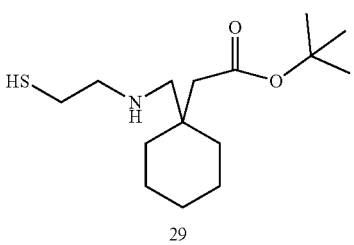

29

The same reaction conditions were used as for the preparation of compound 27 to prepare compound 29 as a pale yellow solid (1.5 gram, 50%).

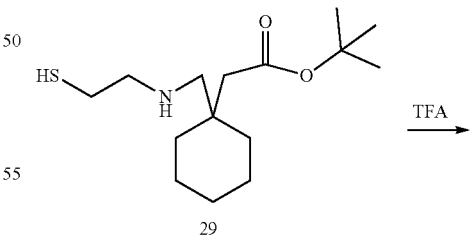

29

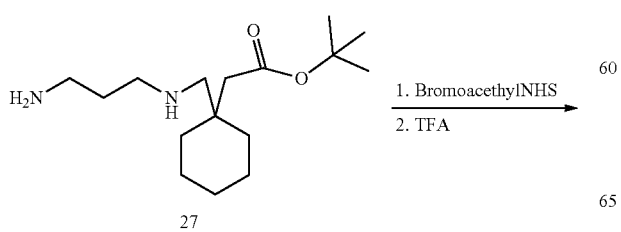

27

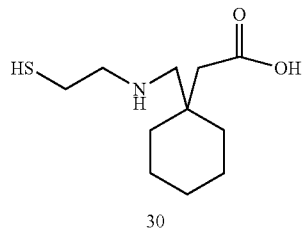

30

A stirred solution of compound 29 (301 mg, 1 mmol) in DCM (20 ml) was treated with TFA (0.2 ml) for 1 hour at room temperature. The solvent was then removed to give the TFA salt of compound 30 as a white solid.

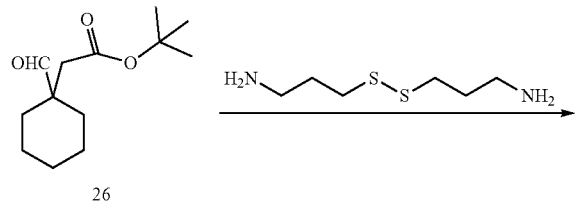

The same reaction conditions were used as for the preparation of compounds 27 and 29 to prepare compound 31 in 50% yield as a pale yellow foam.

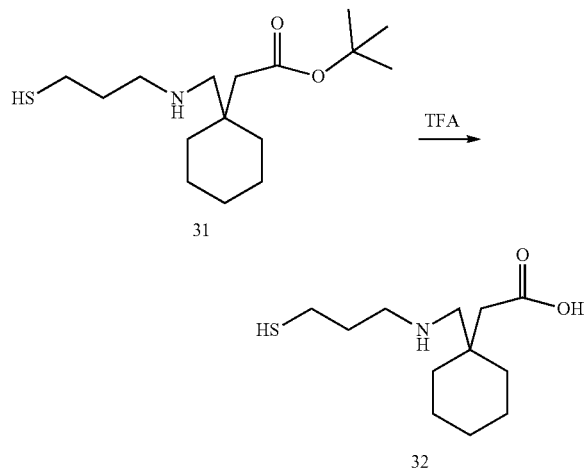

The same reaction conditions were used as for the preparation of compound 30 to prepare compound 32 as the TFA salt.

Example 4

Conjugation: Preparation of Gabapentin-SH-KLH Immunogen (51)

a) Preparation of Thiolated KLH (35)

One vial of lyophilized KLH (Pierce, 21 mg) was reconstituted with 3 mL of phosphate buffer (0.1 M, 0.15 M NaCl, 1 mM EDTA, pH 8.0). The KLH solution was transferred to a reaction vial Immediately before reaction, 6-8 mg of SATA (N-Succinimidyl-S-acetylthioacetate) was dissolved in 0.5 mL of DMSO (results in 55 mM solution). 30 µl of the SATA solution was combined with 3.0 mL of protein solution (7 mg/mL). The contents were mixed and reaction incubated at room temperature for at least 30 minutes. A Sephadex G-50 column was equilibrated with two column volumes of buffer (0.1 M phosphate, 0.15 M NaCl, pH 7.2-7.5). The reaction mixture was applied to column. Fraction (500 µL) was collected immediately. The fractions that contain protein were identified by measuring absorbance at 280 nm. Protein fractions were pooled to give 12 mL. Deacylation to generate a sulfhydryl for use in cross-linking was accomplished adding 1.2 mL deacetylation solution (0.5 M Hydroxylamine, 25 mM EDTA in PBS, pH 7.2-7.5). Contents were mixed and reaction incubated for 2 hours at room temperature. Sephadex G-50 desalting column was used to purify the sulfhydryl-modified protein from the hydroxylamine in the deacetylation solution. The pooled fraction was concentrated to 2.6 mL (8 mg/mL) using Amicon concentrator. See FIG. 7B.

b) Conjugation with Thiolated KLH

Dithiothreitol (DTT, 1 mM) was added to thiolated KLH to ensure reduction of disulfide bonds. The solution was allowed to mix overnight at 4° C. 10.2 mg Bromoacetamido gabapentin hapten (25) was dissolved in 0.2 mL DMF. Gabapentin hapten (25) DMF solution was added in 5 to 10 µL quantities to a solution of thiolated KLH (35). The reaction was continued overnight at 4° C. This solution was dialyzed against three changes (2.0 liter each) of HEPES buffer (10 mM, pH 7.0, 1 mM EDTA). This procedure yielded immunogen (51). See FIG. 8H.

Gabapentin derivative (25) is used in this Example. This conjugation technique is generally applicable to all gabapentin haptens Containing Bromoacetamido—such as gabapentin derivatives (6), (12), (14), and (28). See FIGS. 8A, 8B, 8C, and 8I.

Example 5

Conjugation: Preparation of Gabapentin-SH-KLH Immunogen (43)

a) Preparation of Bromoacetyl KLH (33)

To a solution of KLH (20 mg) in $NaH_2PO_4$—$Na_2HPO_4$ buffer (pH=8.0, 0.1M, 2.0 mL) at 4° C. (ice-bath) was added a solution of bromoacetic acid NHS ester (5.8 mg, 0.024 mmol) in DMF (0.2 mL). The pH value was maintained at 8.0. The reaction mixture was stirred in the cold-room (4° C.) for 16 hours. The mixture was purified by a Sephadex G-50 column, eluting with $NaH_2PO_4$—$Na_2HPO_4$ buffer (pH=7.00, 0.025 M). The eluted fractions from the column were monitored by UV at 280 nm. A clean separation between bromoacetyl-KLH and the hapten was obtained. Fractions containing the product were pooled together (8.0 mL) and concentrated to 3.0 mL of bromoacetyl-KLH (33) by an Amicon concentrator for the next reaction. See FIG. 7A.

b) Preparation of Gabapentin KLH Immunogen (43)

2.0 mg hapten (16) was dissolved in 100 µL DMF. To a solution of bromoacetyl-KLH (33) (3.0 mL, pH=7.00) was added the above hapten (16) solution slowly at 4° C. under nitrogen. The pH value was maintained at 7.0. The reaction was stirred at 4° C. (cold room) for 16 hours. The reaction mixture was separated using a Sephadex G-50 column equilibrated with $NaH_2PO_4$—$Na_2HPO_4$ buffer (pH=7.0, 0.025 M). The UV detector at 280 nm monitored the eluted fractions from the column. A clean separation between KLH immunogen and the hapten was obtained. Fractions containing protein (43) were pooled to a total volume of 9 mL and concentrated to 5 mL. The concentration of immunogen (43) was measured by using BCA Protein Concentration Assay.

The Immunogen (43) had a concentration of 3.5 mg/mL with a hapten number of 1280, and can be used for the immunizations. See FIG. 8D.

Gabapentin SH derivative (16) is used in this Example. However, this conjugation technique is generally applicable to gabapentin derivatives (18), (21), (24), (30), and (32). See FIGS. 8E, 8F, 8G, 8J and 8K.

Example 6

Conjugation: Native G6PDH and Gabapentin Containing Reactive Sulfhydryl Groups

Native G6PDH was buffer exchanged with 50 mM phosphate-1.0 mM EDTA, pH 8.0. The protein solution was chilled in an ice bath and mixed with aliquots (30 µL) of a 0.2 M solution of N-hydroxysucinimidyl bromoacetate in DMF. After incubation in ice bath for 1 hr enzyme activity was measured. This addition of the DMF aliquots was continued till the enzyme activity was deactivated to 75±5% as compared to that of the native enzyme. The derivatized protein was found to contain 0.97 moles of bromoacetamido groups per mole of the protein. The protein solution was mixed 40 fold molar excess of the thiol derivative of the hapten (16) in DMF (50 µL) and mixture stirred gently in a cold box for 16 to 24 hours. Excess hapten (16) was separated from the enzyme-hapten conjugate by passing the reaction mixture over a column of Sephadex G 50 in 50 mM phosphate, pH 7.0. The column fractions containing the enzyme-hapten conjugate were pooled by measuring absorption at 280 nm.

Gabapentin derivative (16) is used in this Example. However, this conjugation technique is generally applicable to all gabapentin Haptens to all Haptens Containing Reactive Sulfhydryl Groups. Haptens (18), (21), (24), (30), and (32) can use this conjugation procedure.

Example 7

Conjugation: G6PDH Containing Reactive Sulfhydryl Groups

Conjugation G6PDH-SH was buffer exchanged with 50 mM phosphate-1.0 mM EDTA, pH 7.25. A solution of the protein (2 mL at 5 mg/mL) was then mixed with a dithioerythreitol (25 mM final concentration in the phosphate-EDTA buffer) and mixture incubated at 4° C. for 16 hours. The protein solution was then buffer exchanged with 50 mM phosphate, 1.0 mM EDTA, 5 mM DTT, pH 7.25. The protein solution (2 mL at 5 mg/mL) was mixed with 40 fold molar excess of a DMF solution (0.05 mL) of hapten (25) and reaction mixture stirred gently at 4° C. for 16 to 24 hours. Excess hapten (25) was separated from the enzyme-hapten conjugate by passing the reaction mixture over a column of Sephadex G 50 in 50 mM phosphate, pH 7.0. The column fractions containing the enzyme-hapten conjugate were pooled by measuring absorption at 280 nm.

Gabapentin derivative (25) is used in this Example. However, this conjugation technique is generally applicable to all gabapentin Haptens to all Haptens Containing Reactive Bromoacetamido-Groups. Haptens (6), (12), (14), (25), and (28), can use this conjugation procedure.

Example 8

Preparation of Gabapentin-SH-G6PDH (52)

Preparation of Thiolated G6PDH (36)

The N-succinimidyl S-acetylthioacetate (SATA) reagent was used to introduce protected sulfhydryls into native G6PDH. 21 mg G6PDH was dialyzed against phosphate buffer (0.1 M, 0.15 M NaCl, 1 mM EDTA, pH 8.0). The dialyzed G6PDH was transferred to a reaction vial. Immediately before reaction, 6-8 mg of SATA was dissolved in 0.5 mL of DMSO (results in 55 mM solution). Combined was 3.0 mL of protein solution (7 mg/mL) with 30 µl of the SATA solution. The contents were mixed and reaction incubated at room temperature for at least 60 minutes. A 15 mL Sephadex G-50 column was equilibrated with two column volumes of buffer (0.1 M phosphate, 0.15 M NaCl, pH 7.2-7.5). The reaction mixture was applied to column. 1 mL fraction was collected. Fractions that contain protein were identified by measuring for those peaks having absorbance at 280 nm. 9 mL sample volume was collected (approximating 21 mg enzyme). The enzyme was dialyzed against a bicarbonate buffer (100 mM, pH 9.0) to give free SH groups.

The pH of the enzyme solution of (a) above was adjusted to 7.2 with 0.1M HCl. Gabapentin derivative (25) (11.8 mg) was dissolved in 200 µL DMF. Gabapentin (25) DMF solution was added in 5 to 10 µL quantities to a solution of 21 mg thiolated G6PDH. The reaction was continued overnight at 4° C. This solution was dialyzed against three changes (2.0 liter each) of HEPES buffer (10 mM, pH 7.0, 1 mM EDTA).

Gabapentin derivative (25) is used in this Example. However, this conjugation technique is generally applicable to all gabapentin Haptens Containing Bromoacetamido—such as haptens (6), (12), (14), and (28) were conjugated.

Example 9

Preparation of Polyclonal Antibodies Reactive to Gabapentin

Polyclonal sera from 6 live rabbit were prepared by injecting the animal with immunogenic (51). This immunogenic formulation comprises 200 ng of the immunogen for the first immunization and 100 ng for all subsequent immunizations. Regardless of immunogen amount, the formulation was then diluted to 1 mL with sterile saline solution. This solution was then mixed thoroughly with 1 mL of the appropriate adjuvant: Freund's Complete Adjuvant for first immunization or Freund's Incomplete Adjuvant for subsequent immunizations. The stable emulsion was subsequently injected subcutaneously with a 19×1½ needle into New Zealand white rabbits. Injections were made at 3-4 week intervals. Bleeds of the immunized rabbits were taken from the central ear artery using a 19×1 needle. Blood was left to clot at 37° C. overnight, at which point the serum was poured off and centrifuged. Finally, preservatives were added in order to form the polyclonal antibody material. Rabbit polyclonal antibodies to gabapentin produced by the above procedure are designated as #10925, #10926, #10927, #10928, #10929, and #10930. Rabbit polyclonal antibody #10930 is used in examples below.

The gabapentin antibodies and enzyme conjugates may be employed in assays for the detection of gabapentin. Either of the immunogens (37), (39), (41), (43), (45), (47), (49), (51), (53), (55) or (57) can be injected into a mouse, sheep or rabbit to raise antibody.

Rabbit polyclonal antibody #10930 was screened for curve size, precision, and specificity. The obtained antibody was added into the antibody diluent to prepare the antibody reagent. The antibody reagent consists of antibody as prepared above, buffer, stabilizers, preservatives, and the substrates for the enzyme conjugate NAD and glucose 6 phosphate. Enzyme conjugate comprising compound (38), (40) (42),(44) (46), (48), (50), (52), (54), (56) or (58) and G6PDH was added into the conjugate reagent to prepare the enzyme conjugate reagent. The enzyme conjugate reagent consists of the conjugate, buffer, stabilizers and preservatives. Enzyme conjugate (52) is used with rabbit polyclonal antibody #10930 in examples below.

Figure 6:
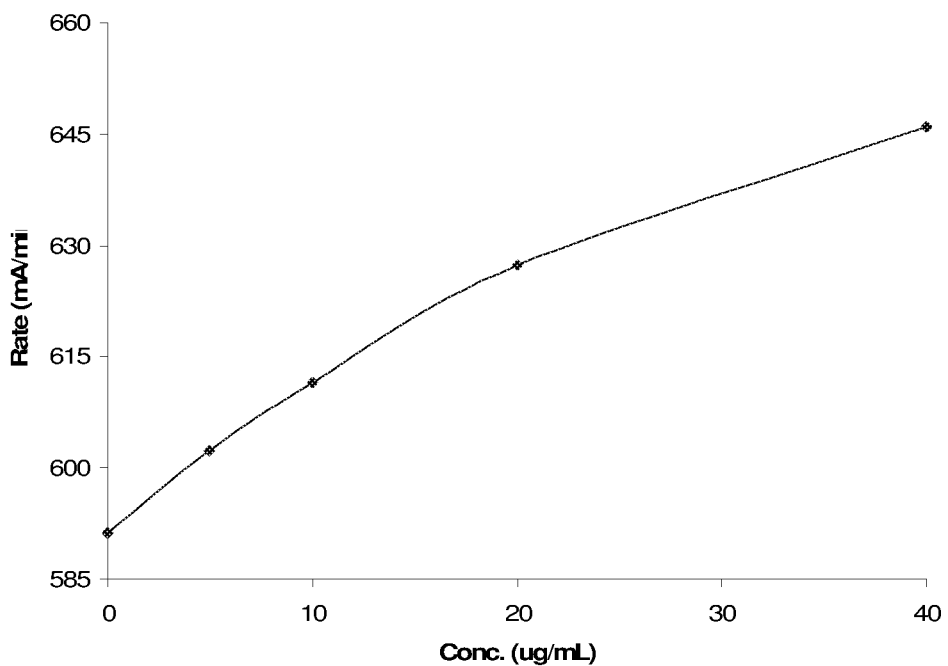
FIG. 6 is a calibration curve showing the change in optical density according to the concentration of gabapentin in a sample.

The gabapentin antibodies and enzyme conjugates may be advantageously used in a homogeneous assay format to detect gabapentin in samples. An analyzer (instrument) useful to set up the assay is Roche Cobas Mira (Roche Diagnostics). Gabapentin containing sample is incubated with antibody reagent followed by the addition of the enzyme conjugate reagent. The enzyme conjugate activity decreases upon binding to the antibody. The enzyme conjugate, which is not bound to the antibody, catalyzes the oxidation of glucose 6-phosphate (G6P). The oxidation of G6P is coupled with the reduction of $NAD^+$ to NADH, which can be measured at 340 nm. The change in the absorbance at 340 nm can be measured spectrophotometrically. The gabapentin concentration in a specimen can be measured in terms of G6PDH activity. The increase in the rate at 340 nm is due to the formation of NADH and is proportional to the enzyme conjugate activity. An assay curve is generated (FIG. 6) using gabapentin spiked into negative calibrator matrix. The assay rate increases with increasing the concentration of free drug in the sample.

This technique is generally applicable to produce polyclonal antibodies to gabapentin derivatives.

Example 10

Assay Performance

Standard Curve

A series of known concentrations of gabapentin standards (ranging from 0 to 10 µg/mL) were prepared gravimetrically in MES (2-(N-Morpholino)ethanesulfonic acid, 0.01 M, pH 5.5) formulated with EDTA, protein additive, detergent, antifoam agent, and preservative. Similarly, quality control samples were prepared (1.0 and 5.0 µg/mL).

Gabapentin was dissolved in methanol to give a stock solution of 1000 µg/mL. Pooled human serum was aliquoted in 10 mL portions. Gabapentin stock solution was added to the aliquots in preparing a series of known concentrations of gabapentin calibrators ranging from 0 to 50 µg/mL. Antibody #10930 Reagent was prepared by adding antibody #10930 to antibody/substrate diluent. The antibody/substrate reagent was assayed with Enzyme Conjugate Reagent (52). Calibration curves were generated on the Cobas Mira® by assaying each level in duplicate. An example of these calibrator rates is shown in Table 1 and a typical plot is provided in FIG. 6.

TABLE 1

| Calibrator Reaction Rate | |
|---|---|
| Gabapentin Concentration (µg/mL) | Reaction Rate (mA/min) Average of Duplicates |
| 0.00 | 519.2 |
| 5.00 | 602.3 |
| 10.00 | 611.4 |
| 25.00 | 627.3 |
| 50.00 | 646.0 |
| 0.00 | 519.2 |

Specificity of the Immunoassay

The specificity of the immunoassay was evaluated by adding potentially crossreactant drugs to human serum and determining the increase in the apparent concentration as a result of the presence of crossreactant. Separate stock solutions of gabapentin were prepared by dissolving the drug in methanol to give a stock solution of 1000 µg/mL. 10 µg/mL of crossreactant plus 5 µg/mL of gabapentin was added to individual human serum samples to give a final volume of 1 mL. Each sample was assayed in duplicate. Testing was performed on the Cobas Mira Analyzer®. The percentage concentration above 5 µg/mL of gabapentin was calculated for each crossreactant.

TABLE 2

| Gabapentin Cross-Reactivity of Antibody with other Anti epileptic drugs | |
|---|---|
| AED | Percent Increase in Apparent Gabapentin |
| Gabapentin 0 µg/mL (Control) | 0% |
| Gabapentin 35 µg/mL (Control) | 98% |
| Lamotrigine 100 µg/mL | 0% |
| Zonisamide 50 µg/mL | 0% |
| Levetiracetam 100 µg/mL | 0% |
| Carbamazepine 100 µg/mL | 0% |
| Valproic Acid 100 µg/mL | 0% |

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

We claim:

1. A conjugate comprising a compound immobilized on a solid support for use in a gabapentin immunoassay for detecting the presence or absence of gabapentin in a sample, wherein the compound has the structure:

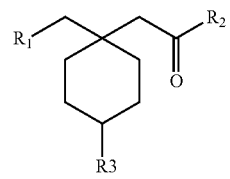

wherein:
$R_1$, $R_2$, or $R_3$ is -X-W-L-Z,
when $R_1$ is -X-W-L-Z, X is NH, and $R_2$ is —OH, and $R_3$ is —H, when $R_2$ is -X-W-L-Z, X is NH, $R_1$ is —$NH_2$, and $R_3$ is —H, and when $R_3$ is -X-W-L-Z, X is a heteroatom or lower alkyl group, $R_1$ is —$NH_2$, and $R_2$ is —OH;

W is a lower alkyl group or a carbonyl group;

L is a linker or at least one bond between W and Z; and

Z is a reactive functional group capable of reacting with a reactive partner to form a covalent bond, wherein the compound is covalently immobilized on the solid support through said reactive functional group Z.

2. The conjugate of claim 1, wherein said linker comprises 0 to 40 carbon atoms and 0-6 heteroatoms.

3. The conjugate of claim 2, wherein W is a lower alkyl and said linker is selected from the group consisting of:
—$(CH_2)_nC(O)$—;
—$C(O)(CH_2)_n$—;
—$C(O)(CH_2)_nNH$—$C(O)$—;
—$C(O)(CH_2)_mNH$—$C(O)(CH_2)_n$—;
—$(CH_2)_nSCH_2C(O)$—;
—$(CH_2)_mSCH_2C(O)(CH_2)_n$—;
—$(CH_2)_mC(O)NH(CH_2)_n$—;
—$(CH_2)_nNH$—$C(O)$—;
—$(CH_2)_mNH$—$C(O)(CH_2)_n$—;
—$C(O)$—$(CH_2)_n$—; and
—$(CH_2)_n$—, and wherein m, n, o, and p are independently selected from an integer from 0 to 10.

4. The conjugate of claim 2, wherein W is a carbonyl and said linker is selected from the group consisting of:
—$(CH_2)_nC(O)$—;
—$(CH_2)_nSCH_2C(O)$—;
—$(CH_2)_mSCH_2C(O)(CH_2)_n$—;
—$(CH_2)_mC(O)NH(CH_2)_n$—;
—$(CH_2)_nNH$—$C(O)$—;
—$(CH_2)_mNH$—$C(O)(CH_2)_n$—; and
—$(CH_2)_n$—, and wherein m, n, o, and p are independently selected from an integer from 0 to 10.

5. The conjugate of claim 1, wherein W is a lower alkyl group and the lower alkyl group is a methyl group.

6. The conjugate of claim 1, wherein said reactive functional group is selected from the group consisting of halogen, OH, SH, $NH_2$, O-lower alkyl, epoxy, S-acyl, carboxyl, maleimidyl, haloacetamide, hydroxysuccinimidyl, succinimidyl, carbonate, anhydride and imidate.

7. The conjugate of claim 6, wherein said halogen is Br or I.

8. The conjugate of claim 1, wherein the compound has the structure:

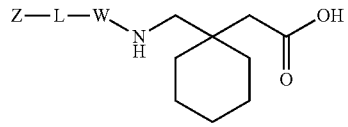

wherein W, L, and Z are as defined in claim 1, and wherein the compound is covalently immobilized on the solid support through the reactive functional group Z.

9. The conjugate of claim 8, wherein Z is SH or Br.

10. The conjugate of claim 8, wherein Z is a reactive functional group, and wherein -W-L- is a straight or branched alkyl chain.

11. The conjugate of claim 8, wherein Z is a reactive functional group, and wherein W is a lower alkyl group.

12. The conjugate of claim 1, wherein the compound has the structure:

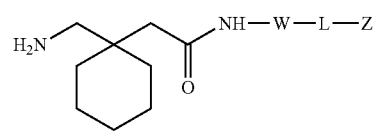

wherein W, L and Z are as defined in claim 1, and wherein the compound is covalently immobilized on the solid support through the reactive functional group Z.

13. The compound of claim 12, wherein the reactive functional group is selected from the group consisting of halogen, SH, $NH_2$, O-lower alkyl, epoxy, S-acyl, maleimidyl, haloacetamide, hydroxysuccinimidyl, succinimidyl, carbonate, anhydride and imidate.

14. The conjugate of claim 1, wherein the compound has the structure:

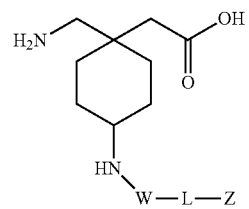

wherein W, L and Z are as defined in claim 1, and wherein the compound is covalently immobilized on the solid support through the reactive functional group Z.

15. The conjugate of claim 14, wherein Z is SH or Br.

16. The conjugate of claim 1, wherein said -X-W-L-Z is selected from the group consisting of —NH—$(CH_2)_m$—SH, —NH—CO—$(CH_2)_n$—Br, and —NH—$(CH_2)_o$—S—$CH_2$—CO—$CH_2$—Br, and wherein m, n, and o are independently selected from 2 or 3.

17. A gabapentin immunoassay kit comprising the conjugate of claim 1.

* * * * *